United States Patent
Chen et al.

(10) Patent No.: US 11,247,993 B2
(45) Date of Patent: Feb. 15, 2022

(54) PYRIDONE DERIVATIVE, COMPOSITION AND USE AS ANTIVIRAL DRUG THEREOF

(71) Applicant: JIANGXI CAISHI PHARMACEUTICAL TECHNOLOGY CO., LTD., Ganzhou (CN)

(72) Inventors: Li Chen, Suzhou (CN); Qing Shao, Suzhou (CN); Xiaojian Xue, Suzhou (CN); Xiaowen Li, Suzhou (CN)

(73) Assignee: JIANGXI CAISHI PHARMACEUTICAL TECHNOLOGY CO., LTD., Ganzhou (CN)

(*) Notice: Subject to any disclaimer, the term of this patent is extended or adjusted under 35 U.S.C. 154(b) by 0 days.

(21) Appl. No.: 16/487,088

(22) PCT Filed: Jan. 16, 2019

(86) PCT No.: PCT/CN2019/071902
§ 371 (c)(1),
(2) Date: Aug. 19, 2019

(87) PCT Pub. No.: WO2019/141179
PCT Pub. Date: Jul. 25, 2019

(65) Prior Publication Data
US 2019/0367517 A1    Dec. 5, 2019

(30) Foreign Application Priority Data

Jan. 17, 2018 (CN) .......................... 201810044308.4
Dec. 12, 2018 (CN) .......................... 201811517425.4

(51) Int. Cl.
| C07D 471/14 | (2006.01) |
| A61P 31/16  | (2006.01) |
| C07D 471/04 | (2006.01) |
| C07D 498/14 | (2006.01) |
| C07D 498/22 | (2006.01) |
| A61K 45/06  | (2006.01) |

(52) U.S. Cl.
CPC ............ *C07D 471/14* (2013.01); *A61P 31/16* (2018.01); *C07D 471/04* (2013.01); *C07D 498/14* (2013.01); *C07D 498/22* (2013.01); *A61K 45/06* (2013.01)

(58) Field of Classification Search
CPC .. C07D 471/04; C07D 471/14; C07D 498/14; A61K 31/55
See application file for complete search history.

(56) References Cited

U.S. PATENT DOCUMENTS

| 8,927,710 B2 | 1/2015 | Akiyama et al. |
| 8,987,441 B2 | 3/2015 | Takahashi et al. |
| 9,469,638 B2 | 10/2016 | Akiyama et al. |
| 9,815,835 B2 | 11/2017 | Akiyama et al. |
| 10,160,764 B2 | 12/2018 | Jain et al. |

FOREIGN PATENT DOCUMENTS

| CN | 102803260 A | 11/2012 |
| CN | 103228653 B | 3/2016 |
| EP | 2444400 B1 | 3/2018 |

(Continued)

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*

(Continued)

*Primary Examiner* — Deepak R Rao
(74) *Attorney, Agent, or Firm* — Weisun Rao; Venture Partner, LLC

(57) ABSTRACT

The present disclosure belongs to the field of medicinal chemistry, and relates to a novel pyridone derivative represented by Formula (I) or a stereoisomer, a pharmaceutically acceptable salt, a solvate or a crystal thereof, and use thereof in the preparation of a drug for preventing or treating diseases such as influenza type A viral infection and/or influenza type B viral infection, particularly use thereof as a PA subunit cap-dependent endonuclease inhibitor for preventing or treating diseases such as influenza type A viral infection and/or influenza type B viral infection. The compounds of the present disclosure have significant activity in inhibiting influenza endonuclease and influenza DNA, can be used either alone or in combination with a neuraminidase inhibitor, a nucleoside drug, a PB2 inhibitor, a PB1 inhibitor, an M2 inhibitor or other anti-influenza drugs, significantly shorten the time of influenza infection and reduces mortality, and have excellent clinical application prospects.

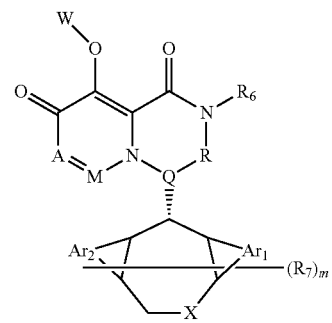

17 Claims, No Drawings

(56) References Cited

FOREIGN PATENT DOCUMENTS

| EP | 3290424 A1 | 3/2018 |
|---|---|---|
| EP | 2620436 B1 | 5/2018 |
| JP | 6249434 B1 | 12/2017 |
| WO | 2010147068 A1 | 12/2010 |
| WO | 2012039414 A1 | 3/2012 |
| WO | 2018042303 A1 | 3/2018 |

OTHER PUBLICATIONS

B. Muller et al., Antiviral Strategies in, Antiviral Strategies 1-24, 7 (H.-G. Krausslich et al., eds., 2009).*
N.E. Sharpless et al., Nature Reviews Drug Discovery 1-14, 2 (2006).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
P.D. Griffiths, Cytomegalovirus in, Principles and Practice of Clinical Virology 85-122 (A.J. Zuckerman et al., eds, 5th ed., 2001).*
Sun et al., Synthesis and evaluation of a new series of substituted acyl(thio)urea and thiadiazolo[2,3-a]pyrimidine derivatives as potent inhibitors of influenza virus neuraminidase, Bioorganic & Medicinal Chemistry, vol. 14, No. 24, pp. 8574-8581 (2006).*

\* cited by examiner

PYRIDONE DERIVATIVE, COMPOSITION AND USE AS ANTIVIRAL DRUG THEREOF

CROSS-REFERENCE TO RELATED APPLICATIONS

This application is U.S. national phase under 35 U.S.C. § 371 of International Patent Application No. PCT/CN2019/071902, filed on Jan. 16, 2019, which claims priority to Chinese Application No. 201810044308.4, filed on Jan. 17, 2018, and Chinese Application No. 201811517425.4, filed on Dec. 12, 2018, the contents of all of which are incorporated by reference in their entirety.

TECHNICAL FIELD OF THE INVENTION

The present disclosure belongs to the field of medicinal chemistry, and specifically relates to a novel pyridone derivative or a stereoisomer, a pharmaceutically acceptable salt, a solvate or a crystal thereof, to a pharmaceutical composition containing the foregoing pyridone derivative or the stereoisomer, the pharmaceutically acceptable salt, the solvate or the crystal thereof, and to use thereof as an antiviral drug, in particular, use thereof in the preparation of a drug as a cap-dependent endonuclease inhibitor for preventing and/or treating influenza infection, in particular, such as use thereof in the preparation of a drug for preventing and/or treating influenza type A viral infection and/or influenza type B viral infection.

BACKGROUND OF THE INVENTION

The influenza is an acute respiratory infection caused by an influenza virus. Every year, influenza can cause thousands of deaths, and large-scale influenza outbreaks can cause millions of deaths worldwide. Although influenza vaccines and antiviral drugs such as amantadine can be used to prevent and treat influenza, their prevention and efficacy are very limited, and it is required to develop a broader spectrum of vaccine and more effective anti-influenza drug.

The neuraminidase inhibitors Oseltamivir and Zanamivir can suppress viral budding and release, but clinically the efficacy of neuraminidase inhibitors in critically ill patients is doubtful, and the widespread resistance is also a problem of neuraminidase inhibitors that must be considered. Due to the fear of a highly lethal new influenza pandemic, a new mechanism of anti-influenza drugs is urgently needed in the clinic.

The transcription of 8 RNA fragments is a critical step in the life course of influenza viruses. RNA polymerase plays a key role in this step. RNA polymerase is a trimer composed of three subunits PA, PB1 and PB2, which is responsible for the replication and transcription of viral RNA in the nuclei of infected host cells. The transcription of influenza virus RNA has a special "cap snatching" mechanism, the PB2 subunit is responsible for recognizing and binding to the "cap structure" of the host precursor mRNA, and the PA subunit cleaves the host mRNA as a primer to initiate the transcription process. The cleaved mRNA primers are used in the PB1 subunit for the synthesis of viral mRNA. Because the cap-dependent endonuclease of the PA subunit is very conservative during influenza variation and is necessary for viral life courses, and the binding site is specific, the binding domain is well suited as a target to develop new anti-influenza drugs. Since the endonuclease binding sites of influenza type A and influenza type B are very similar, cap-dependent endonuclease inhibitors have activity against both influenza type A and influenza type B viruses. The marketed influenza treatment drug Baloxavir marboxil is a cap-dependent endonuclease inhibitor that has a clinically highly effective therapeutic effect on type A/B influenza. CN102803260A discloses a substituted polycyclic carbamoylpyridone derivative which has an inhibitory activity against a cap-dependent endonuclease and can be used as a therapeutic and/or preventive agent for influenza infectious diseases.

SUMMARY OF THE INVENTION

One of the purposes of the present disclosure is to provide a novel pyridone derivative which can be used as a cap-dependent endonuclease inhibitor and which is superior to the exsiting pyridone derivatives in at least one aspect of activity, pharmacokinetic properties such as bioavailability and cytotoxicity.

A second purpose of the present disclosure is to provide a pyridone derivative which not only has excellent cap-dependent endonuclease inhibitory activity and low cytotoxicity, but also has significantly improved pharmacokinetic properties, particularly bioavailability.

To achieve the above purposes, the present disclosure employs the following technical solutions:

A pyridone derivative represented by Formula (I) or a stereoisomer, a pharmaceutically acceptable salt, a solvate or a crystal thereof,

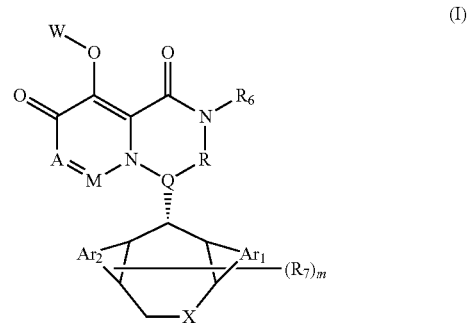

wherein:
(1) A is selected from N or $CR_1$, $R_1$ is selected from hydrogen, cyano, hydroxy, halogen, carboxyl, ester, amide, sulfonyl amide; or, $R_1$ is selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{6-10}$ aryl, $C_{6-10}$ aryloxy, $C_{6-10}$ aryloxy hydrocarbyl, $C_{6-10}$ arylamino, $C_{6-10}$ aryl sulfydryl, $C_{6-10}$ aryl carbonyl, $C_{1-6}$ hydrocarbyl sulfonyl, $C_{1-6}$ hydrocarbyl sulfonylamino, $C_{3-6}$ cycloalkyl sulfonyl, $C_{3-6}$ cycloalkyl sulfonylamino, $C_{6-10}$ aryl sulfonyl, $C_{6-10}$ aryl sulfonylamino, aminooxalyl amino, aminooxalyl, $C_{6-10}$ arylamino carbonyl or $C_{5-10}$ arylamino carbonylamino;

(2) M is selected from N or $CR_2$, $R_2$ is selected from hydrogen, cyano, hydroxy, halogen, carboxyl, ester, amide, sulfonyl amide; or, $R_2$ is selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{5-10}$ aryl, $C_{5-10}$ aryloxy, $C_{5-10}$ aryloxy hydrocarbyl, $C_{5-10}$ arylamino, $C_{5-10}$ aryl sulfydryl, $C_{5-10}$ aryl carbonyl, $C_{1-6}$ hydrocarbyl sulfonyl, $C_{1-6}$ hydrocarbyl sulfonylamino, $C_{3-6}$ cycloalkyl sulfonyl, $C_{3-6}$ cycloalkyl sulfonylamino, $C_{5-10}$ aryl sulfonyl, $C_{5-10}$ aryl sulfonylamino, aminooxalyl amino, aminooxalyl, $C_{5-10}$ arylamino carbonyl or $C_{5-10}$ arylamino carbonylamino; or, $R_1$ and $R_2$ are connected and form a first ring together with carbon atoms connected therewith, or $R_2$ and $R_7$ are connected and form a second ring together with carbon atoms connected therewith;

(3) Q is selected from N or $CR_3$, $R_3$ is selected from hydrogen, cyano, carboxyl, ester, amide; or, $R_3$ is selected from the following unsubstituted or substituted groups: $C_{1-6}$ hydrocarbyl, $C_{3-6}$ cycloalkyl, $C_{4-8}$ heterocycloalkyl, $C_{5-10}$ aryl, $C_{3-6}$ cycloalkyl sulfydryl, spirocyclic ring, bridged cyclic ring, $C_{3-6}$ cycloalkyl sulfydryl $C_{1-6}$ hydrocarbyl, $C_{3-6}$ cycloalkyl $C_{1-6}$ hydrocarbyl sulfydryl $C_{1-6}$ hydrocarbyl, $C_{3-6}$ cycloalkyl $C_{1-6}$ hydrocarbyl sulfydryl cycloalkyl, $C_{3-6}$ cycloalkyloxy cycloalkyl, cycloamide $C_{1-6}$ hydrocarbyl, cycloamide cycloalkyl, cyclosulfonyl $C_{1-6}$ hydrocarbyl, cyclosulfonyl cycloalkyl; or, $R_3$ and $R_4$ are connected and form a third ring together with carbon atoms connected therewith;

(4) R is selected from NH, carbonyl or $CR_4R_5$, $R_4$ and $R_5$ are independently selected from hydrogen, cyano, carboxyl, ester, amide; or, $R_4$ and $R_5$ are independently selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, $C_{1-6}$ hydrocarbylcarbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylamino acylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylamino carbonylamino, $C_{3-6}$ cycloalkylcarbonyl amino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{5-10}$ aryl, $C_{5-10}$ aryloxy, $C_{5-10}$ aryloxy $C_{1-6}$ hydrocarbyl, $C_{5-10}$ arylamino, $C_{5-10}$ aryl sulfydryl, $C_{5-10}$ aryl carbonyl, $C_{5-10}$ arylamino carbonyl or $C_{5-10}$ arylamino carbonylamino; or, $R_4$ and $R_5$ are connected and form a fourth ring together with carbon atoms connected therewith;

(5) $R_6$ is selected from hydrogen or the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{5-10}$ aryl, $C_{5-10}$ aryloxy, $C_{5-10}$ aryloxy hydrocarbyl, $C_{5-10}$ arylamino, $C_{5-10}$ aryl sulfydryl, $C_{5-10}$ aryl carbonyl, $C_{1-6}$ hydrocarbyl sulfonyl, $C_{1-6}$ hydrocarbyl sulfonylamino, $C_{3-6}$ cycloalkyl sulfonyl, $C_{3-6}$ cycloalkyl sulfonylamino, $C_{5-10}$ aryl sulfonyl, $C_{5-10}$ aryl sulfonylamino, aminooxalyl amino, aminooxalyl, $C_{5-10}$ arylamino carbonyl or $C_{5-10}$ arylamino carbonylamino; or, $R_6$ is a fifth ring; or, $R_6$ and R are connected and form a sixth ring together with a nitrogen atom both connected therewith, and the sixth ring is monocyclic, spiro, fused cyclic, bridged cyclic or polycyclic, and optionally contains 1, 2, 3 or more groups independently selected from heteroatom, C=O, S=O or $SO_2$, in addition to the nitrogen atom which R and $R_6$ are both connected with;

(6) m is 0, 1, 2, 3, 4 or 5, and $R_7$ is selected from hydrogen, hydroxy, cyano, halogen, carboxyl, ester, sulfonyl amide, amide; or, $R_7$ is selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{5-10}$ aryl, $C_{5-10}$ aryloxy, $C_{5-10}$ aryloxy hydrocarbyl, $C_{5-10}$ arylamino, $C_{5-10}$ aryl sulfydryl, $C_{5-10}$ aryl carbonyl, $C_{1-6}$ hydrocarbyl sulfonyl, $C_{1-6}$ hydrocarbylsulfonyl amide, $C_{3-6}$ cycloalkyl sulfonyl, $C_{3-6}$ cycloalkylsulfonyl amide, $C_{5-10}$ aryl sulfonyl, $C_{5-10}$ arylsulfonyl amide, aminooxalyl amino, aminooxalyl, $C_{5-10}$ arylamino carbonyl or $C_{5-10}$ arylamino carbonylamino; or, m is 2, 3, 4 or 5, and one or more pairs of neighboring $R_7$ are connected and form a seventhring together with carbon atoms connected therewith; or, $R_2$ and $R_7$ are connected and form the second ring together with carbon atoms connected therewith;

(7) X is selected from $Y(CH_2)_n$, $-CH(OCH_3)$, $-CH(SCH_3)$, N, O or S, Y is a single bond, NH, O or S, and n is 0, 1, 2 or 3;

(8) W is hydrogen or a group that is metabolized to a parent drug by chemical means and/or by the action of an enzyme in vivo;
(9) Ar1 and Ar2 are independently selected from a phenyl ring, or a heteroaromatic ring containing 1, 2, 3 or more heteroatoms;
(10) the first ring, the second ring, the third ring, the fourth ring, the fifth ring, and the seventh ring are independently an unsubstituted or substituted carbocyclic ring uninterrupted or interrupted by 1, 2, 3 or more selected from heteroatom, C=O, S=O or SO$_2$, and the first ring, the second ring, the third ring, the fourth ring, the fifth ring, and the seventh ring are independently monocyclic, spiro, fused cyclic, bridged cyclic or polycyclic.

According to the present disclosure, when there are a plurality of R$_7$ (that is, m is greater than 1), whether R$_7$ is the same or different is no particular required.

According to a specific aspect of the present disclosure, Ar1 and Ar2 are both a phenyl ring and the pyridone derivative is represented by Formula (II):

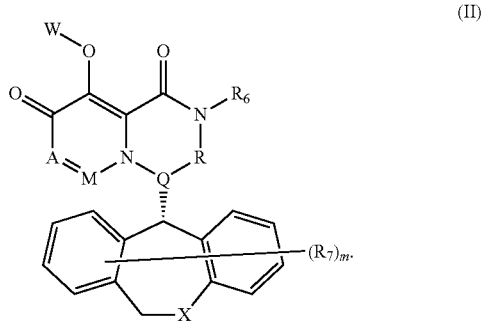

(II)

According to another aspect of the present disclosure, at least one of Ar1 and Ar2 is a heteroaromatic ring.

According to the present disclosure, in the heterocyclic ring or the heteroaromatic ring, a heteroatom is dependently selected from N, O, or S.

According to some embodiments of the present disclosure, A is CR$_1$, M is CR$_2$, and R$_1$ and R$_2$ are connected and form the first ring together with carbon atoms connected therewith.

According to some embodiments of the present disclosure, Q is CR$_3$, R is CR$_4$R$_5$, and R$_3$ and R$_4$ are connected and form the second ring together with carbon atoms connected therewith.

According to certain embodiments of the present disclosure, R is CR$_4$R$_5$, and R$_4$ and R$_6$ are connected and form the sixth ring together with nitrogen and carbon atoms connected therewith.

According to further embodiments of the present disclosure, W in Formula (I) comprises, but not limited to,
(a) —C(=O)—R$_8$; (b) —C(=O)—(CH$_2$)$_k$—R$_8$, k is selected from 0-3; (c) —C(=O)—O—(CH$_2$)$_k$—R$_8$, k is selected from 0-3; (d) —CH$_2$—O—R$_8$; (e) —CH$_2$—O—C(=O)—R$_8$; (f) —CH$_2$—O—C(=O)—O—R$_8$; (g) —CH(—CH$_3$)—O—C(=O)—R$_8$; (h) —CH(—CH$_3$)—O—C(C=O)—O—(CH$_2$)$_k$—R$_8$, k is selected from 0-3; (i) —CH$_2$—O—P(=O)(OH)$_2$; (j) —CH$_2$—O—P(=O)(OPh)(NHR$_8$); (k) —CH$_2$—O—P(=O)(OCH$_2$OC(=O)OR$_8$)$_2$; R$_8$ is selected from the following unsubstituted or substituted groups: C$_{1-6}$ hydrocarbyl, C$_{1-6}$ hydrocarbyloxy, C$_{1-6}$ hydrocarbylamino, C$_{1-6}$ hydrocarbylsulfydryl, carbonyl hydrazide, C$_{1-6}$ hydrocarbyl carbonyl, C$_{1-6}$ hydrocarbylamino carbonyl, C$_{1-6}$ hydrocarbylcarbonyl amino, C$_{1-6}$ hydrocarbyloxy carbonyl, C$_{1-6}$ hydrocarbylsulfinyl, C$_{1-6}$ hydrocarbylamino carbonylamino, C$_{3-6}$ cycloalkyl, C$_{3-6}$ cycloalkoxy, C$_{3-6}$ cycloalkylamino, C$_{3-6}$ cycloalkylsulfydryl, C$_{3-6}$ cycloalkylcarbonyl, C$_{3-6}$ cycloalkylamino carbonyl, C$_{3-6}$ cycloalkylcarbonyl amino, C$_{3-6}$ cycloalkylamino carbonylamino, C$_{4-8}$ heterocycloalkyl, C$_{4-8}$ heterocycloalkoxy, C$_{4-8}$ heterocycloalkylamino, C$_{4-8}$ heterocycloalkyl sulfydryl, C$_{4-8}$ heterocycloalkyl carbonyl, C$_{4-8}$ heterocycloalkylamino carbonyl, C$_{5-10}$ aryl, C$_{5-10}$ aryloxy, C$_{5-10}$ aryloxy hydrocarbyl, C$_{5-10}$ arylamino, C$_{5-10}$ aryl sulfydryl, C$_{5-10}$ aryl carbonyl, C$_{1-6}$ hydrocarbyl sulfonyl, C$_{1-6}$ hydrocarbyl sulfonylamino, C$_{3-6}$ cycloalkyl sulfonyl, C$_{3-6}$ cycloalkyl sulfonylamino, C$_{5-10}$ aryl sulfonyl, C$_{5-10}$ aryl sulfonylamino, aminooxalyl amino, aminooxalyl, C$_{5-10}$ arylamino carbonyl or C$_{5-10}$ arylamino carbonylamino.

According to a preferable aspect of the present disclosure, when the sixth ring is a spiro ring, a common carbon atom of the spiro ring and a nitrogen atom shared by the spiro ring and a parent ring (the parent ring refers to a ring present in general formula (I), similarly hereinafter) are adjacent or spaced by one atom.

According to another specific embodiment of the present disclosure, when the sixth ring is a spiro ring, a ring in the spiro ring that shares the nitrogen atom with a parent ring has an oxygen atom or a nitrogen atom at a position opposite to the shared nitrogen atom.

According to another preferable aspect of the present disclosure, when the sixth ring is a spiro ring, a ring in the spiro ring that shares the nitrogen atom with a parent ring is a 5-membered, 6-membered, 7-membered or 8-membered ring, and another ring is a 3-membered, 4-membered, 5-membered or 6-membered carboatomic, oxygen-containing heterocyclic or sulfur-containing heterocyclic ring unsubstituted or substituted by a substituent selected from halogen, C$_{1-3}$ hydrocarbyl or C$_{1-3}$ halohydrocarbyl.

Further preferably, when the another ring has a substituent, the substituent is selected from methyl, fluoro, chloro, bromo, monofluoromethyl, difluoromethyl, trifluoromethyl, hydroxymethyl, methoxymethyl, methoxyethyl, chloromethyl.

According to some specific and preferable aspect of the present disclosure, in Formula (I), the sixth ring formed by connecting R$_6$ and R together with the nitrogen atom connected therewith is selected from the following groups:

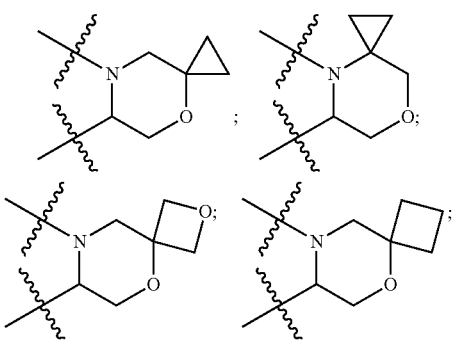

-continued

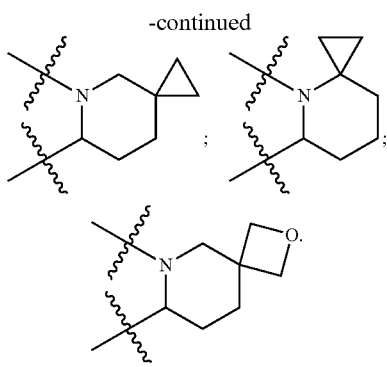

According to a preferable embodiment of the present disclosure, the pyridone derivative is represented by Formula IIa or Formula IIb:

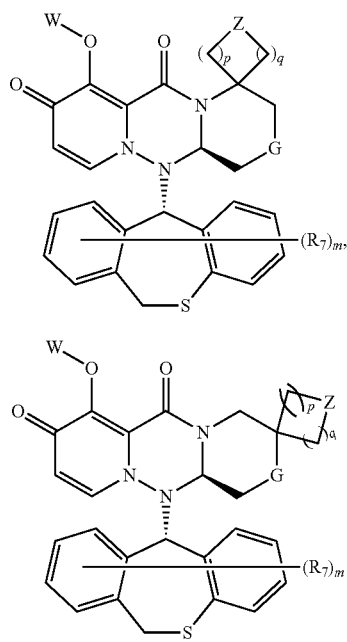

in Formula IIa and Formula IIb,
G is O or $CH_2$;
Z is selected from $CH_2$, O or S;
p and q are respectively 0, 1 or 2, and the two are not 0 at the same time, and when Z is O or S, p+q is greater than or equal to 2;
definitions of W, $R_7$ and m are respectively the same as previous.

Further preferably, in Formula IIa and Formula IIb, p+q=1 or 2 or 3, and Z is $CH_2$; or, p=1 or 2, q=1 or 2, and Z is O or S.

According to some more specific embodiments of the present disclosure, $R_7$ is selected from hydrogen, hydroxy, cyano, halogen, $C_{1-6}$ hydrocarbyl, $C_{1-6}$ halohydrocarbyl, $C_{3-6}$ cycloalkyl, $C_{1-6}$ alkoxy $C_{1-6}$ hydrocarbyl, hydroxy $C_{1-6}$ hydrocarbyl, $C_{1-6}$ hydrocarbyloxy.

Further preferably, in Formula IIa and Formula IIb, $R_7$ is connected to a phenyl ring.

Preferably, m is 1 or 2 or 3. In a specific embodiment, m is 1 or 2, and $R_7$ is selected from fluoro, chloro, bromo, methyl or trifluoromethyl, etc.

Preferably, W is selected from the following groups:
(a) —C(=O)—$R_8$; (b) —C(=O)—$(CH_2)_k$—$R_8$, k is selected from 0-3; (c) —C(=O)—O—$(CH_2)_k$—$R_8$, k is selected from 0-3; (e) —$CH_2$—O—C(=O)—$R_8$; (f) —$CH_2$—O—C(=O)—O—$R_8$; (g) —CH(—$CH_3$)—O—C(=O)—$R_8$; (h) —CH(—$CH_3$)—O—C(=O)—O—$(CH_2)_k$—$R_8$, k is selected from 0-3; (i) —$CH_2$—O—P(=O)(OH)$_2$; (j) —$CH_2$—O—P(=O)(OPh)(NHR$_8$); (k) —$CH_2$—O—P(=O)(OCH$_2$OC(=O)OR$_8$)$_2$; $R_8$ is selected from methyl, ethyl, isopropyl, or butyl.

In a specific embodiment, in Formula IIa and Formula IIb, W is (f) —$CH_2$—O—C(=O)—O—$R_8$, and $R_8$ is methyl, ethyl, isopropyl or butyl.

The pyridone derivatives represented by the above Formula IIa or Formula IIb show the best activity, and the metabolic stability of the drug is remarkably improved, and it is expected to have positive effects on the phase II metabolism glucuronidation.

According to another aspect of the present disclosure, the pyridone derivative is represented by following Formula IIc:

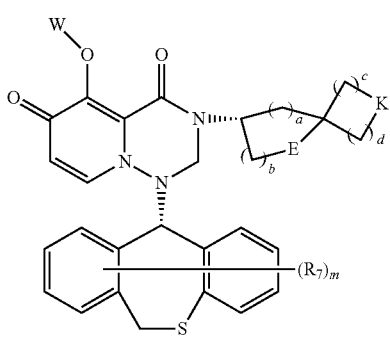

in Formula IIc, a, b, c and d are respectively 0, 1, 2 or 3, and a and b are not 0 or 3 at the same time, and c and d are not 0 or 3 at the same time;
E is $CH_2$ or O;
K is $CH_2$ or O;
definitions of W, $R_7$ and m are respectively the same as previous.

Preferably, in Formula IIc, a+b=1 or 2 or 3, and c+d=1 or 2 or 3.

Preferably, in Formula IIc, $R_7$ is selected from hydrogen, hydroxy, cyano, halogen, $C_{1-6}$ hydrocarbyl, $C_{1-6}$ halohydrocarbyl, $C_{1-6}$ alkoxy $C_{1-6}$ hydrocarbyl, hydroxy $C_{1-6}$ hydrocarbyl, $C_1$-6 hydrocarbyloxy.

More specifically, in Formula IIc, $R_7$ may be, for example, protium, deuterium, fluoro, chloro, bromo, methyl, ethyl, trifluoromethyl, methoxymethyl, etc.

Preferably, $R_7$ is connected to a phenyl ring.

Preferably, in Formula IIc, m is 0, 1, 2 or 3.

The compounds represented by Formula IIc, have a novel structure, and are highly active compounds against influenza type A and type B viruses.

According to an aspect of the present disclosure, when the fifth ring is a bridged ring, the bridged ring is bicyclic or tricyclic, and a bridgehead carbon atom or a non-bridgehead carbon atom of the bridged ring is connected to a corresponding nitrogen atom on a parent ring.

According to some specific implementations of the present disclosure, when the fifth ring is a bridged ring, the bridged ring is selected from bicyclo[1.1.1]pentane, bicyclo

[2.1.0]pentane, bicyclo[2.1.1]hexane, bicyclo[2.2.0]hexane, bicyclo[3.1.1]heptane, bicyclo[3.2.0]heptane, bicyclo[2.2.1]heptane, bicyclo[3.2.1]octane, bicyclo[3.3.0] octane.

Further, when the fifth ring is a bridged ring, the bridged ring is unsubstituted or substituted by 1, 2, 3 or more substituents selected from fluoro, chloro, bromo, trifluoromethyl, —$CH_2OH$ or —$CH_2OCH_3$.

According to another aspect of the present disclosure, the pyridone derivative is represented by following Formula IId or Formula IIe:

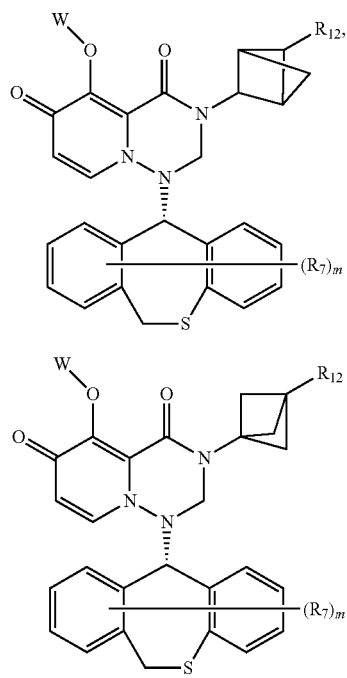

in Formula IId and Formula IIe, $R_{12}$ is selected from hydrogen, hydroxy, cyano, halogen, $C_{1-6}$ hydrocarbyl, $C_{1-6}$ halohydrocarbyl, $C_{1-6}$ alkoxy $C_{1-6}$ hydrocarbyl, $C_{1-6}$ hydroxyl-substituted hydrocarbyl, $C_{1-6}$ hydrocarbyloxy;

definitions of W, $R_7$ and m are respectively the same as previous.

Preferably, $R_{12}$ is selected from hydrogen, fluoro, chloro, methyl, ethyl, isopropyl, trifluoromethyl, methoxymethyl or hydroxymethyl, etc.

Preferably, in Formula IId or IIe, $R_7$ is selected from hydrogen, hydroxy, cyano, halogen, $C_{1-6}$ hydrocarbyl, $C_{1-6}$ halohydrocarbyl, $C_{1-6}$ alkoxy $C_{1-6}$ hydrocarbyl, hydroxy $C_{1-6}$ hydrocarbyl, $C_{1-6}$ hydrocarbyloxy. Preferably, $R_7$ is connected to a phenyl ring.

Compounds represented by Formula IId and Formula IIe are significantly optimized in space volume and spatial configuration of the groups compared to existing compounds, and thus have potent inhibition of influenza A activity, have a significant metabolic advantage (Metabolic stability), and have good development prospects.

According to one aspect of the present disclosure, when the sixth ring formed by $R_6$ and R and the nitrogen atom connected therewith is a 4-membered, 5-membered, 6-membered or 7-membered monocyclic ring, Formula (I) further meets at least one of the following conditions:

i) in addition to the nitrogen atom to which both R and $R_6$ are connected, the sixth ring optionally contains one or two of oxygen atom, another nitrogen atom, C=O, S=O and $SO_2$;

ii) the sixth ring has at least one substituent selected from hydroxy, cyano, carboxyl, ester, sulfonyl amide, amide, $C_{2-6}$ alkenyl, $C_{3-6}$ cycloalkyl, $C_{3-6}$ halocycloalkyl, $C_{3-6}$ cycloalkoxy, $C_{1-6}$ hydrocarbyloxy $C_{1-6}$ hydrocarbyl, $C_{1-6}$ hydrocarbyloxy $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino or $C_{1-6}$ hydrocarbyloxy carbonyl;

iii) the sixth ring has an intra carbon-carbon ethylenic bond, or the sixth ring has an exocyclic carbon-carbon ethylenic bond sharing one carbon atom with the sixth ring;

iv) at least one of Ar1 and Ar2 is a nitrogen-containing heteroaromatic ring;

v) at least one of A and M is N.

Further, in the condition ii), the substituent in the sixth ring is selected from $OCH_2CH_2OCH_3$, —$CH_2OCHF_2$, —$CH_2OCF_3$, —$CH_2OH$, —OH, —COOH, —$COOCH_3$, —$CONH_2$, —$OCH_2F$, —$OCHF_2$, —$OCF_3$, —$CH_2OCH_3$,

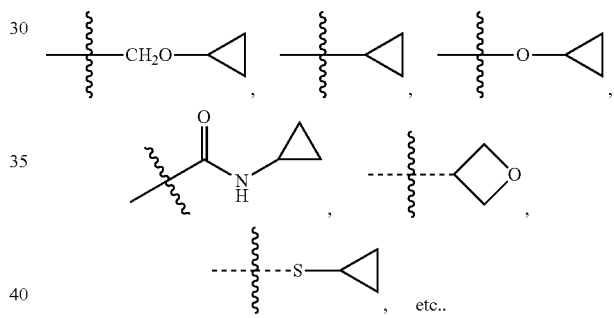

, etc..

According to a specific aspect of the present disclosure, when the sixth ring is a 4-membered, 5-membered, 6-membered or 7-membered monocyclic ring, the sixth ring contains a total of 2 heteroatoms and the 2 heteroatoms are in para or meta positions, and one of the heteroatoms is a nitrogen atom connected to both R and $R_6$, and the other heteroatom is oxygen or nitrogen. The representative sixth ring is, for example:

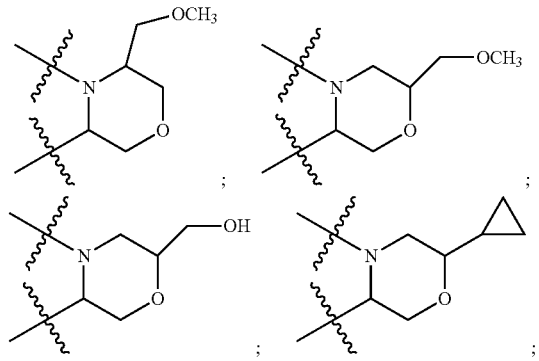

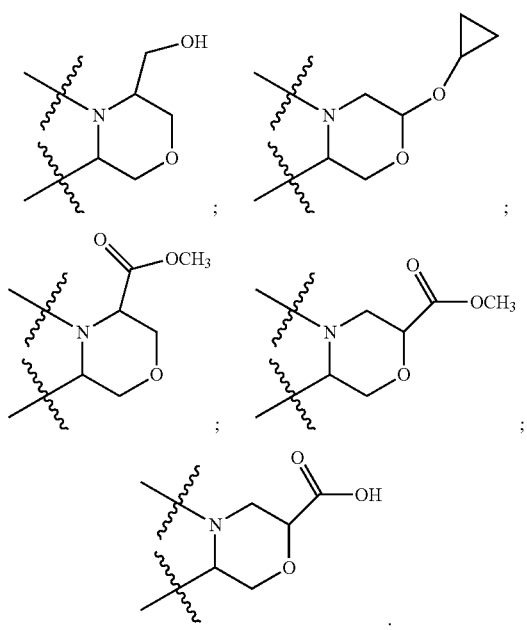

According to a more specific aspect of the present disclosure, the two heteroatoms contained in the sixth ring are all nitrogen atoms and the two nitrogen atoms are in opposite positions, while the sixth ring further has a C=O. The representative sixth ring is, for example:

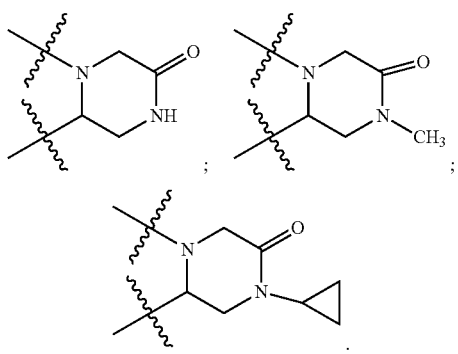

According to another specific aspect of the present disclosure, when the sixth ring is a 4-membered, 5-membered, 6-membered or 7-membered monocyclic ring, the sixth ring contains a total of 1 heteroatoms which is the nitrogen atom connected to both R and $R_6$ (that is, the nitrogen shared by the parent ring), while the sixth ring has an intra carbon-carbon ethylenic bond or an exocyclic carbon-carbon ethylenic bond. The representative sixth ring is, for example:

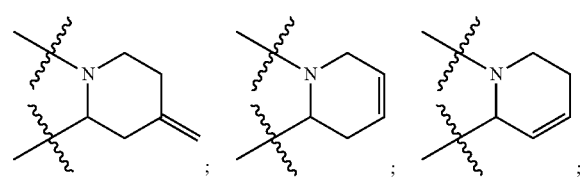

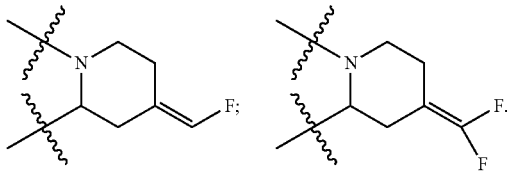

According to an aspect of the present disclosure, in Formula (I), the sixth ring is an unsubstituted morpholine ring, and further meets at least one of the following conditions:
i) one of A and M is N, and the other is correspondingly $CR_1$ or $CR_2$, while Q is CH;
ii) at least one of Ar1 and Art is a nitrogen-containing heteroaromatic ring containing 1 or 2 nitrogen atoms.

According to another aspect of the present disclosure, when the sixth ring is a fused ring, the fused ring is a bicyclic ring, and one ring sharing a nitrogen atom with the parent ring is a saturated 5-membered or 6-membered ring and optionally contains one or two groups selected from O, another N, C=O, S=O, or $SO_2$, and the other ring is a 3-membered, 4-membered, 5-membered or 6-membered saturated or unsaturated ring and optionally contains one or two groups selected from O, N, C=O, S=O or $SO_2$.

According to another aspect of the present disclosure, when the sixth ring is a fused ring, one ring of the fused ring sharing the N atom with the parent ring is a piperidine or piperazine ring, and the other ring is a 5-membered or 6-membered heteroaromatic ring or a saturated heterocyclic ring. Further, the 5-membered or 6-membered heteroaromatic ring or the saturated heterocyclic ring is unsubstituted or substituted by 1, 2, 3 or more substituents selected from hydroxy, cyano, carboxyl, ester, sulfonyl amide, amide, $C_{1-6}$ alkyl, $C_{2-6}$ alkenyl, $C_{1-6}$ halohydrocarbyl, $C_{1-3}$ alkoxy, $C_{3-6}$ cyclohydrocarbyloxy, $C_{1-6}$ hydrocarbyloxy $C_{1-6}$ hydrocarbyl, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbyl sulfonyl amide, $C_{1-6}$ hydrocarbylamino carbonyl, $C_{1-6}$ hydrocarbylcarbonyl amino or $C_{1-6}$ hydrocarbyloxy carbonyl.

According to some specific embodiments of the present disclosure, the sixth ring is selected from the following groups:

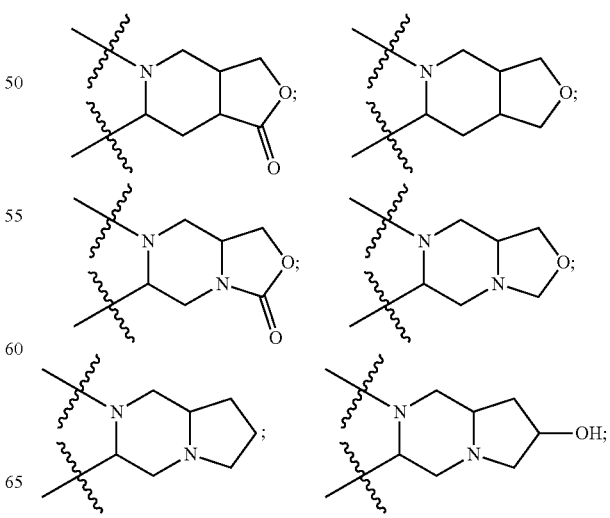

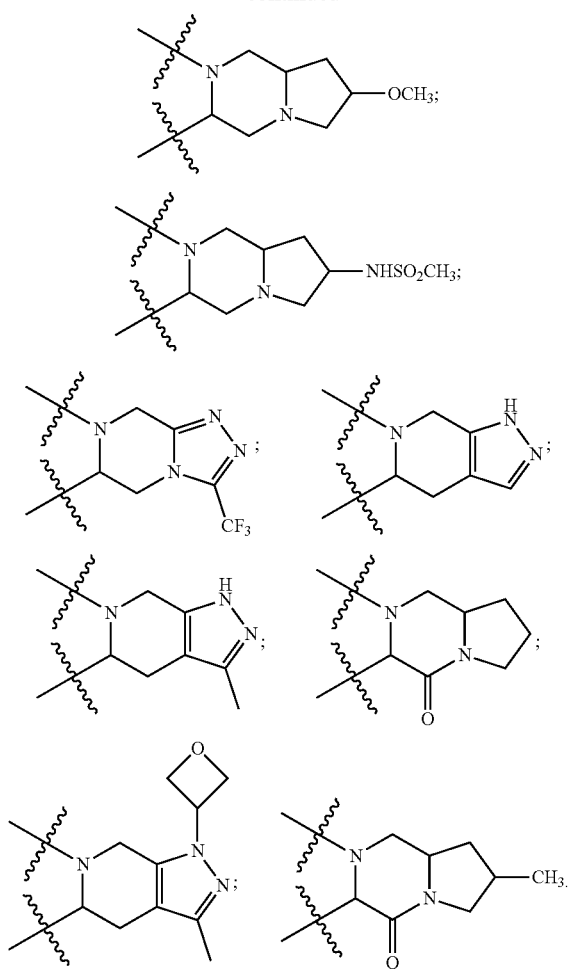

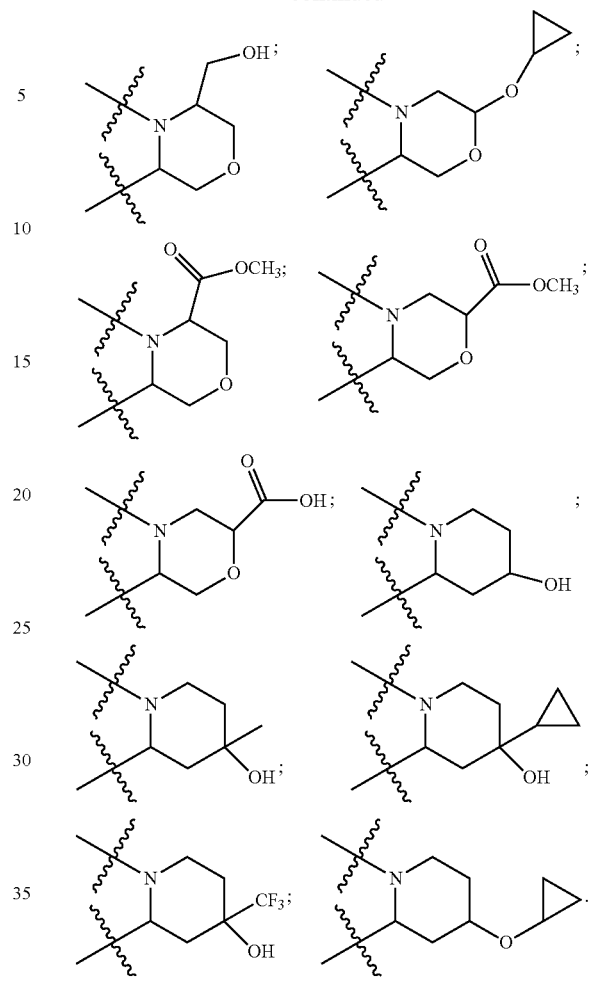

According to some embodiments of the present disclosure, the sixth ring is a piperidine ring or a morpholine ring, a substituent in the ring is preferably selected from, but not limited to, the following groups: alkoxyalkyl, haloalkoxyalkyl, hydroxyalkyl, ester, carboxyl, amide, cyano, cycloalkyl, cycloalkoxy, halocycloalkyl, hydroxy, hydroxy and alkyl/haloalkyl are connected to the same carbon atom, or cycloalkyl and hydroxyl are connected to the same carbon atom. The piperidine ring or the morpholine ring is preferably selected from the following groups:

According to some embodiments of the present disclosure, the sixth ring is a piperidine heterocyclic ring (including an aromatic heterocyclic ring or a saturated heterocyclic ring) or a piperazine heterocyclic ring (including an aromatic heterocyclic ring or a saturated heterocyclic ring), and the substituent on the ring is preferably selected from, but not limited to, the following groups: alkyl, alkoxy, haloalkyl, hydroxyl or methanesulfonylamide. The piperidine heterocyclic ring (including an aromatic heterocyclic ring or a saturated heterocyclic ring) or the piperazine heterocyclic ring is preferably selected from the following groups:

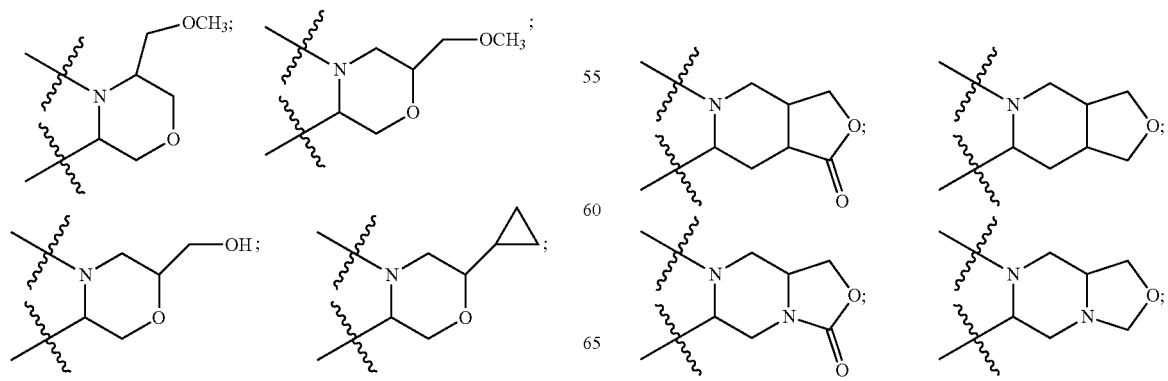

-continued

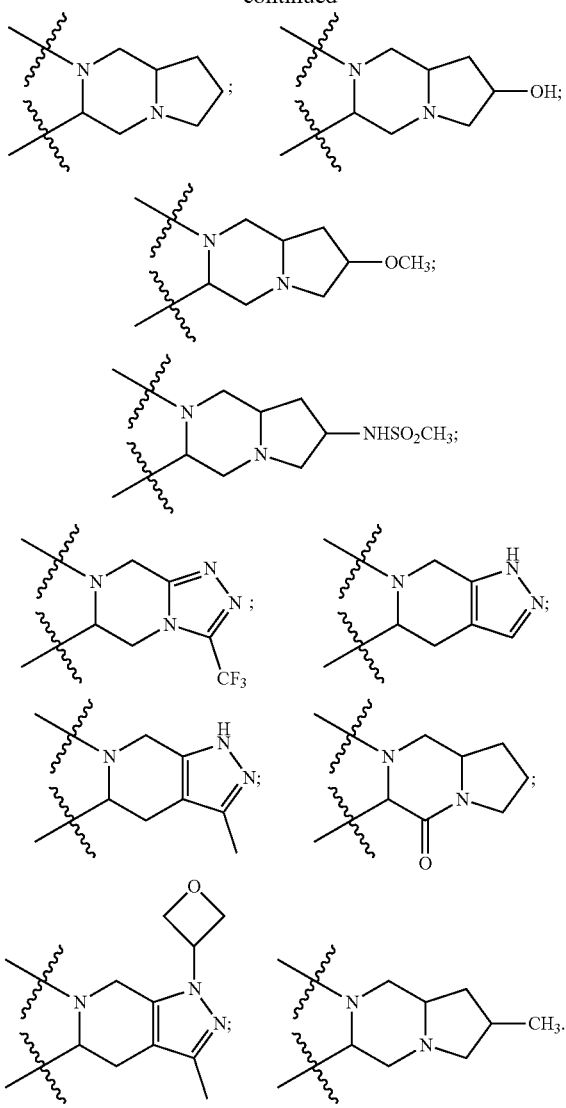

According to some embodiments of the present disclosure, the sixth ring is a piperazine ring, and the ring contains an oxo group (carbonyl), and such piperazine ring is preferably selected from, but not limited to:

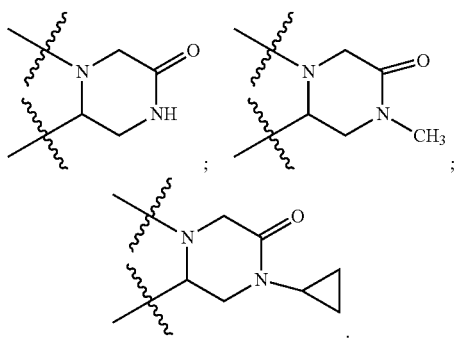

According to some embodiments of the present disclosure, the sixth ring is an unsaturated piperidine ring, and the unsaturated bond is cyclic or exocyclic, and such unsaturated piperidine ring is preferably selected from, but not limited to:

According to some preferable embodiments of the present disclosure, $R_6$ is selected from:

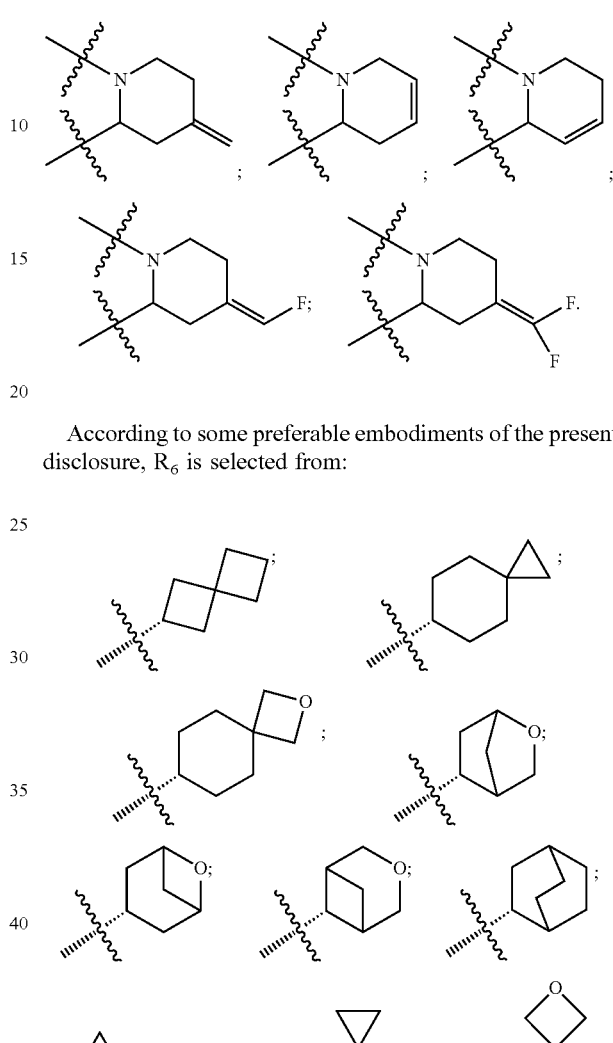

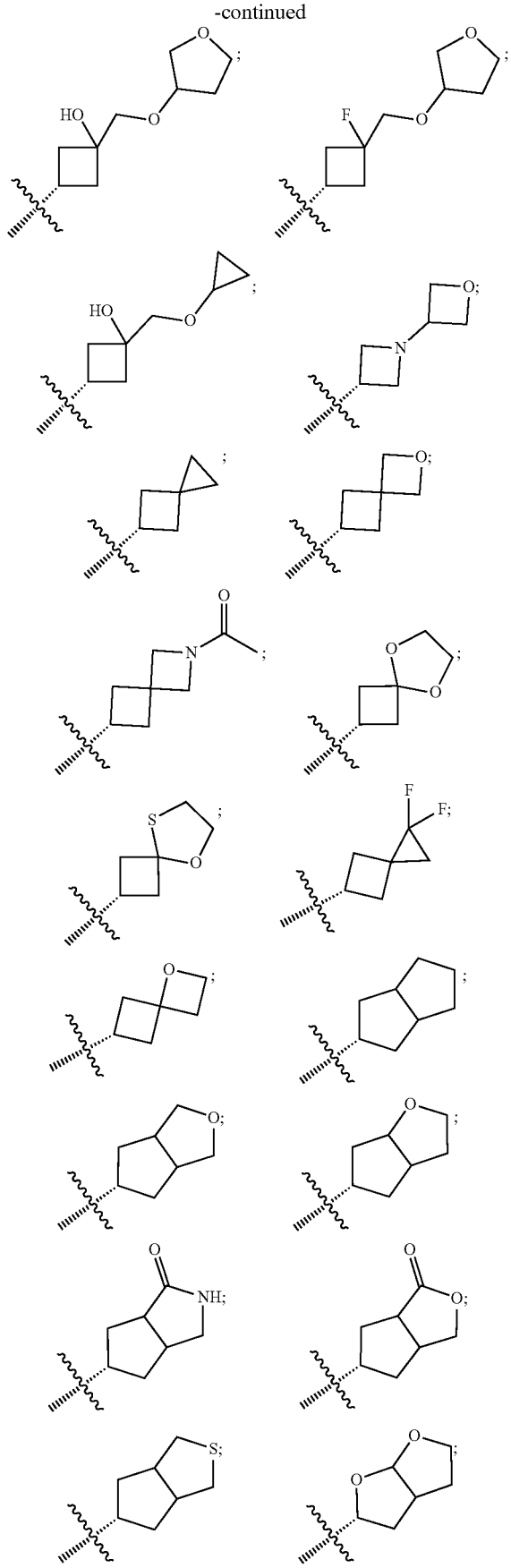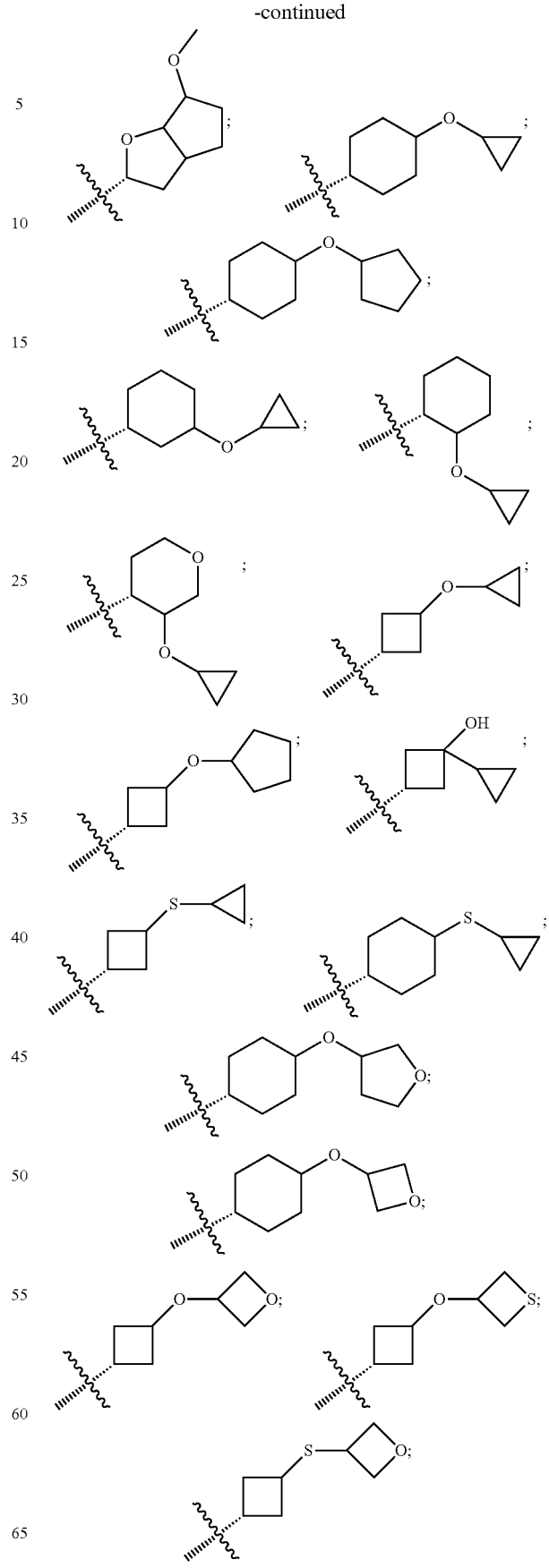

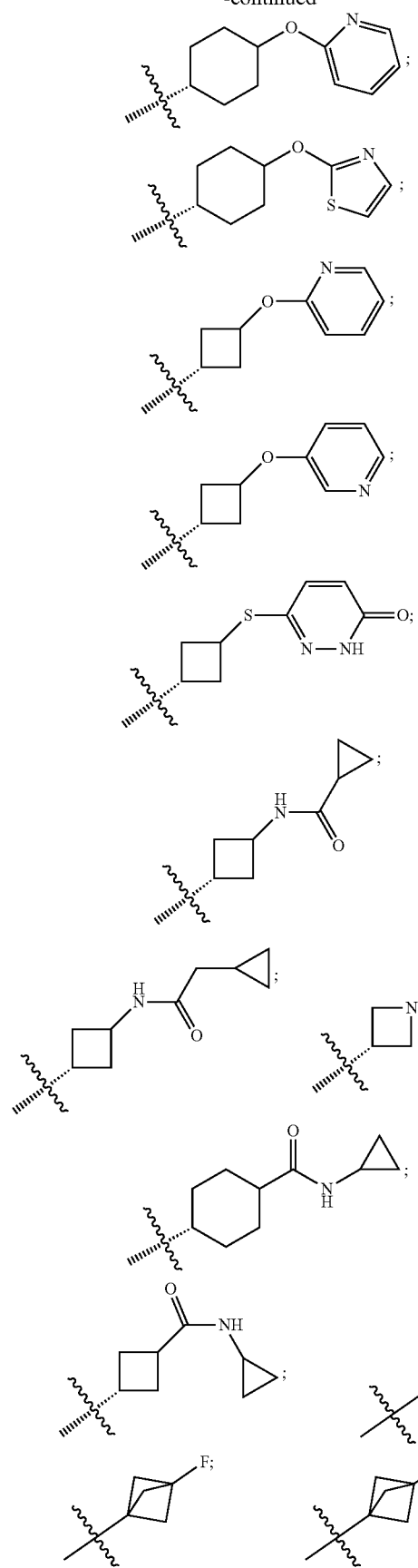
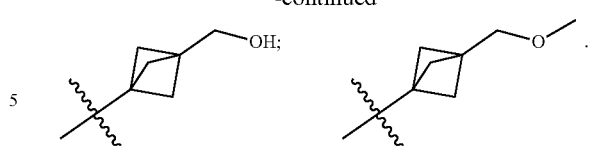
According to some embodiments of the present disclosure, the sixth ring is a morpholine ring, and the compounds of Formula (I) specifically refer to the following four compounds:
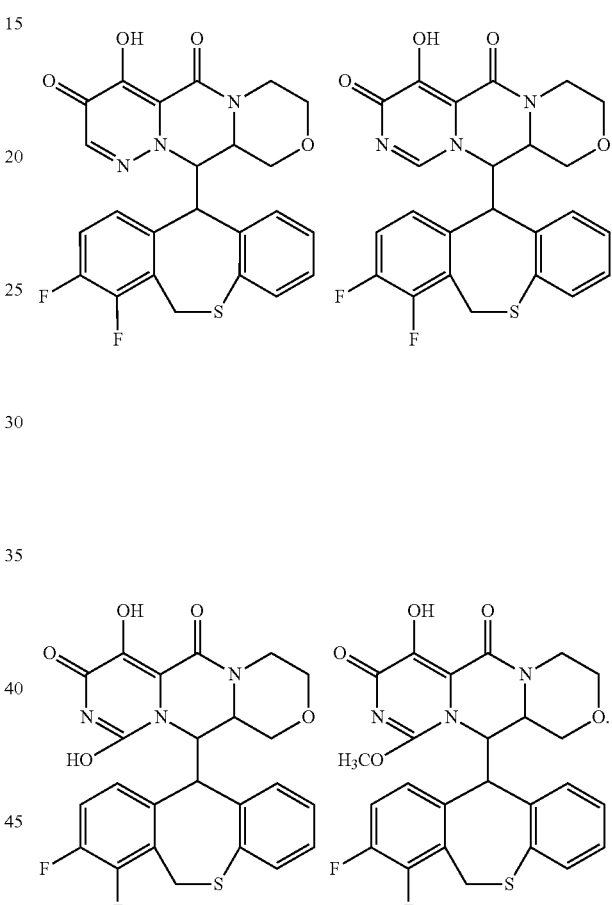
According to the present disclosure, the pyridone derivative is preferably selected from the following compounds:
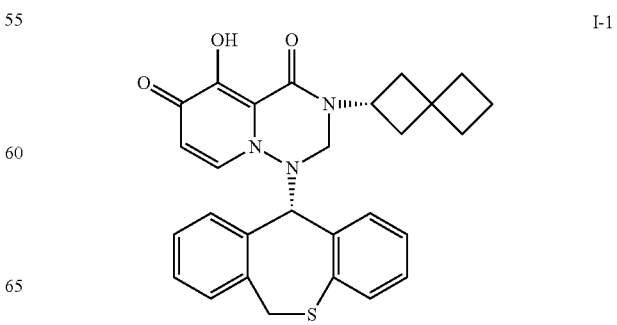
I-1

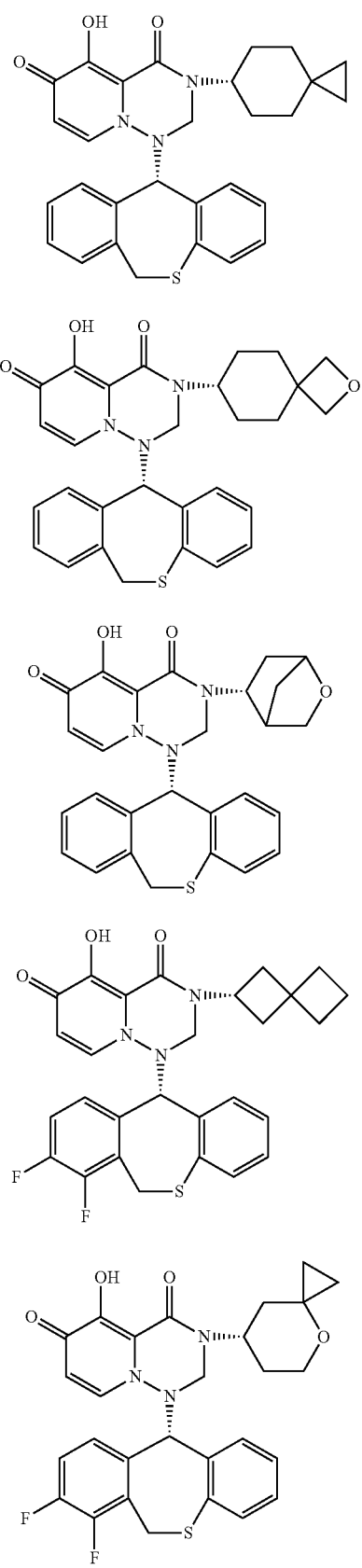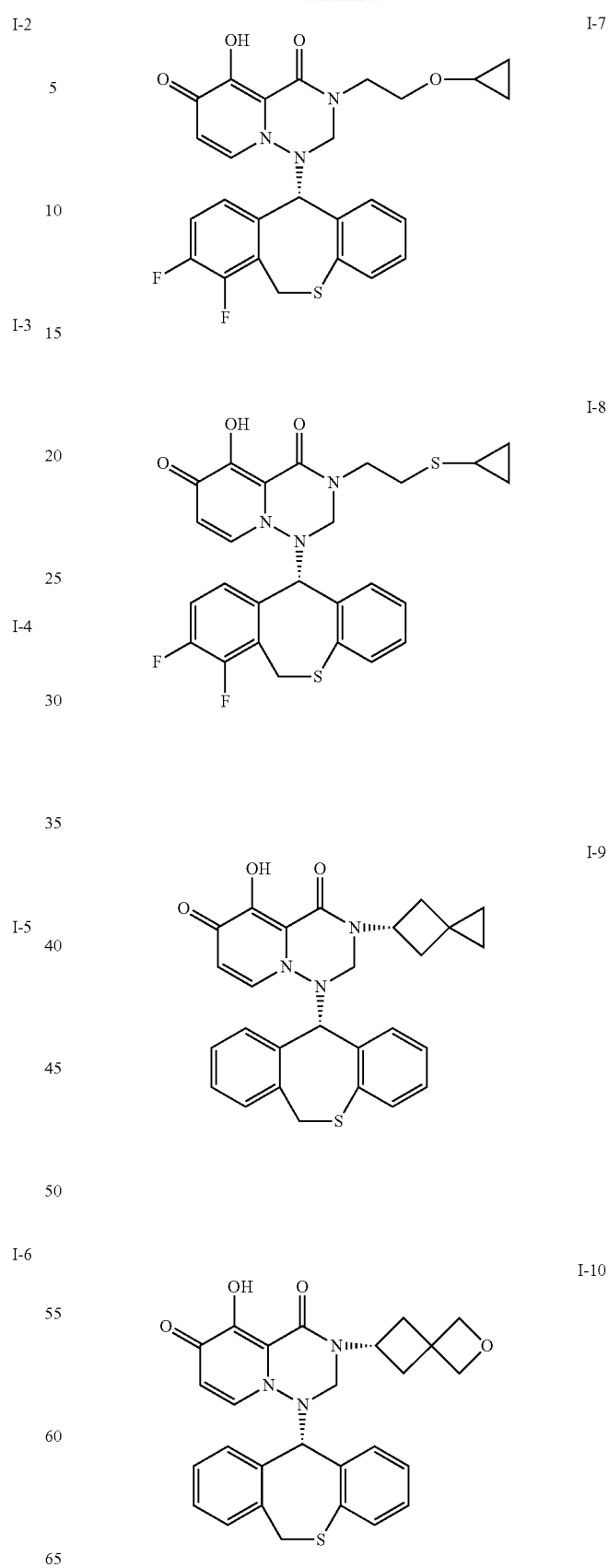

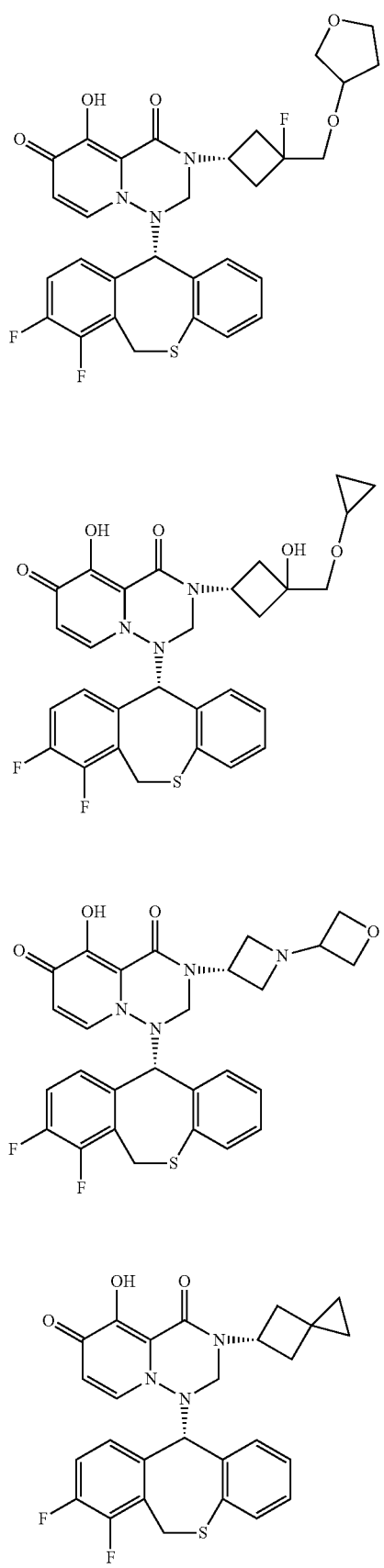
I-11
I-12
I-13
I-14
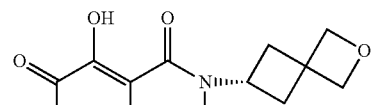
I-15
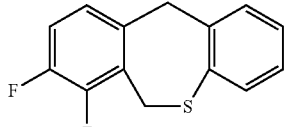
I-16
I-17
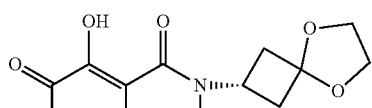
I-18
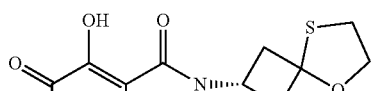
I-19

I-20
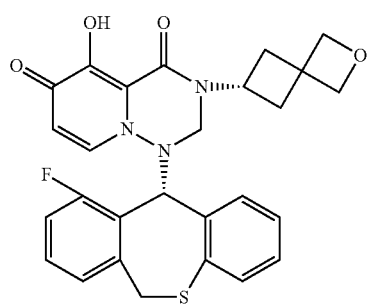
I-21
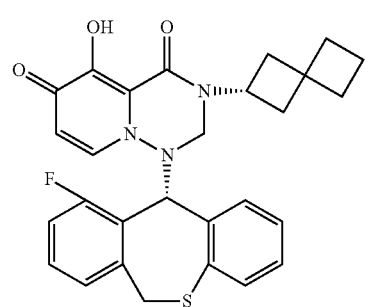
I-22
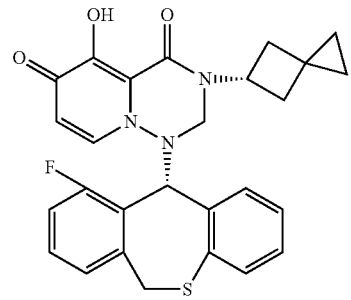
I-23
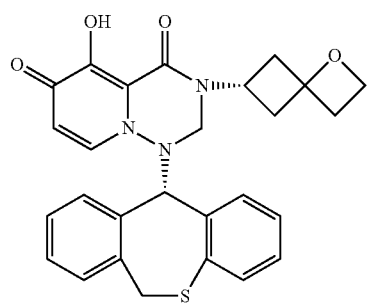
I-24
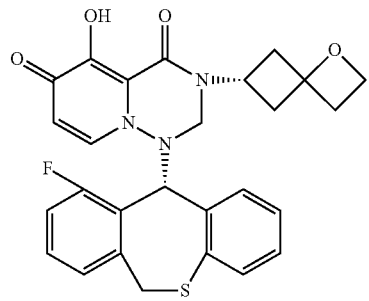
I-25
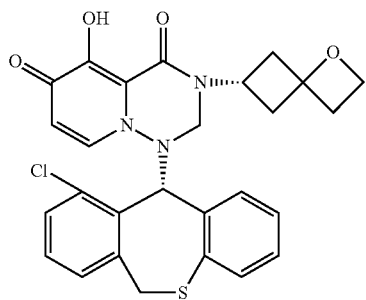
I-26
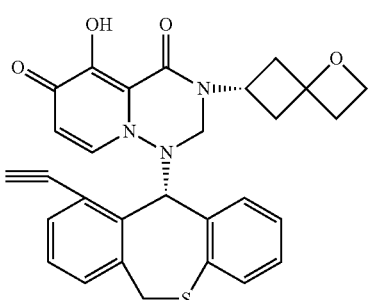
I-27
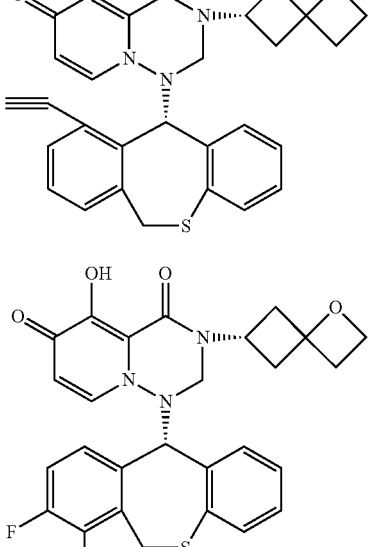
I-28
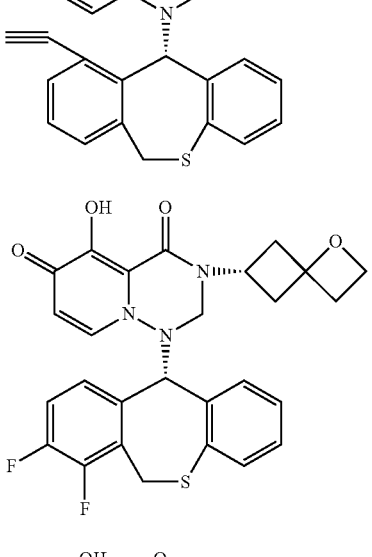
I-29
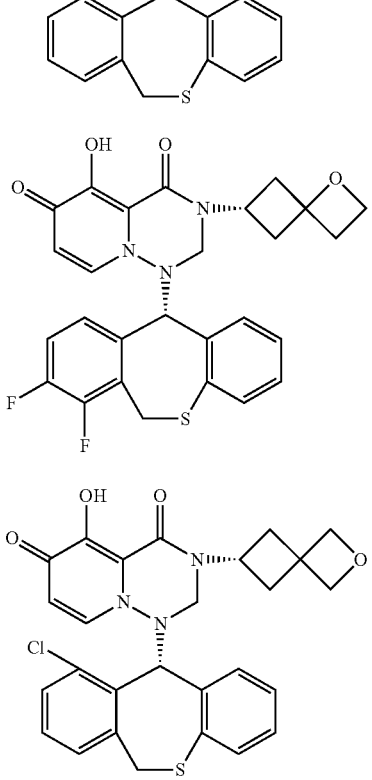

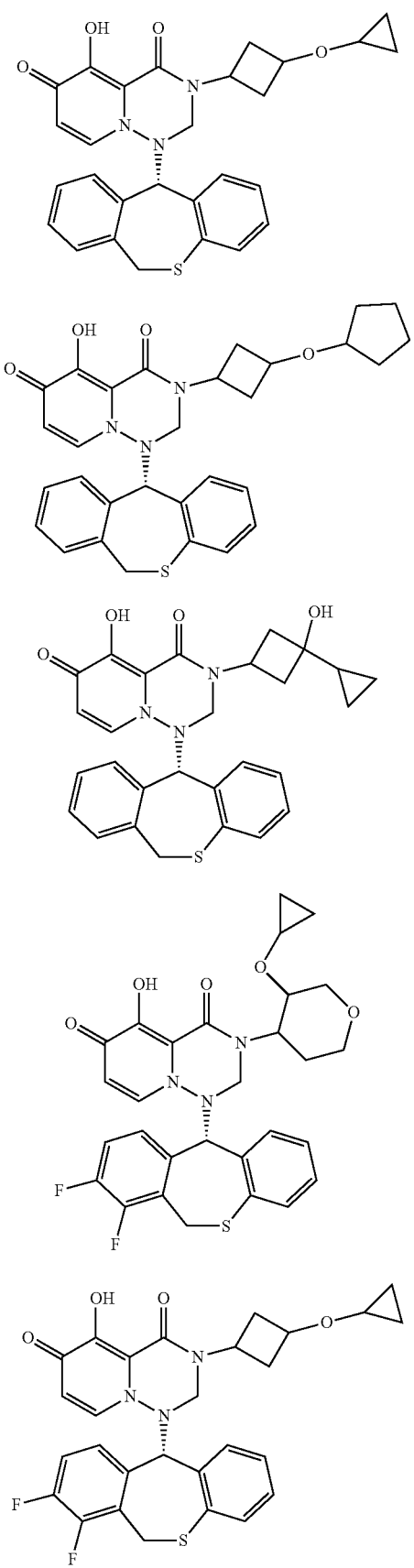
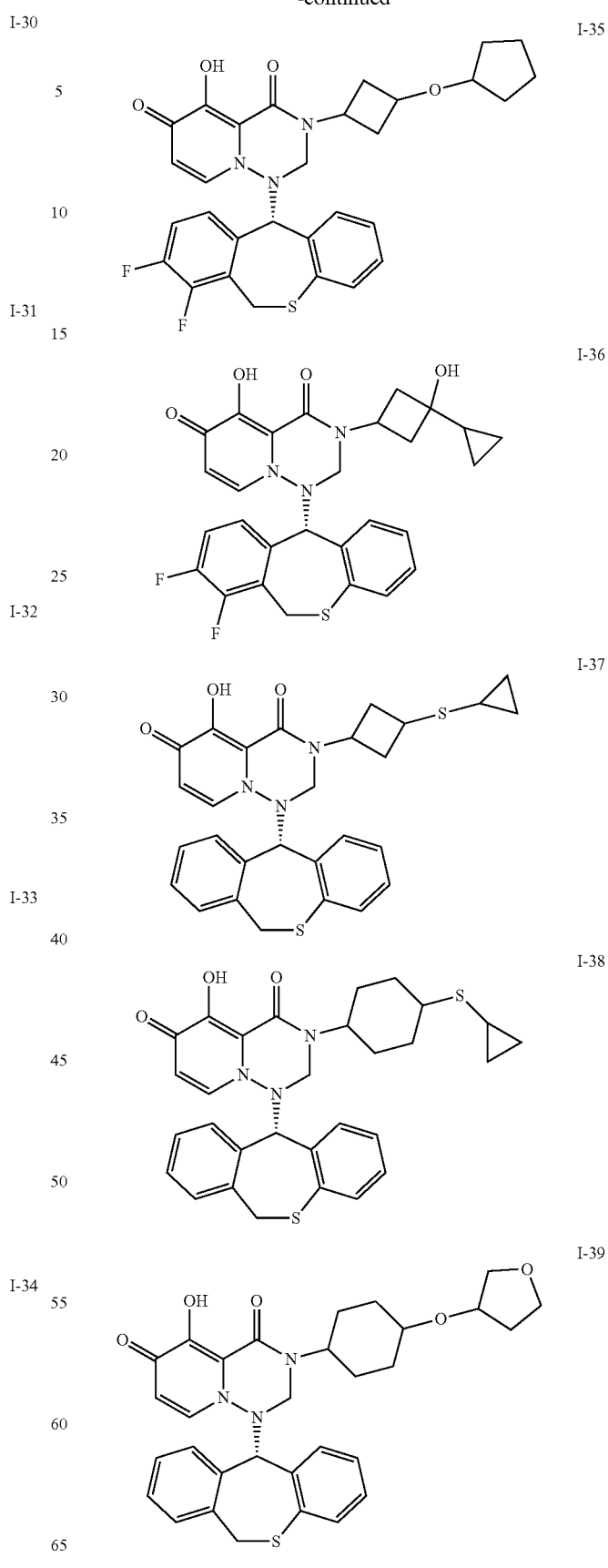

I-40 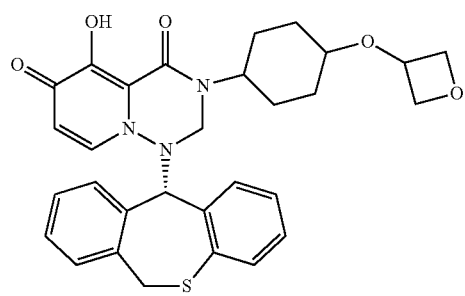
I-45 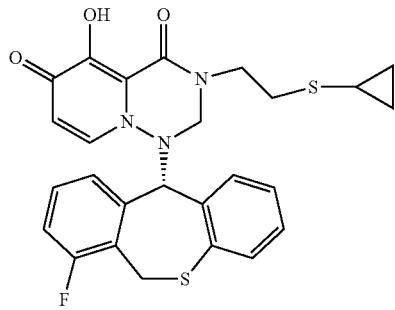
I-41 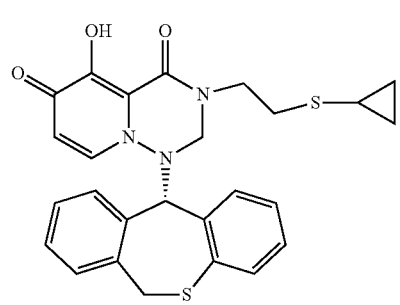
I-46 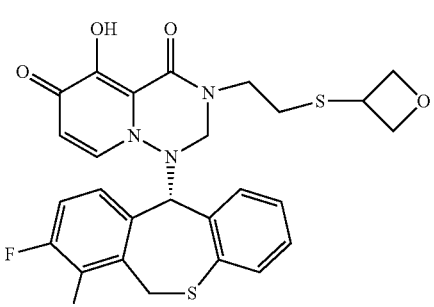
I-42 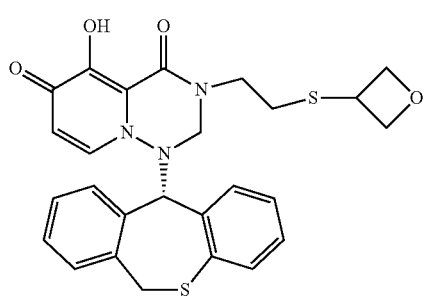
I-47 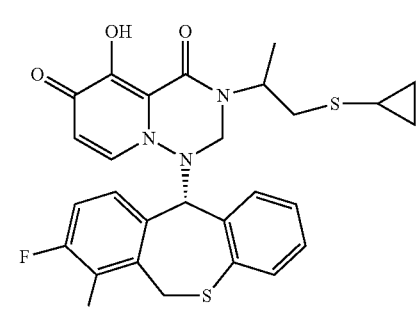
I-43 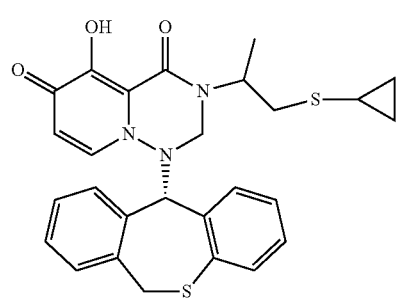
I-48 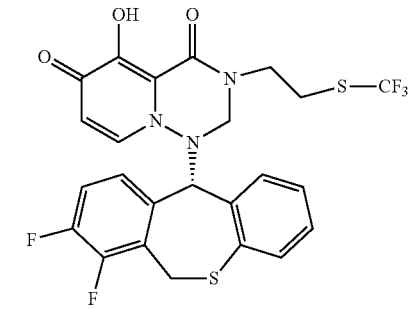
I-44 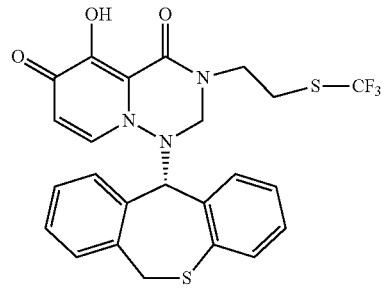
I-49 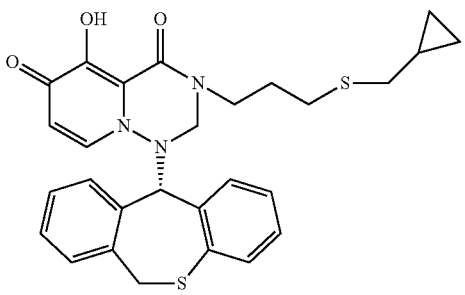

I-50
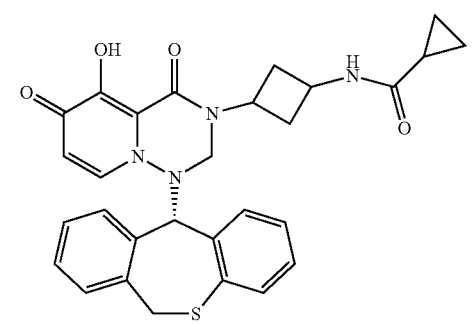
I-51
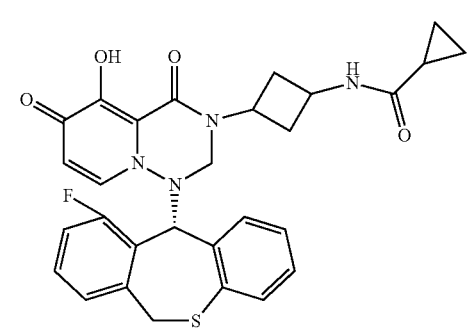
I-52
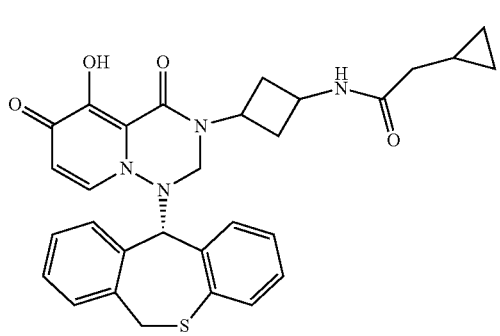
I-53
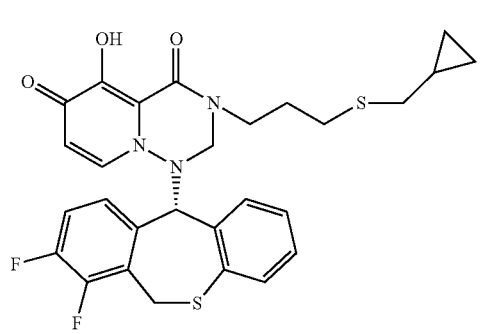
I-54
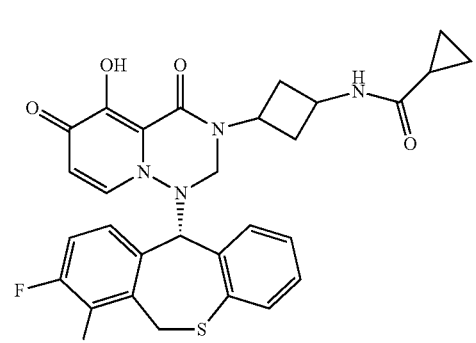
I-55
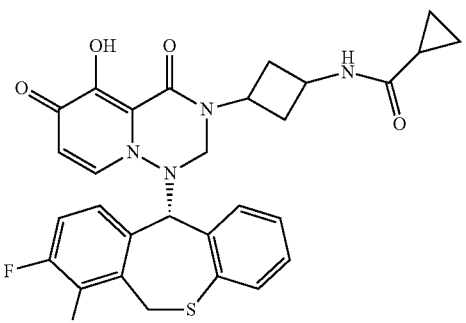
I-56
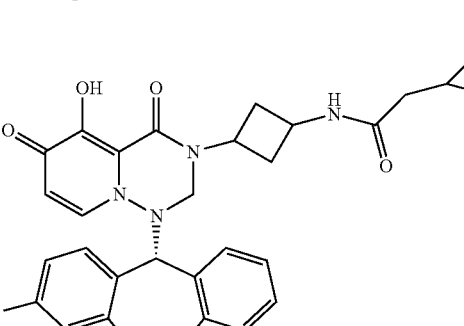
I-57
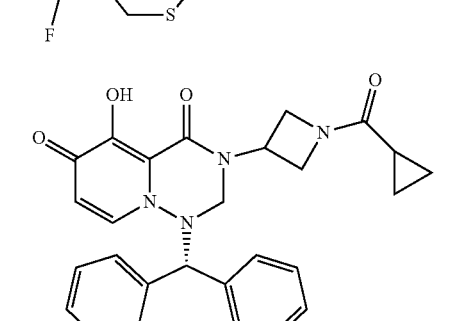
I-58
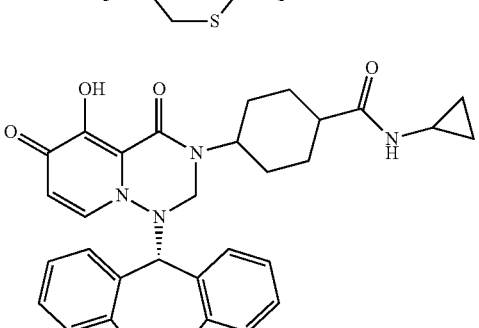
I-59
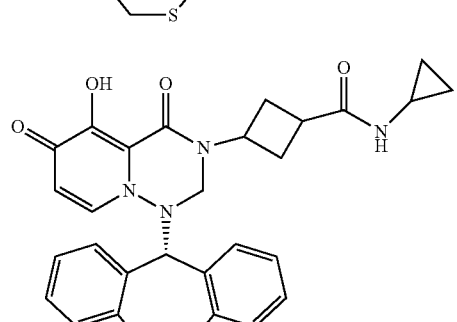

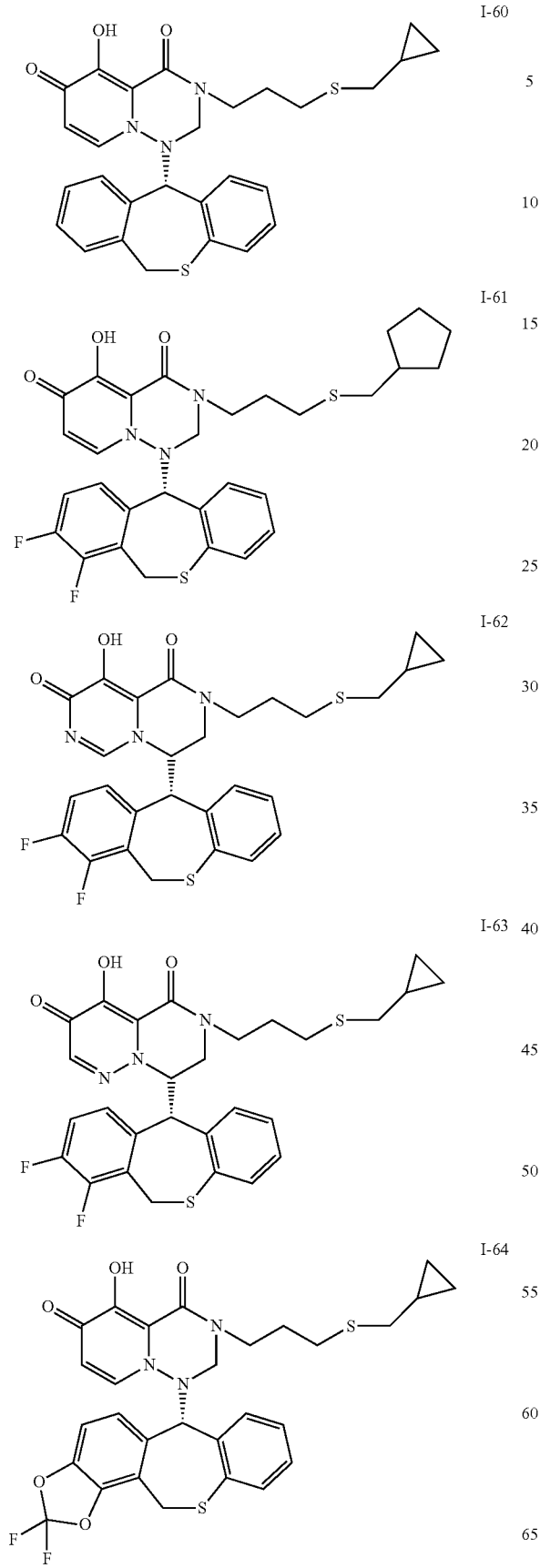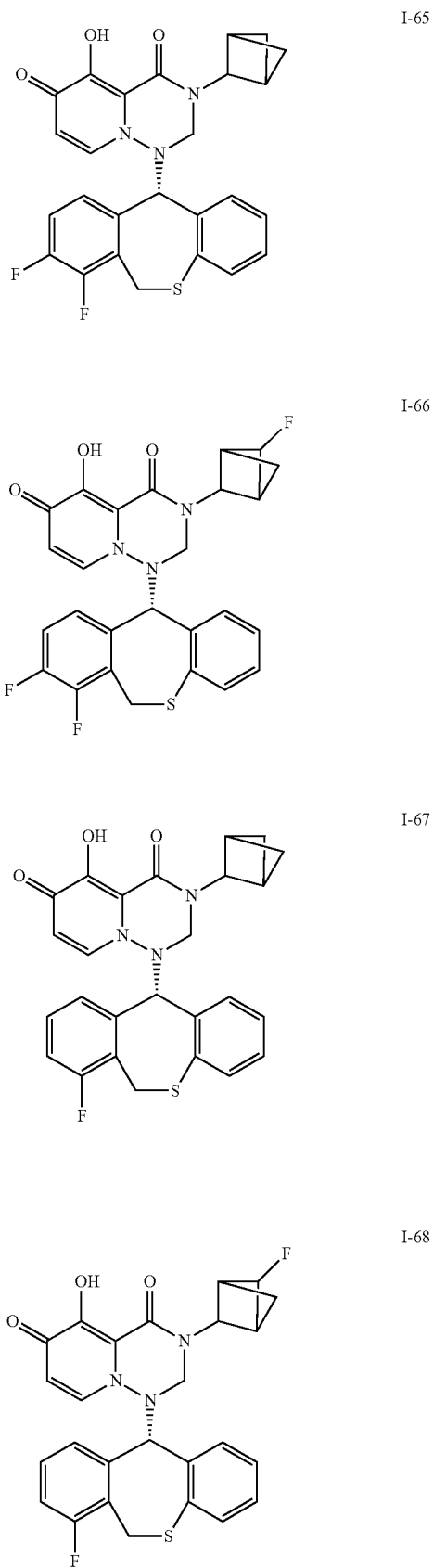

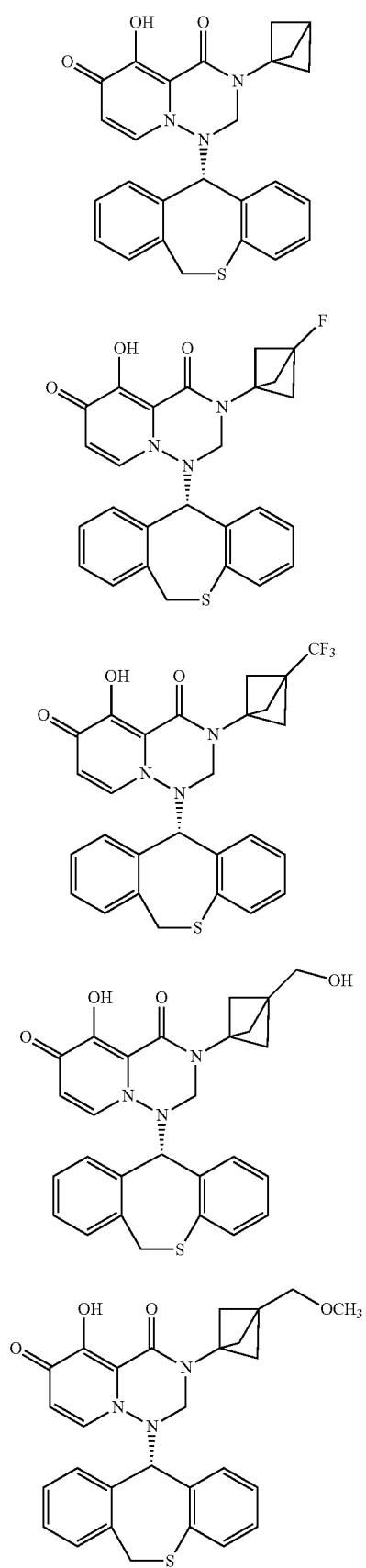
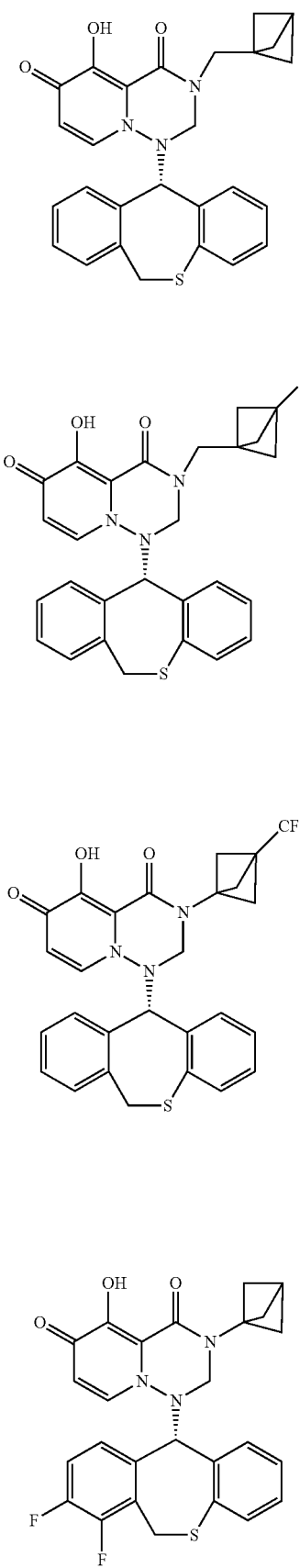

I-78 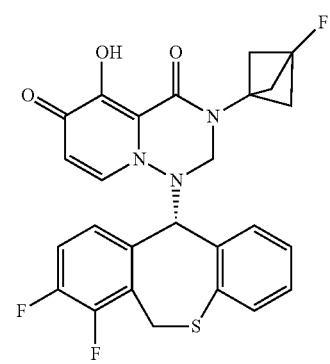
I-79 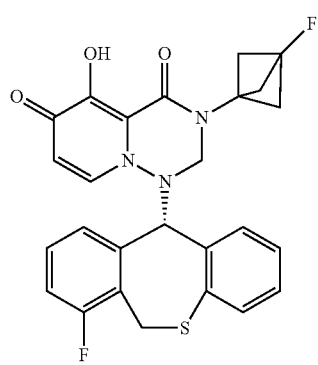
I-80 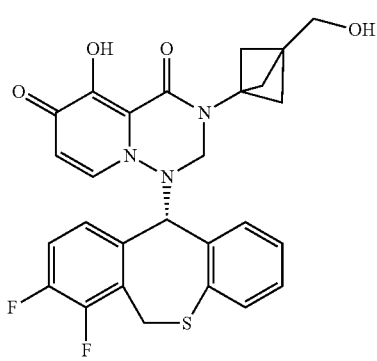
I-81 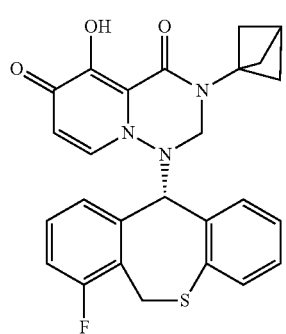
I-82
I-83
I-84
I-85
I-86

-continued
I-87
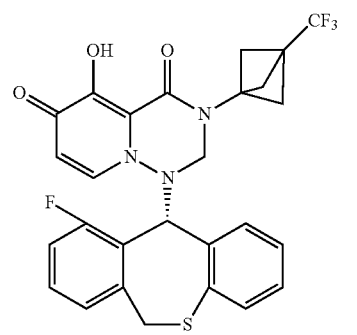
I-88
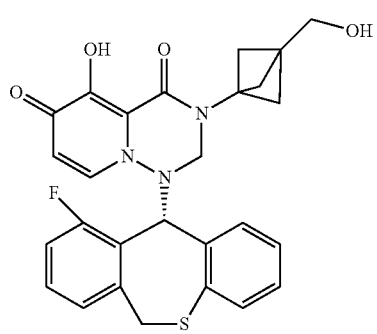
I-89
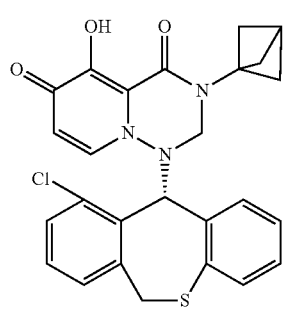
I-90
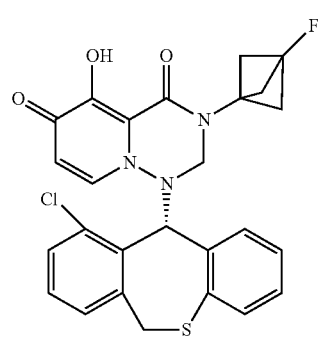
I-91
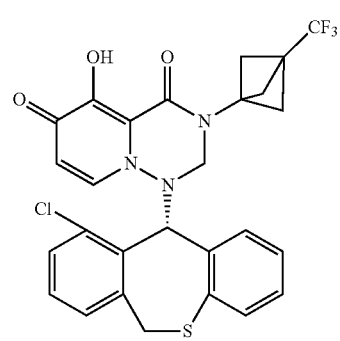
-continued
I-92
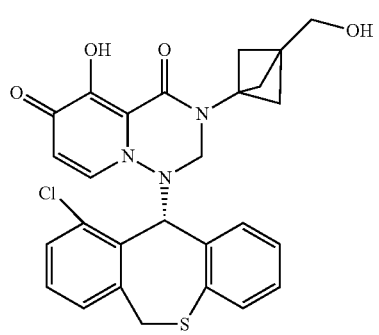
I-93
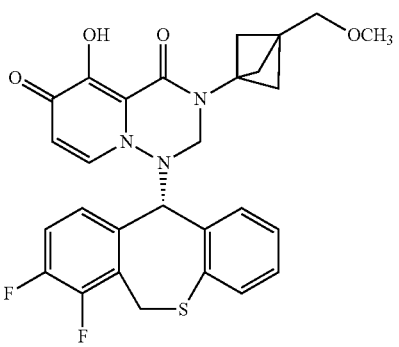
I-94
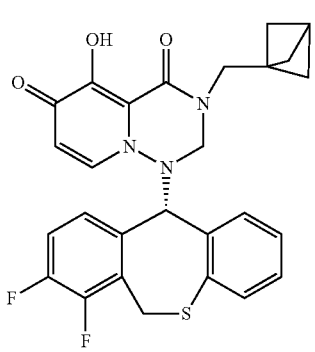
I-95
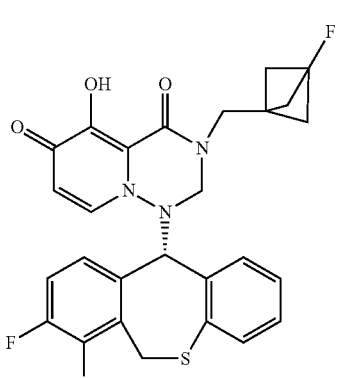

I-96
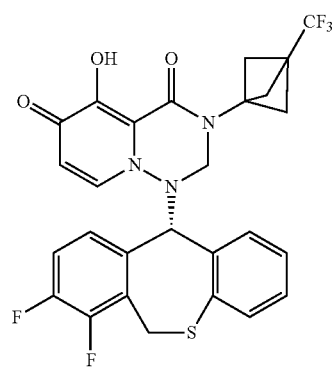
II-1
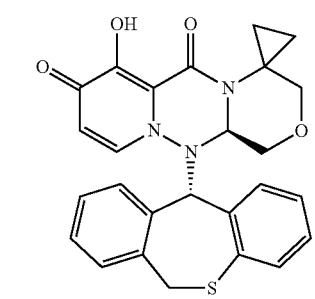
II-2
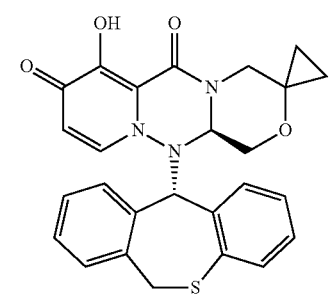
II-3
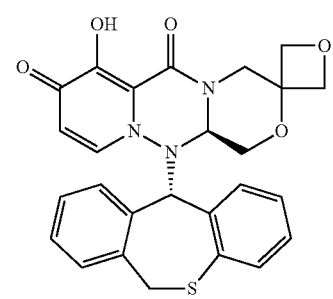
II-4
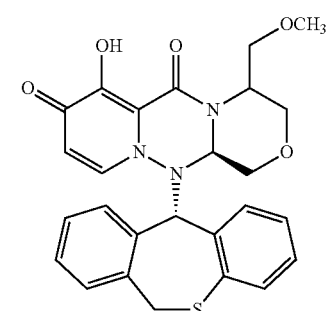
II-5
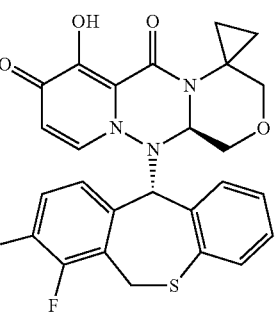
II-6
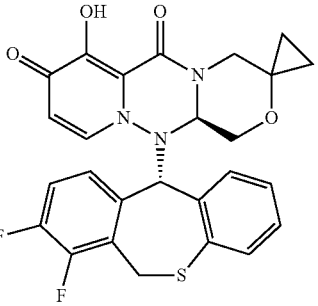
II-7
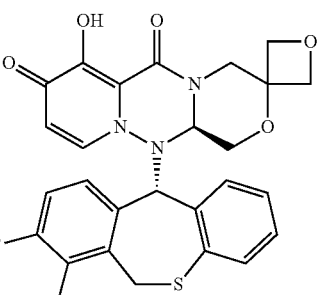
II-8
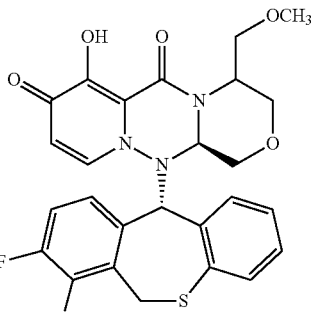
II-9
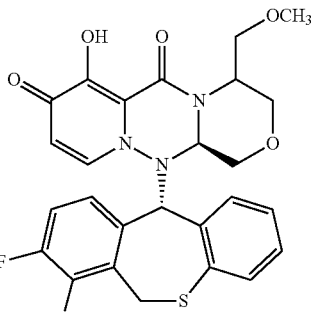

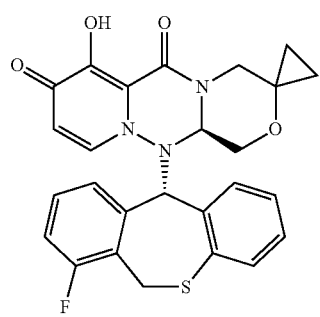
II-10
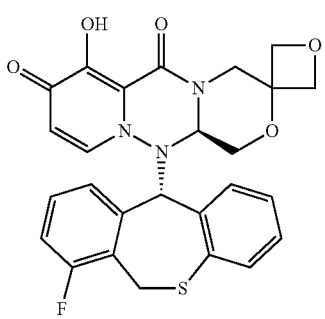
II-11
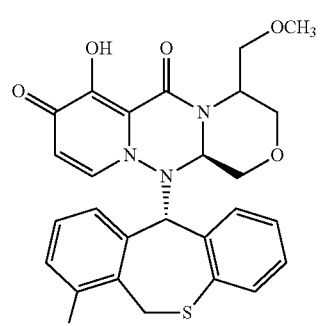
II-12
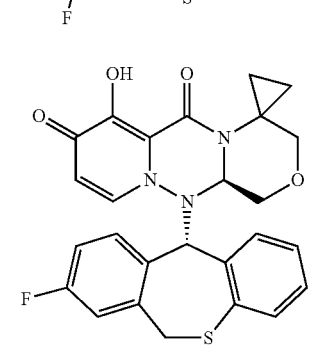
II-13
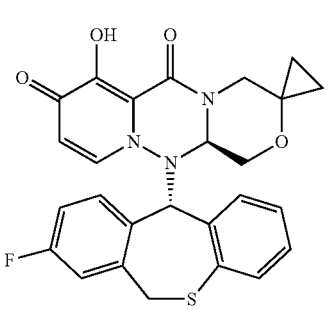
II-14
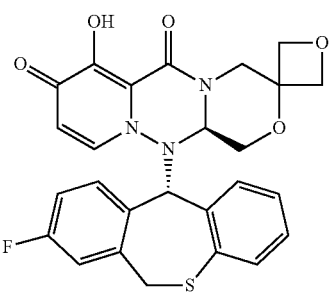
II-15
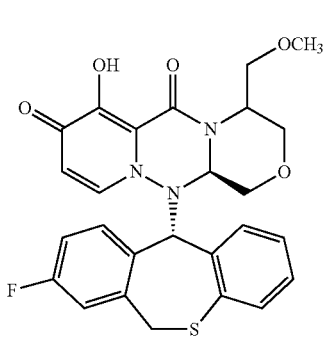
II-16
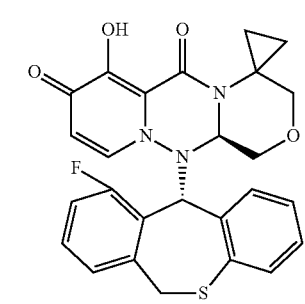
II-17
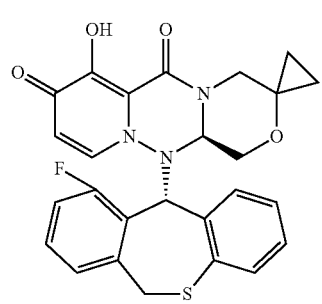
II-18
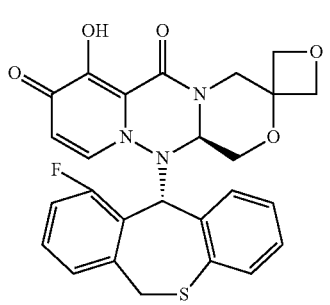
II-19

-continued
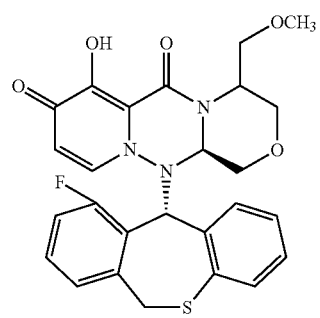
II-20
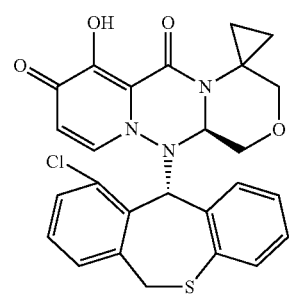
II-21
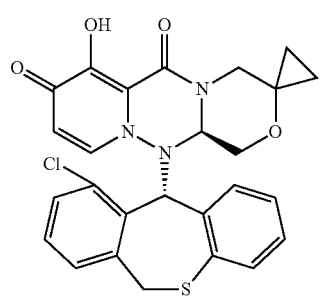
II-22
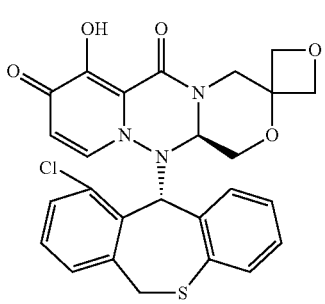
II-23
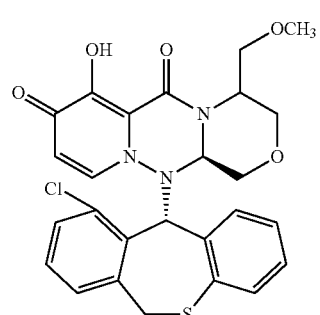
II-24
-continued
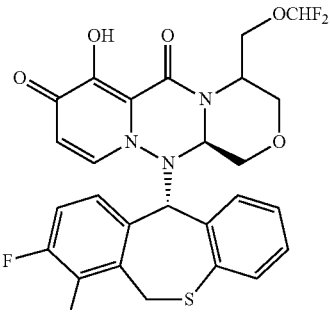
II-25
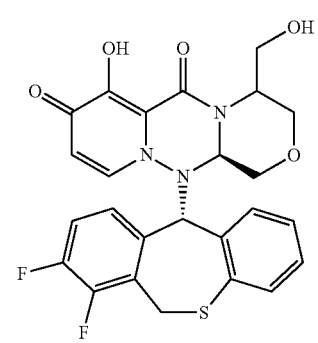
II-26
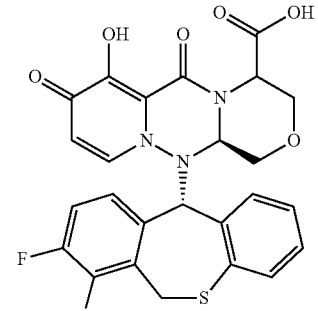
II-27
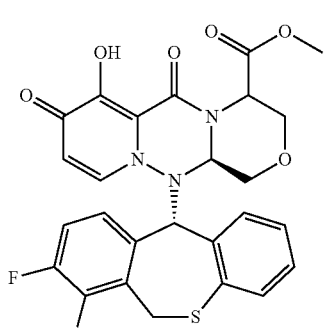
II-28
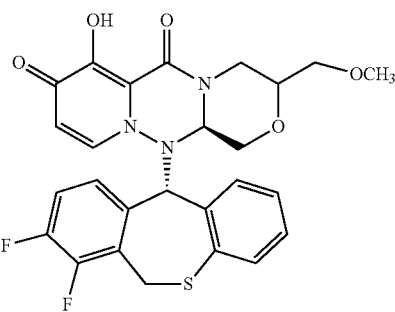
II-29

II-30
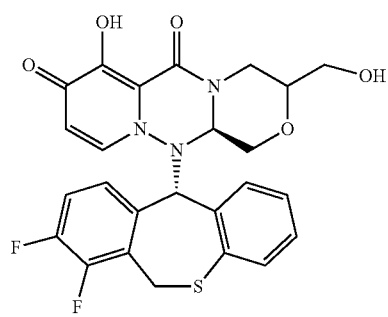
II-31
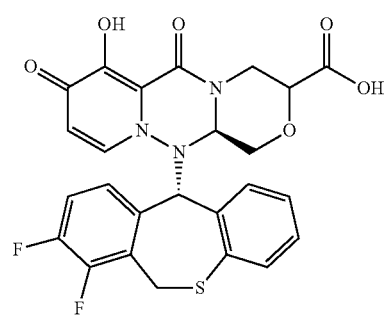
II-32
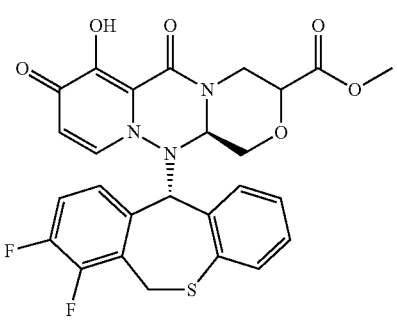
II-33
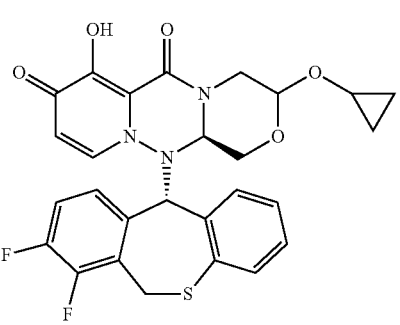
II-34
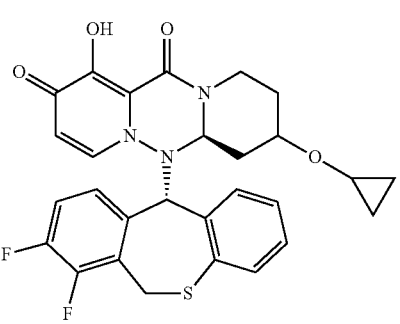
II-35
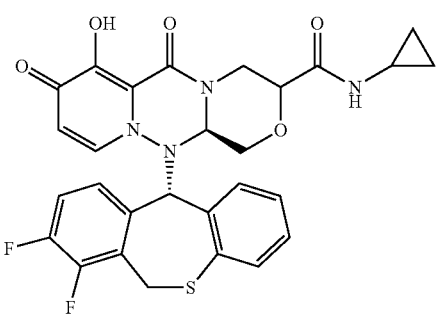
II-36
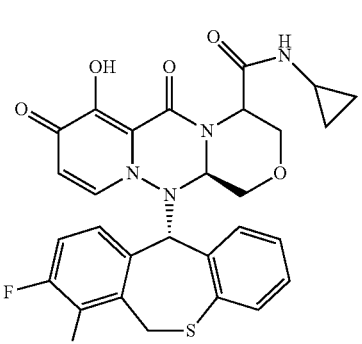
II-37
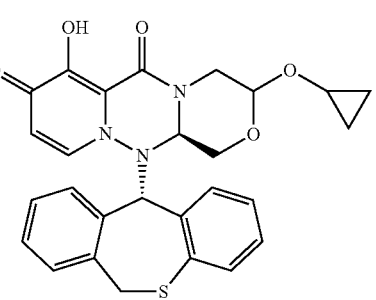
II-38
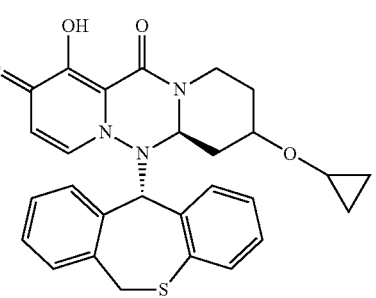
II-39
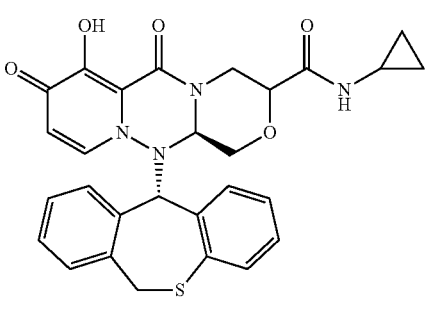

II-40
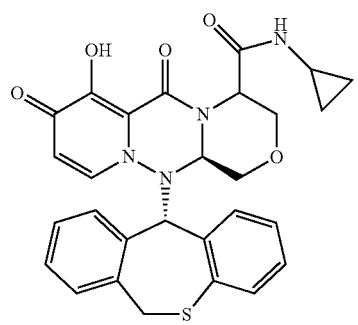
II-41
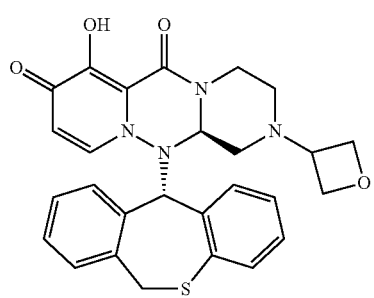
II-42
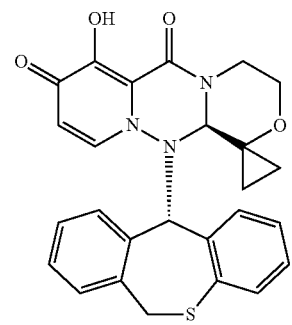
II-43
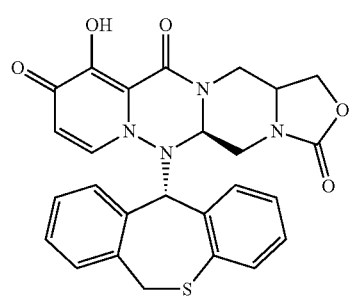
II-44
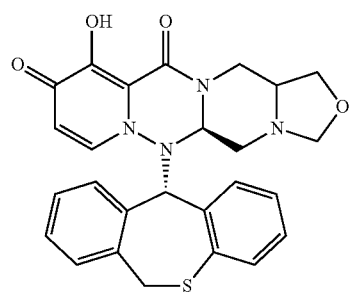
II-45
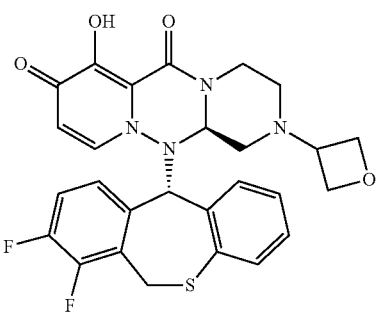
II-46
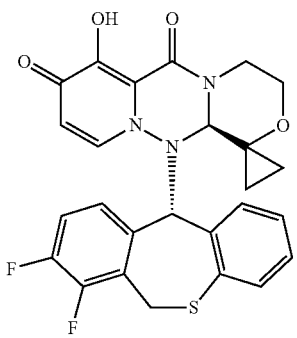
II-47
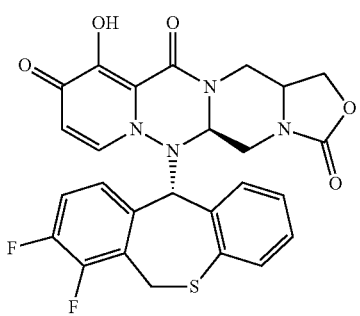
II-48
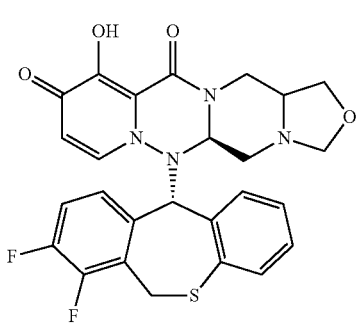
II-49
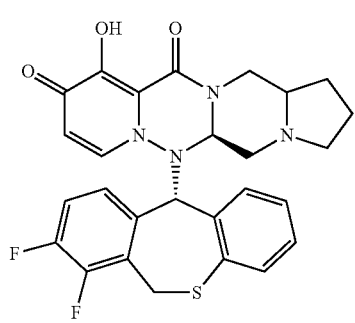

II-50
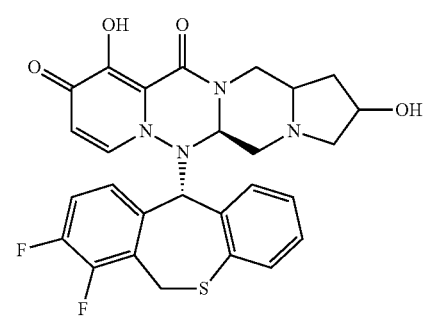
II-51
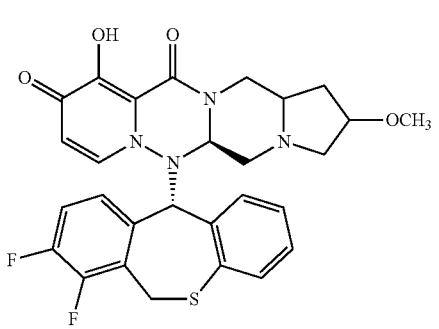
II-52
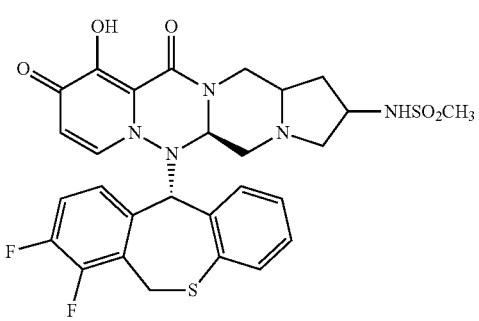
II-53
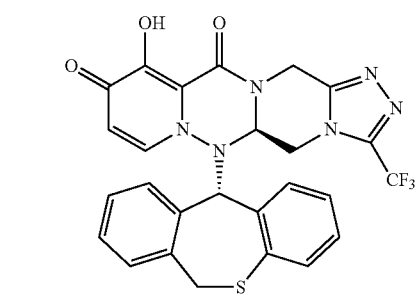
II-54
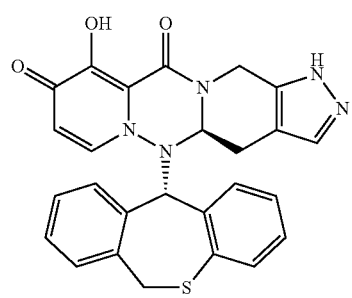
II-55
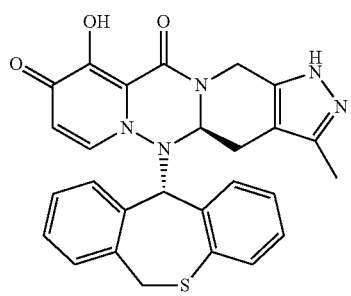
II-56
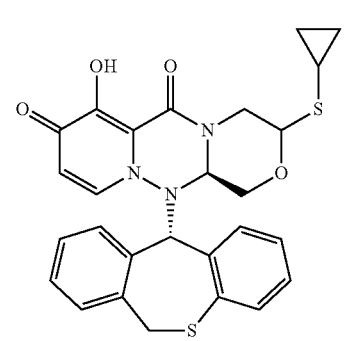
II-57
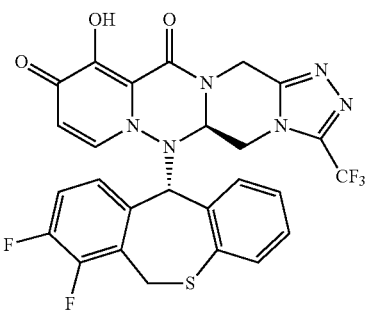
II-58
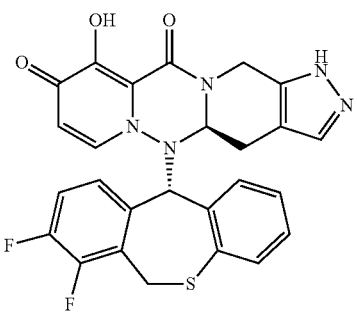
II-59
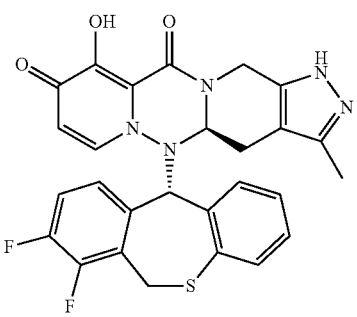

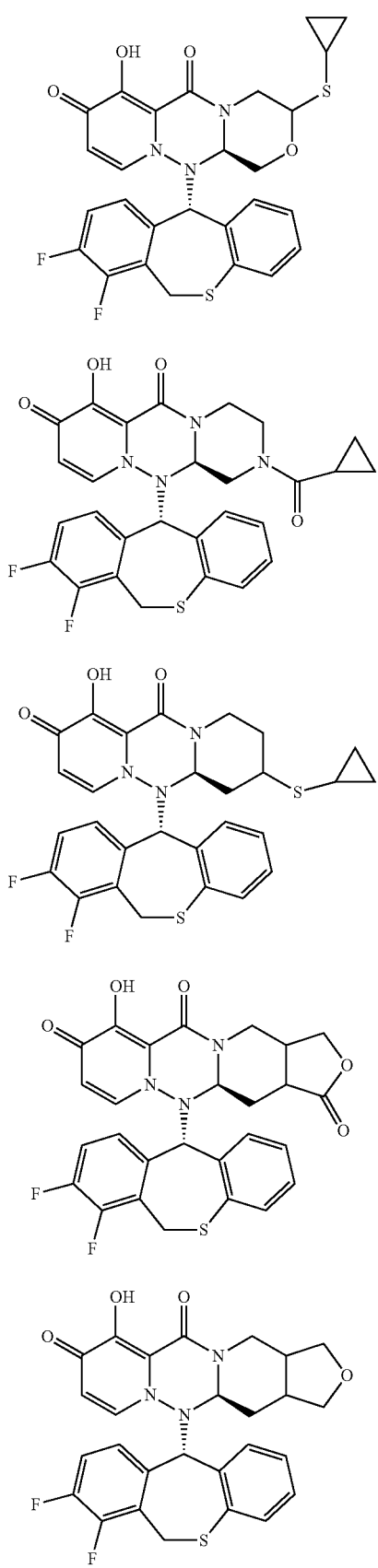
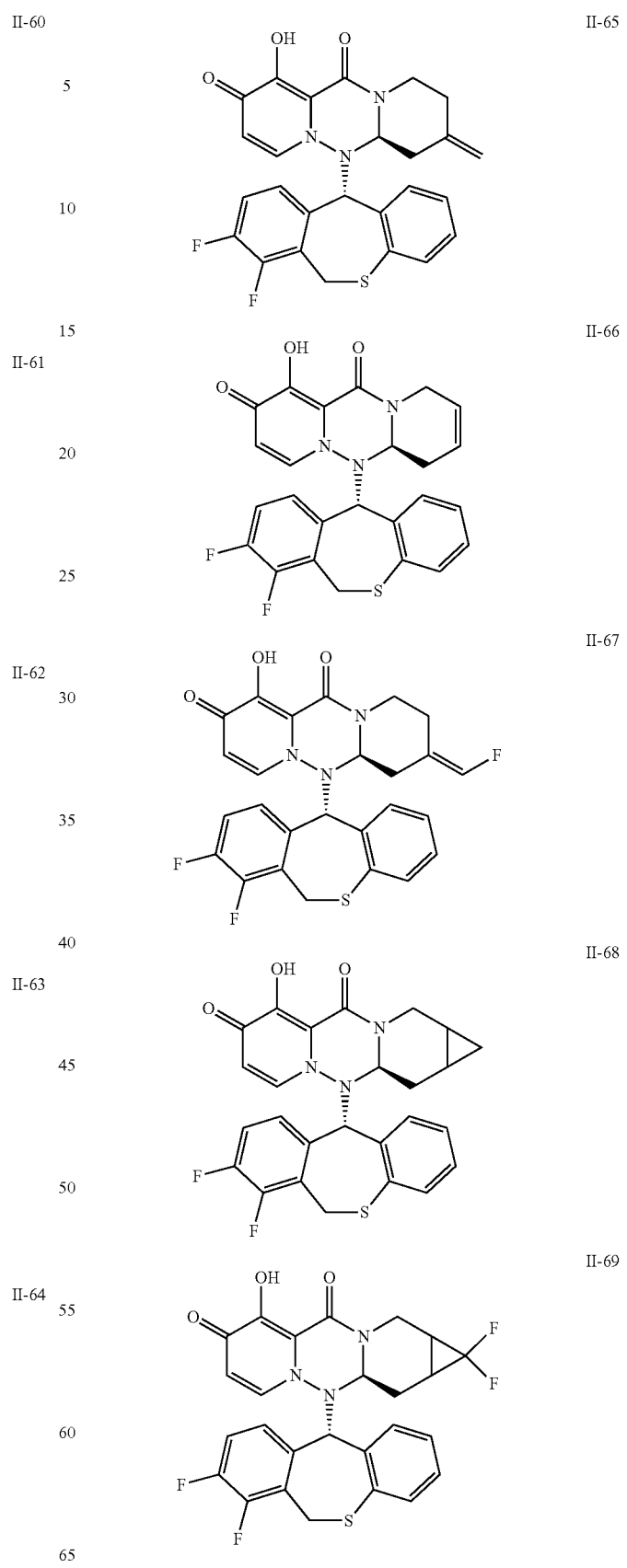

II-70
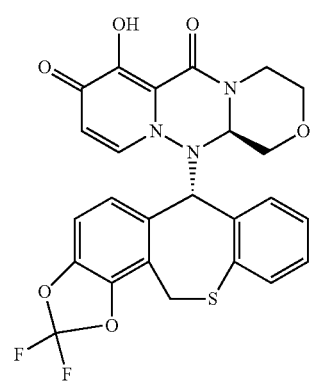
II-71
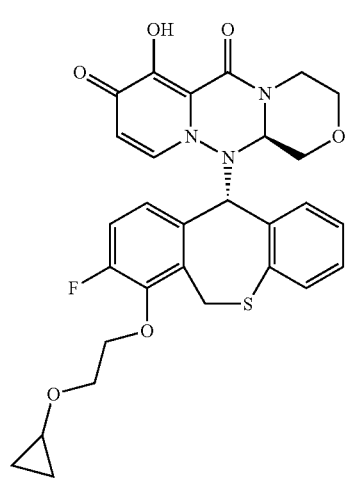
II-72
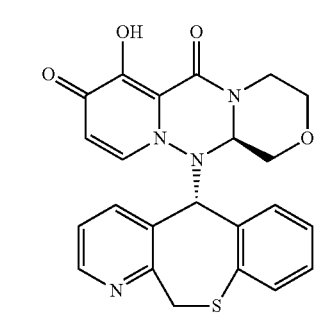
II-73
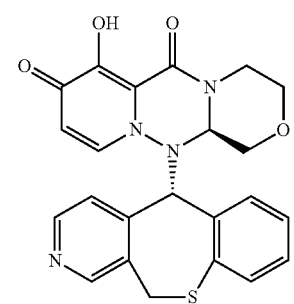
II-74
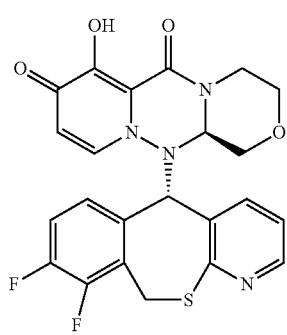
II-75
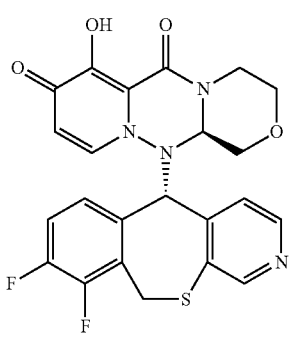
II-76
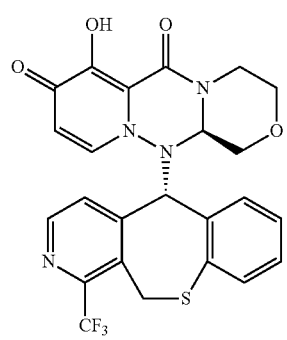
II-77
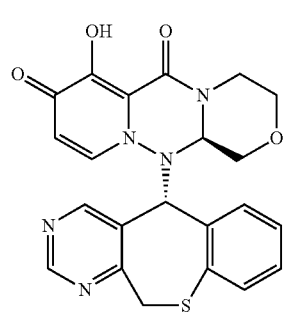
II-78
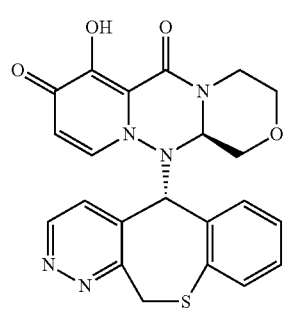

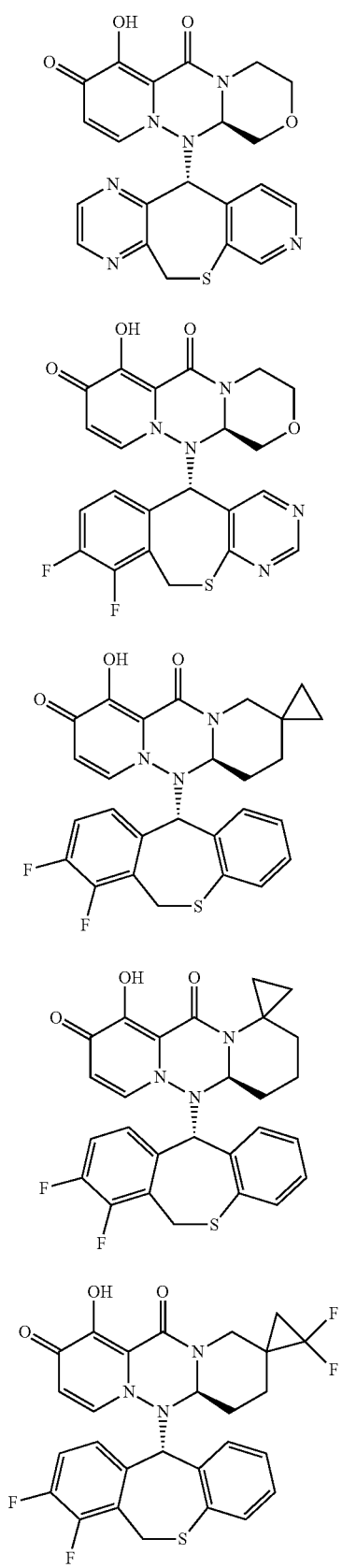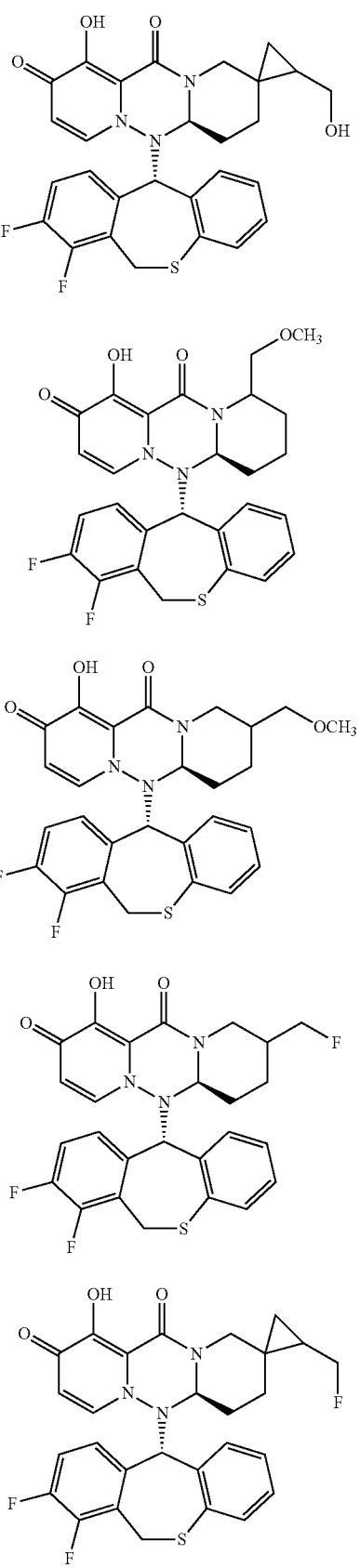

II-89 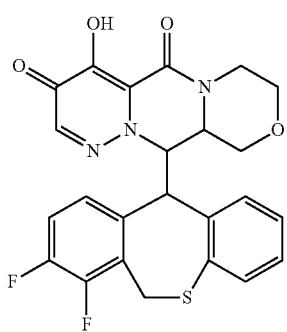
II-90 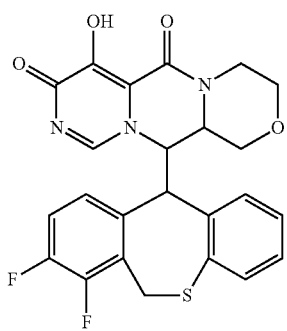
II-91 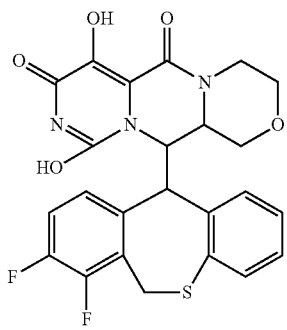
II-92 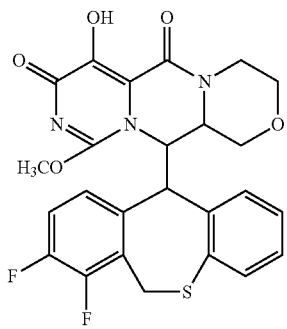
II-93 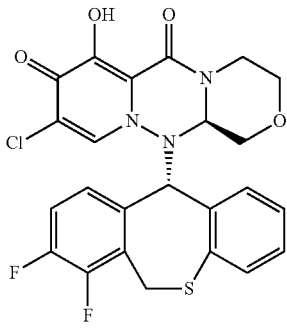
II-94 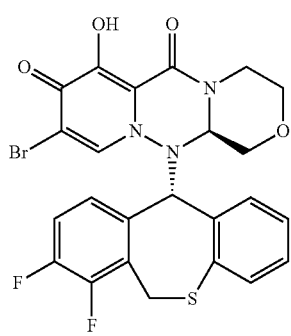
II-95 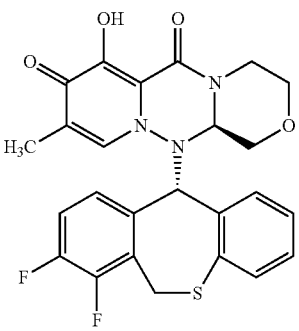
II-96 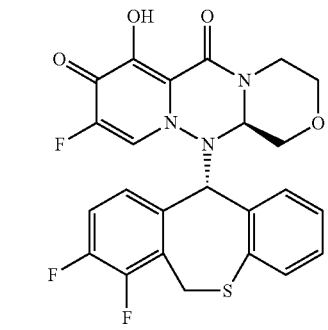
II-97 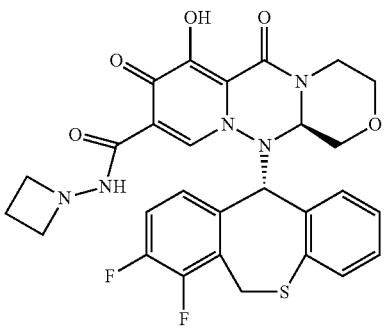
II-98 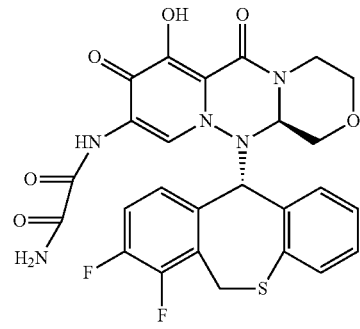

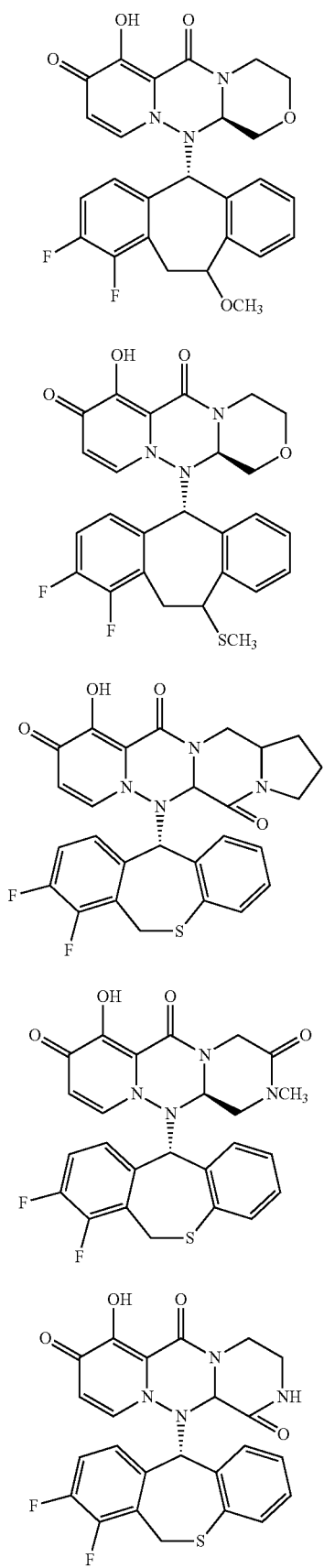
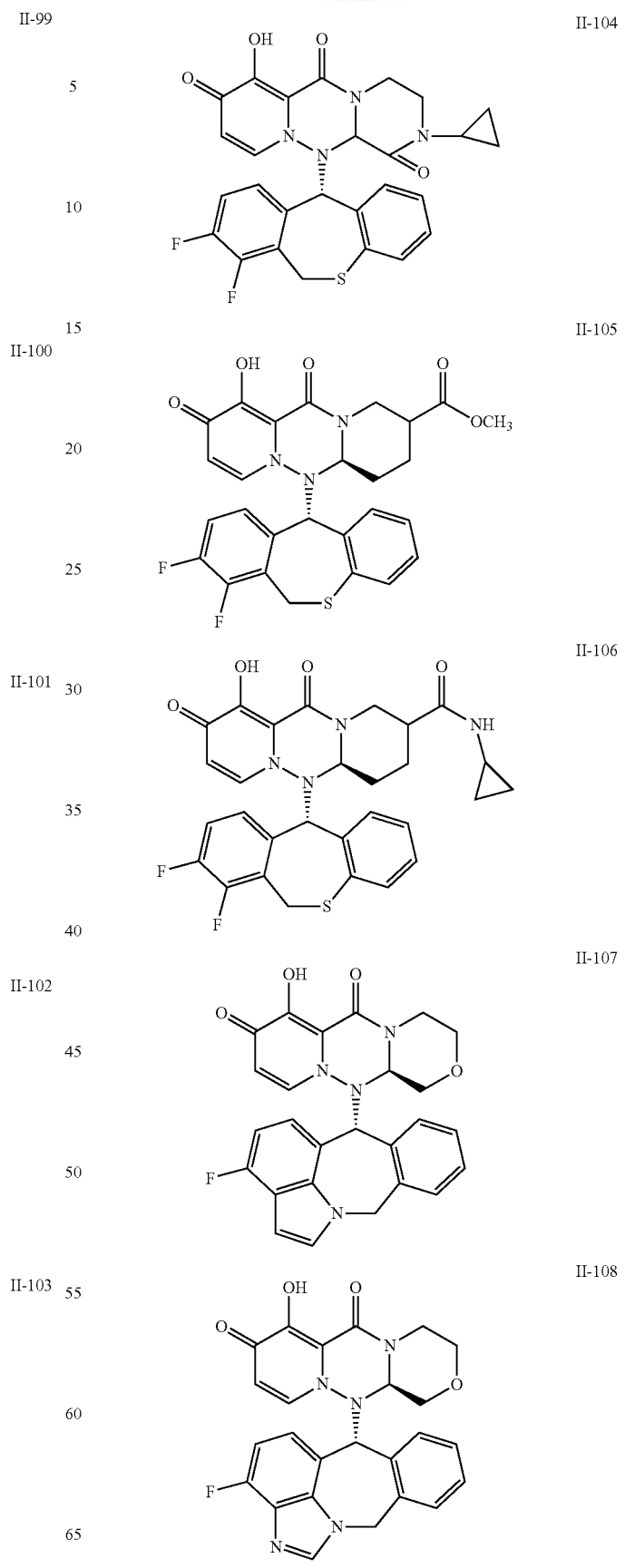

-continued
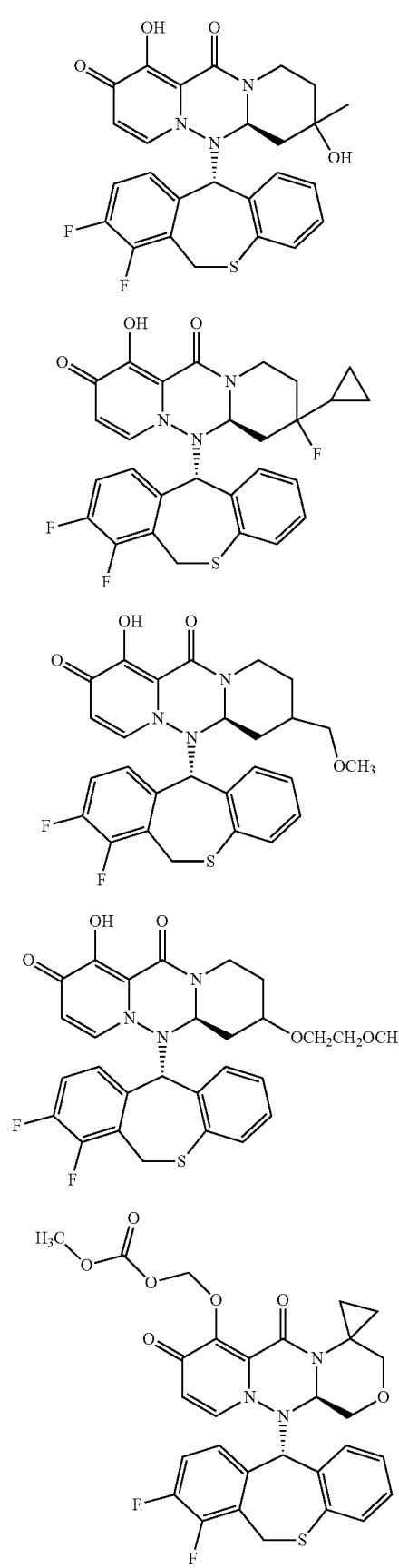
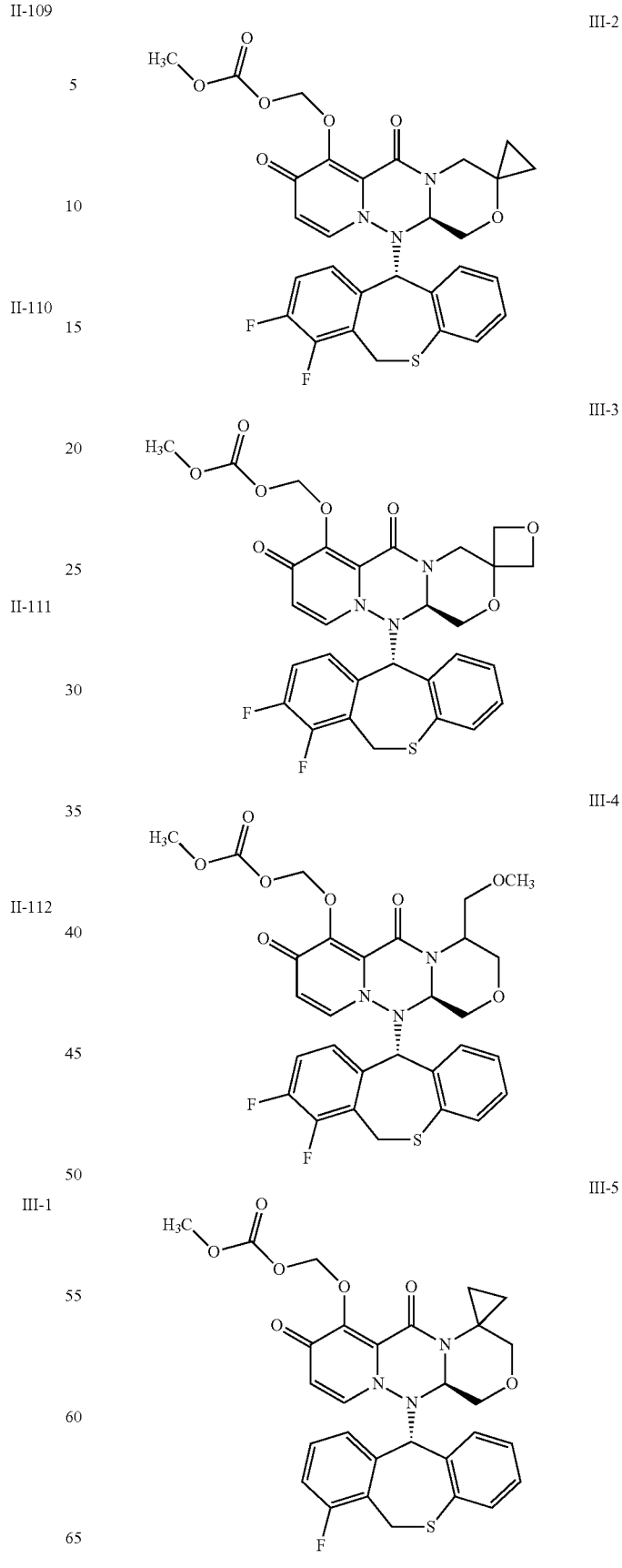

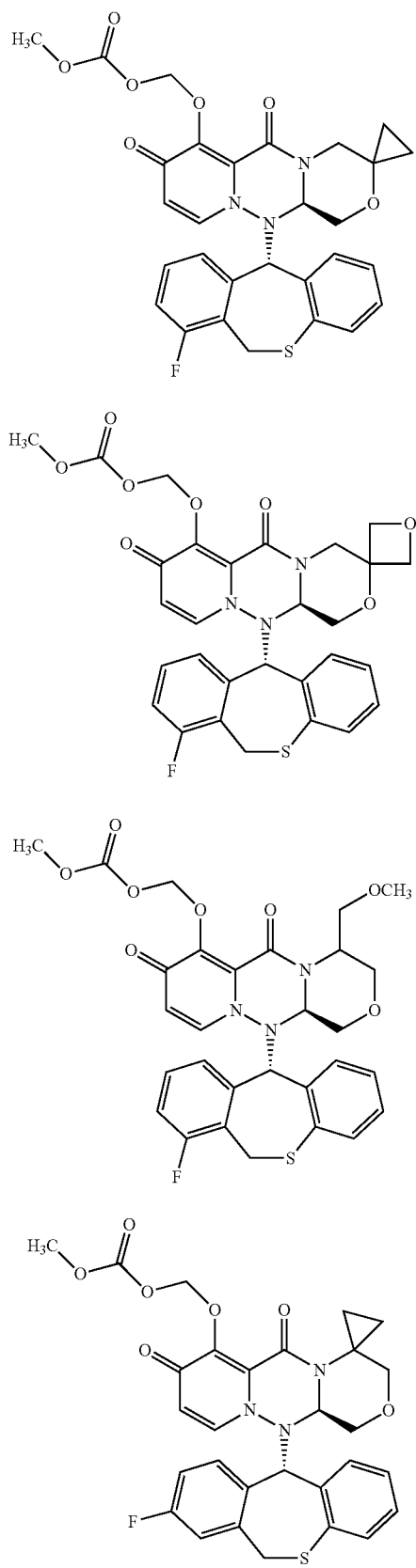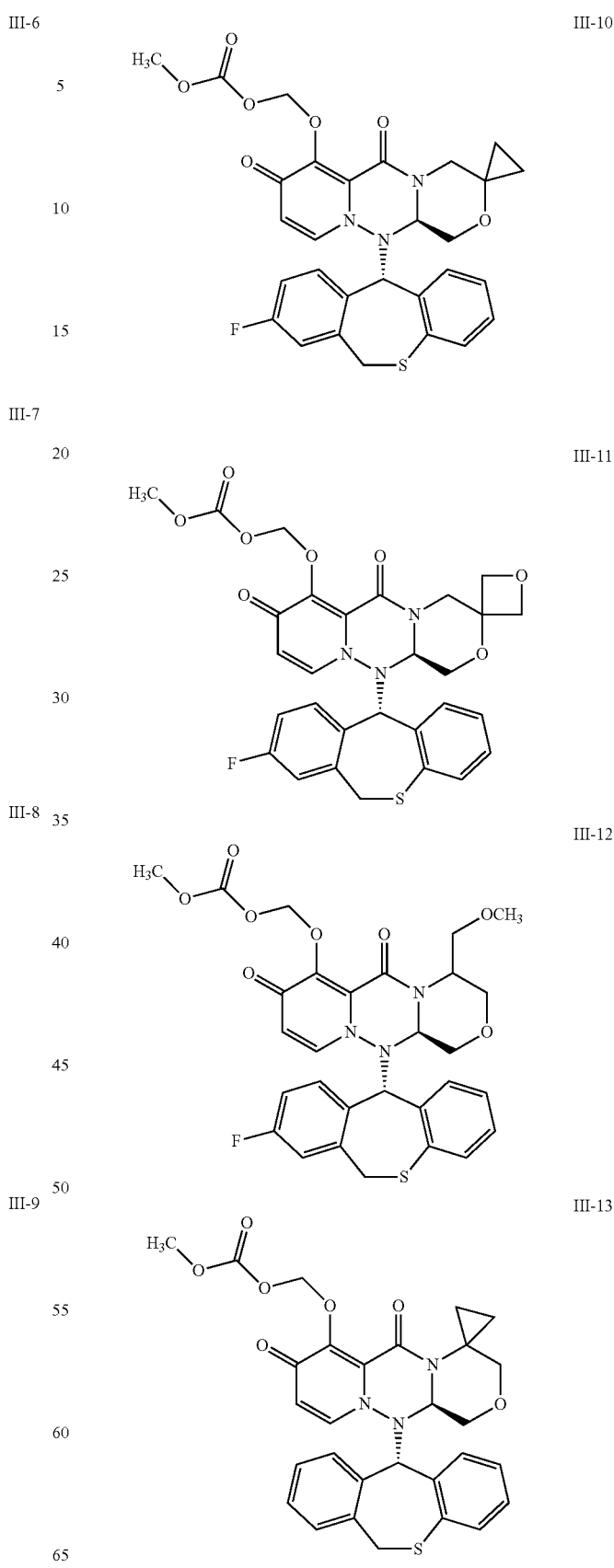

-continued
III-14
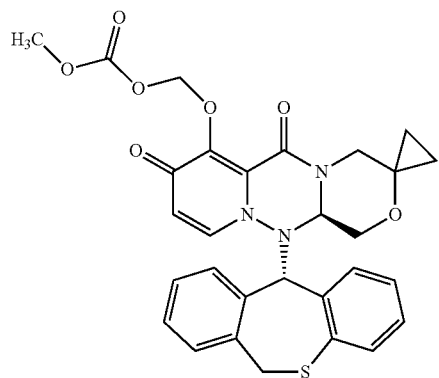
III-15
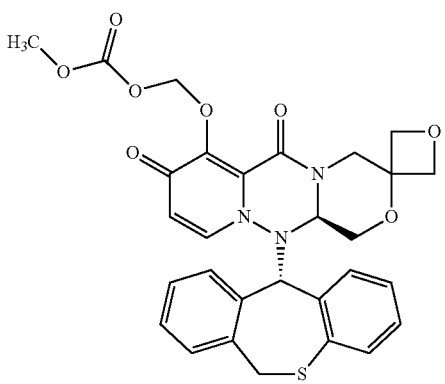
III-16
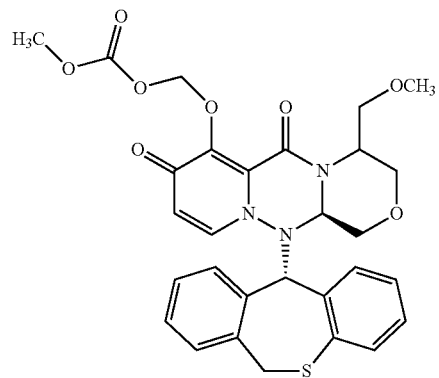
III-17
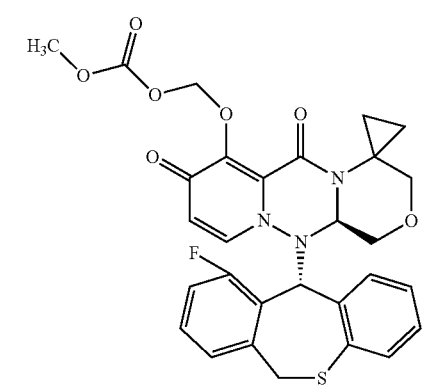
III-18
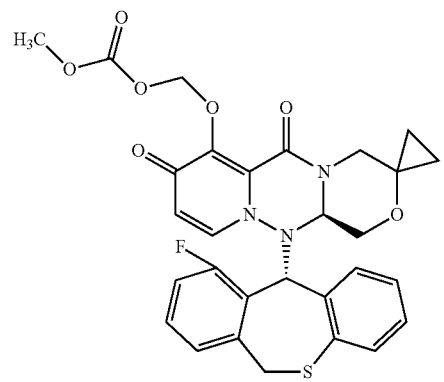
III-19
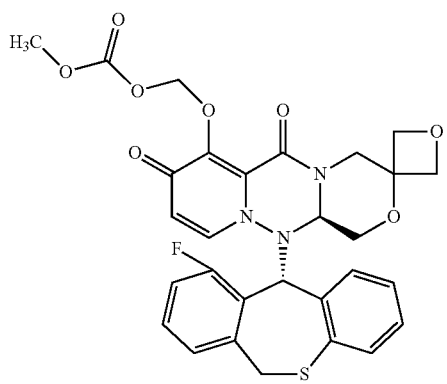
III-20
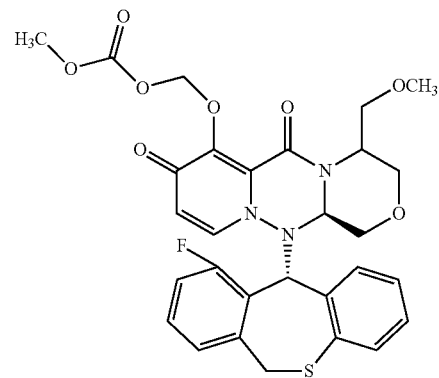
III-21
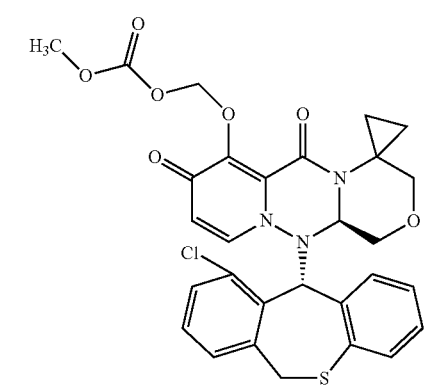

-continued
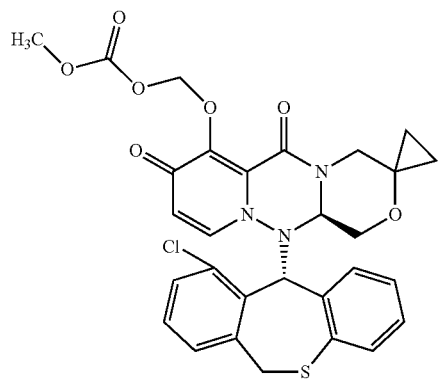
III-22
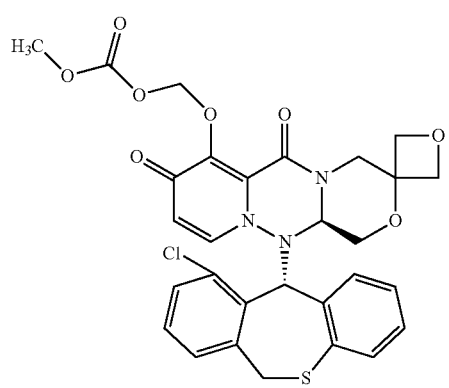
III-23
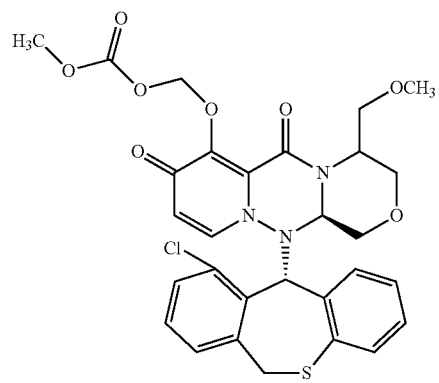
III-24
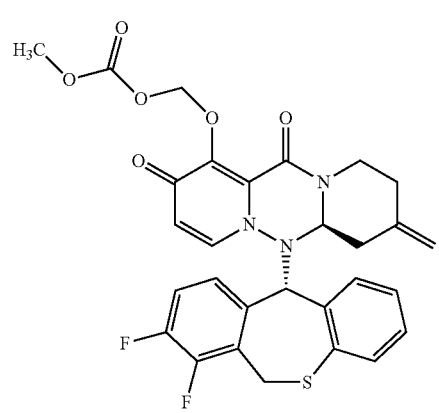
III-25
-continued
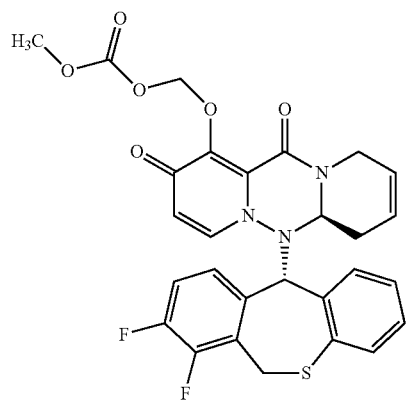
III-26
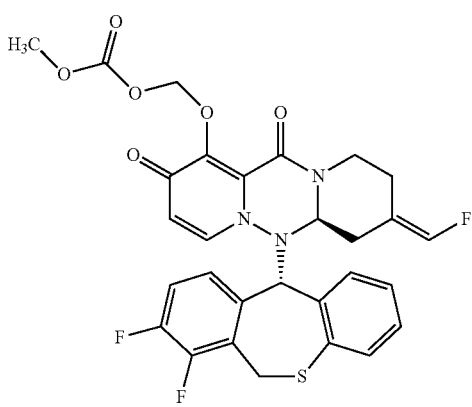
III-27
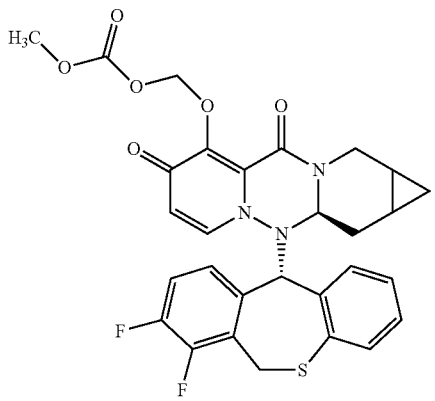
III-28
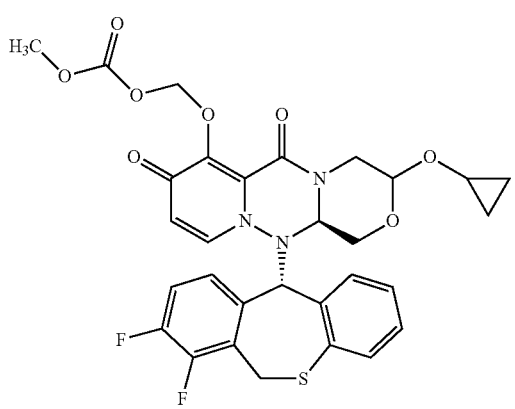
III-29

III-30
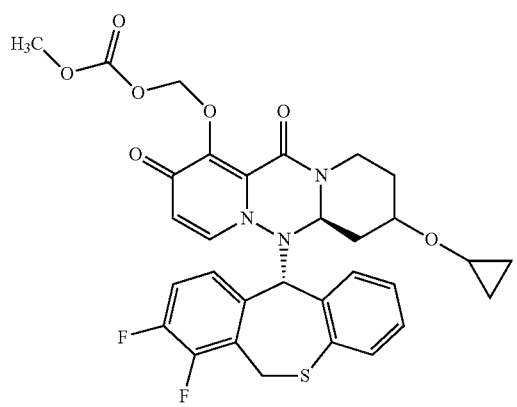
III-31
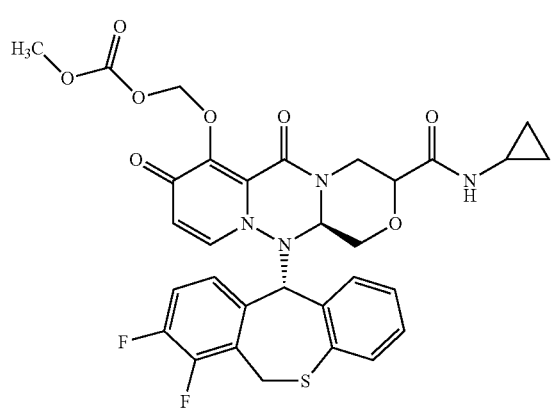
III-32
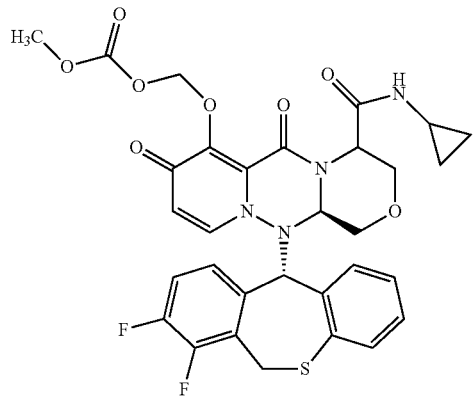
III-33
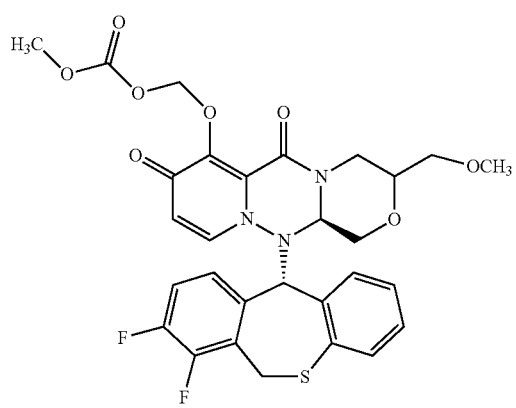
III-34
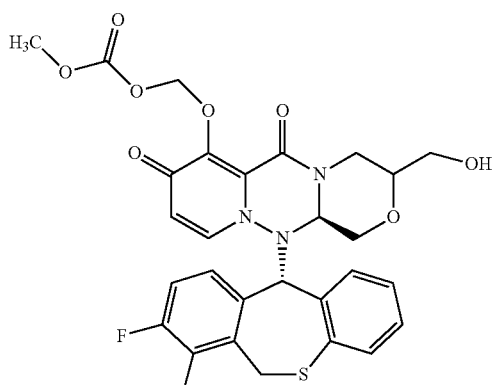
III-35
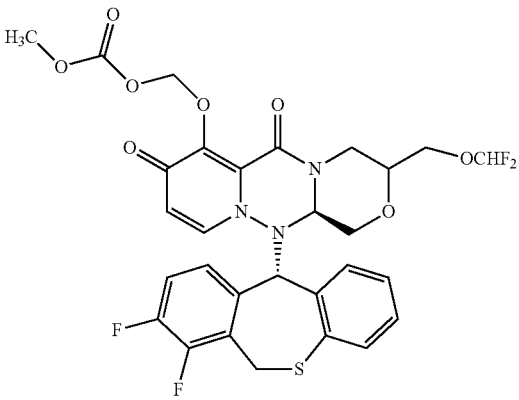
III-36
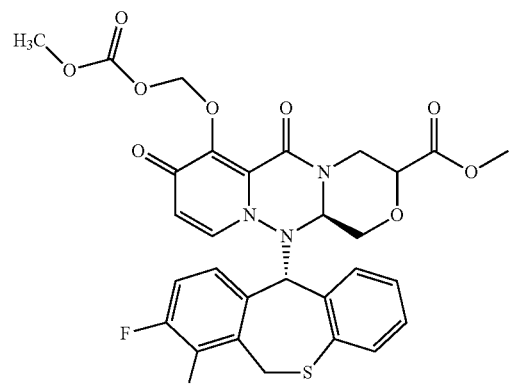
III-37
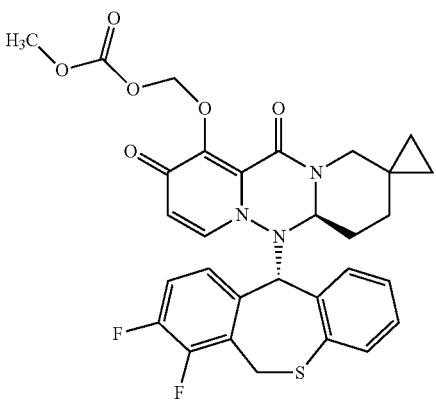

III-38
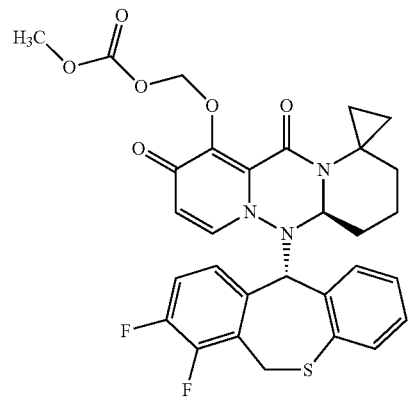
III-39
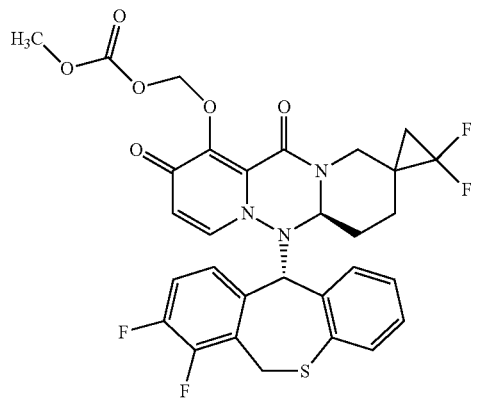
III-40
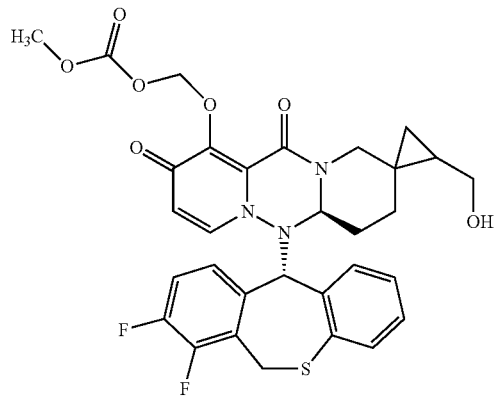
III-41
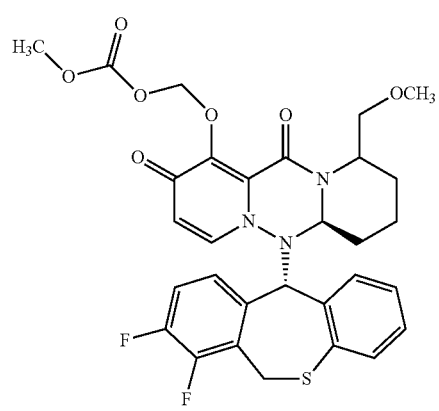
III-42
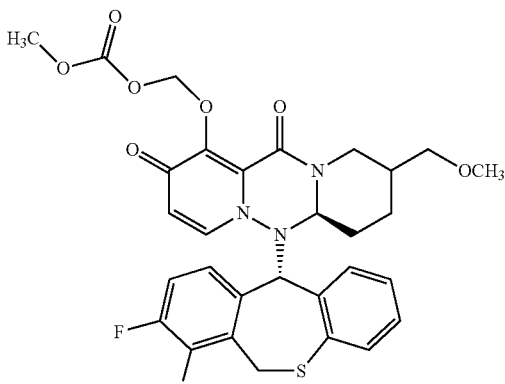
III-43
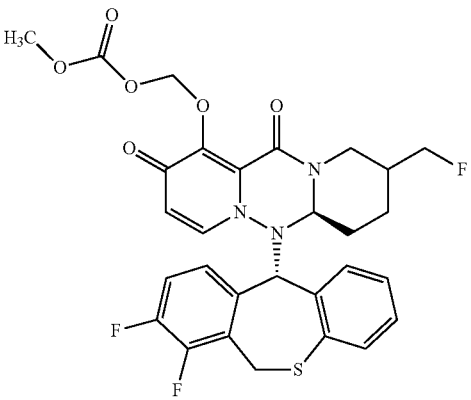
III-44
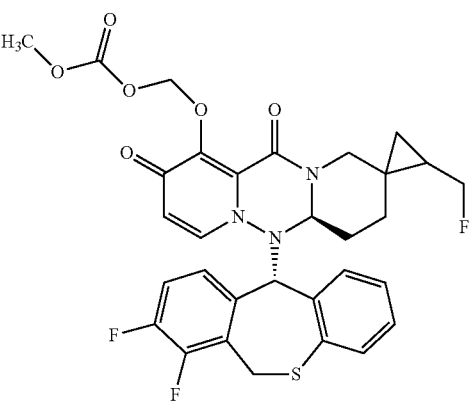
III-45
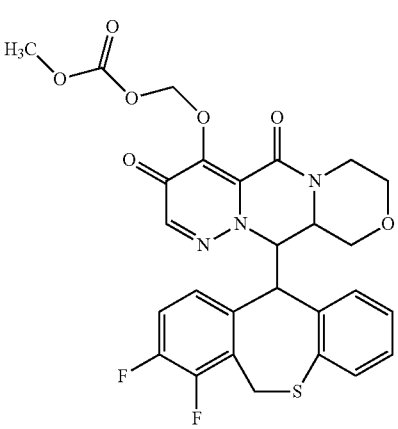

III-46
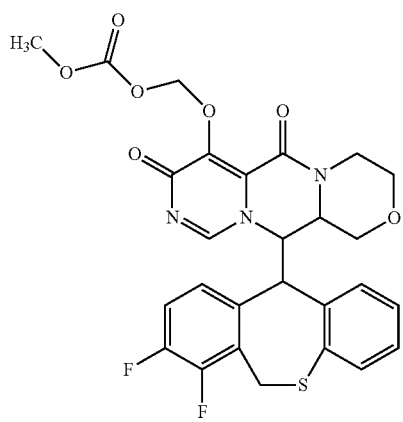
III-49
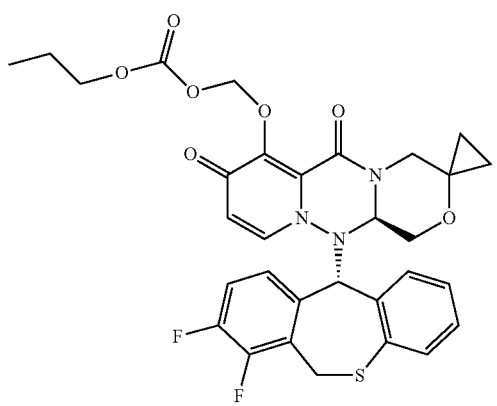
III-47
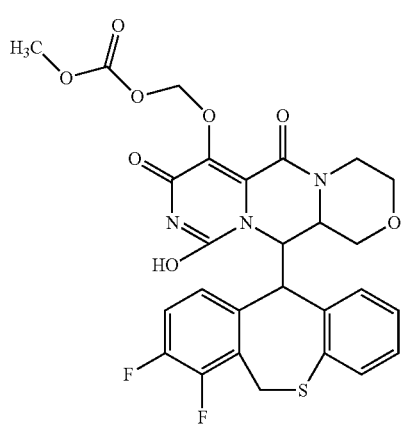
III-50
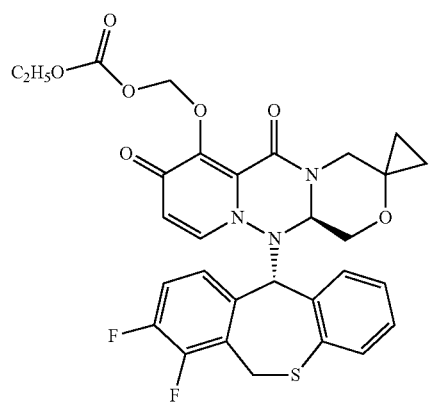
III-48
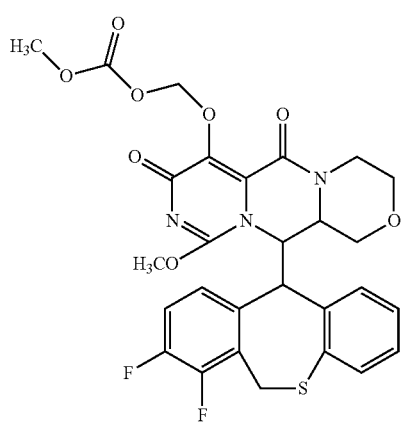
III-51
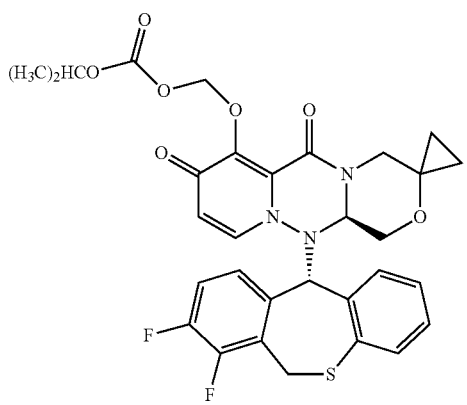

| 77 -continued | 78 -continued |
|---|---|
| III-52 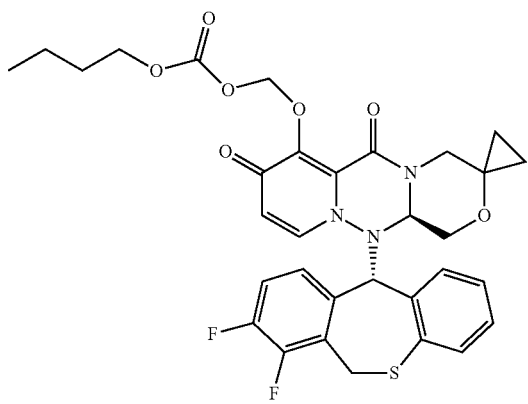 | III-56 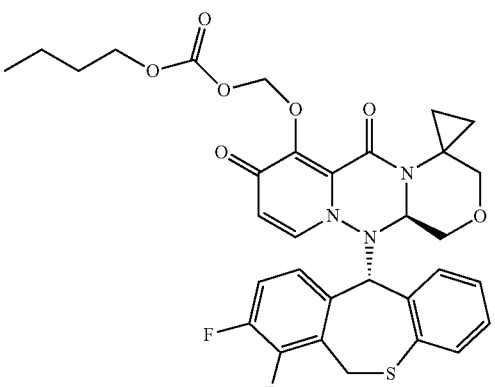 |
| III-53 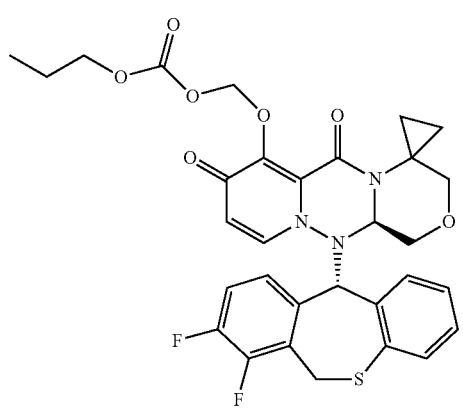 | III-57 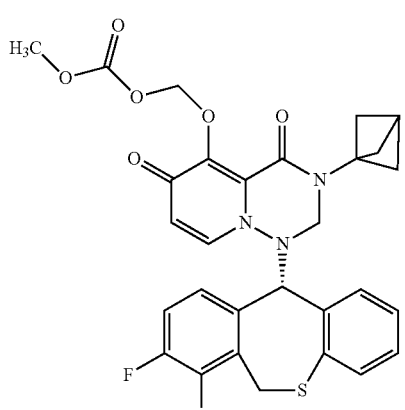 |
| III-54 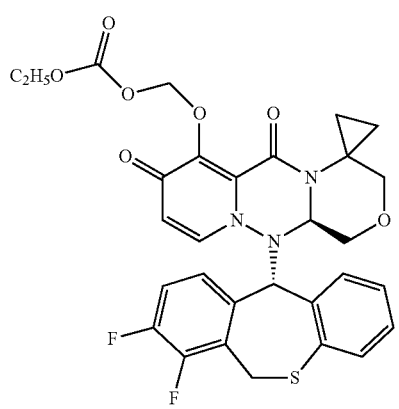 | III-58 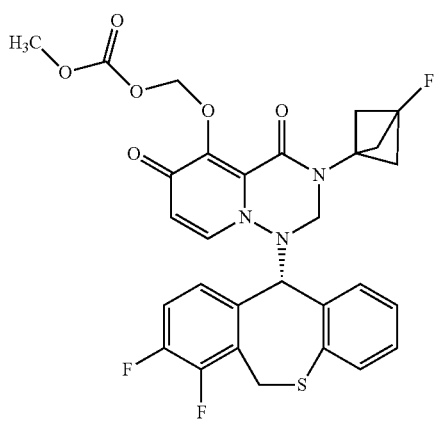 |
| III-55 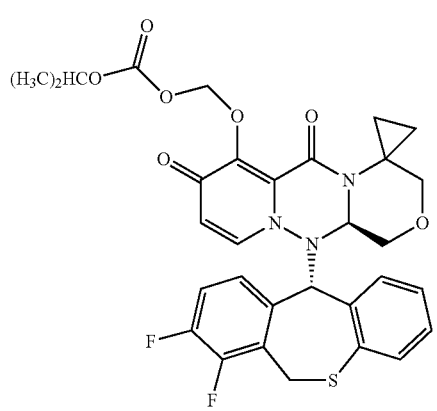 | III-59 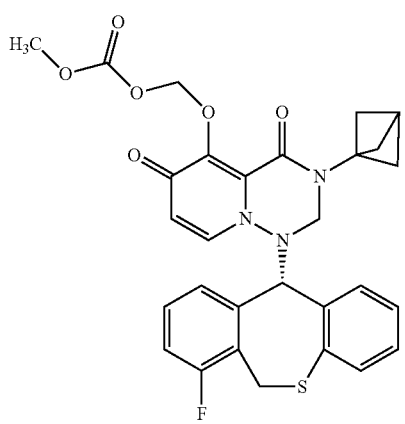 |

III-60
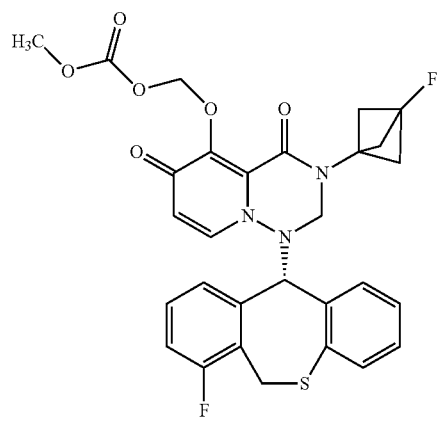
III-61
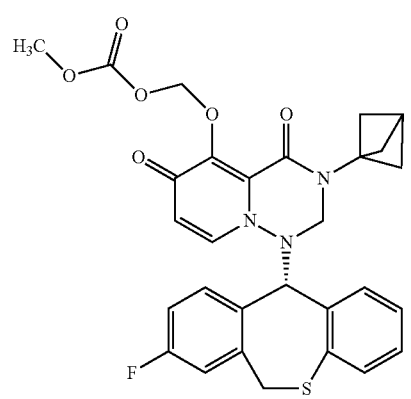
III-62
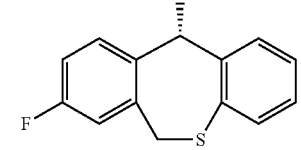
III-63
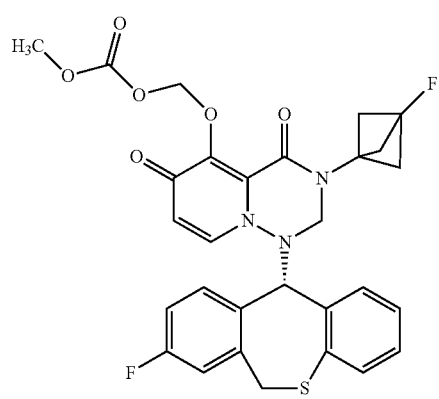
III-64
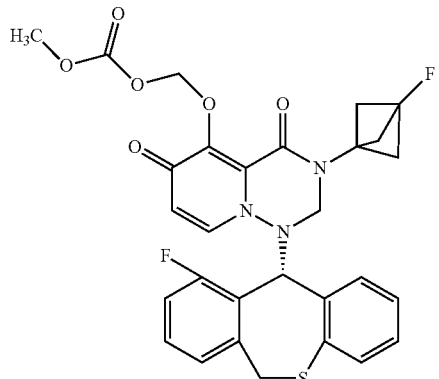
III-65
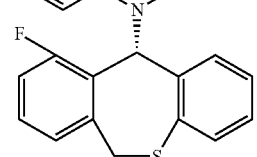
III-66
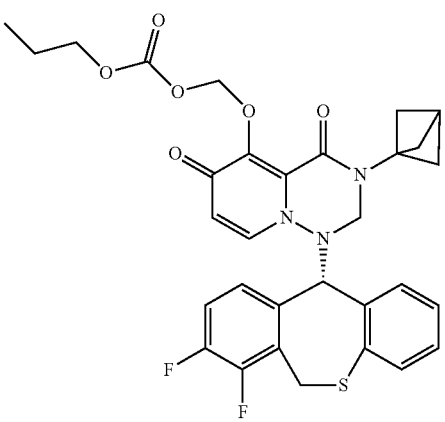
III-67
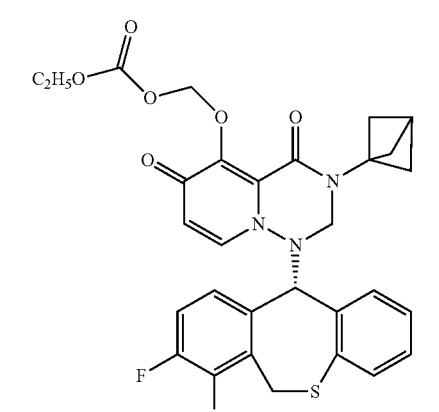

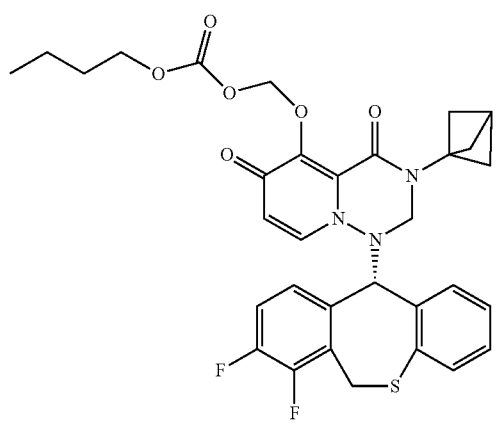
III-68
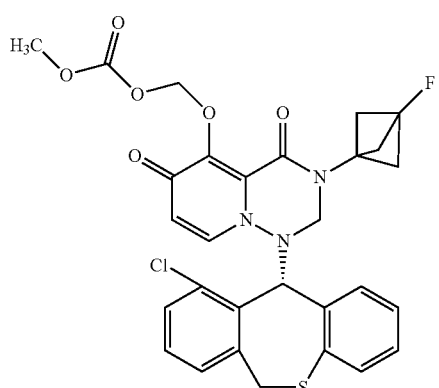
III-72
III-69
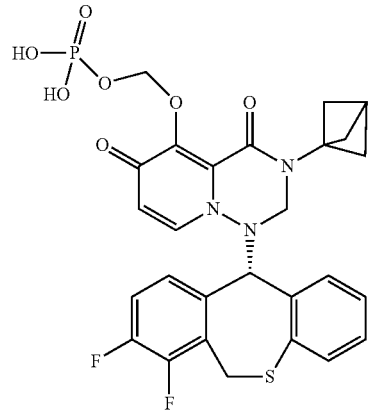
IV-1
III-70
III-71
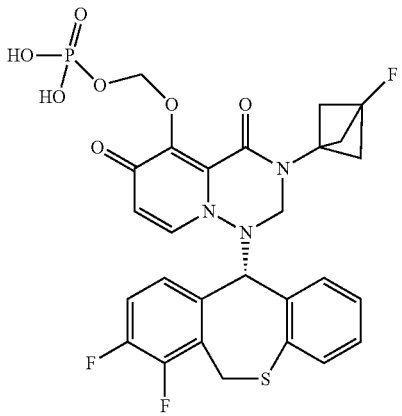
IV-2

IV-3
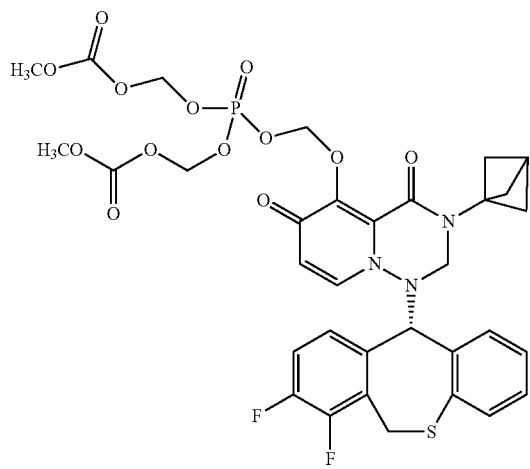
IV-4
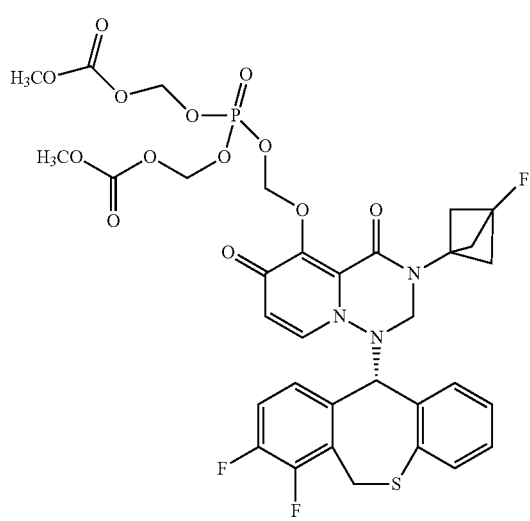
IV-5
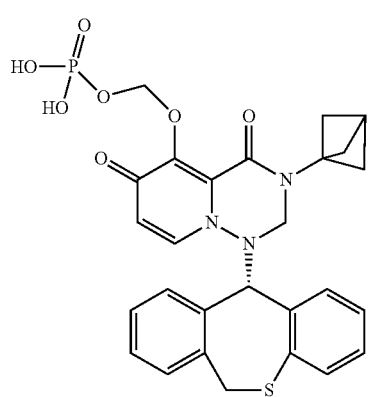
IV-6
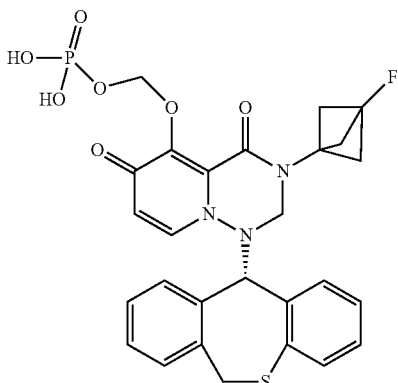
IV-7
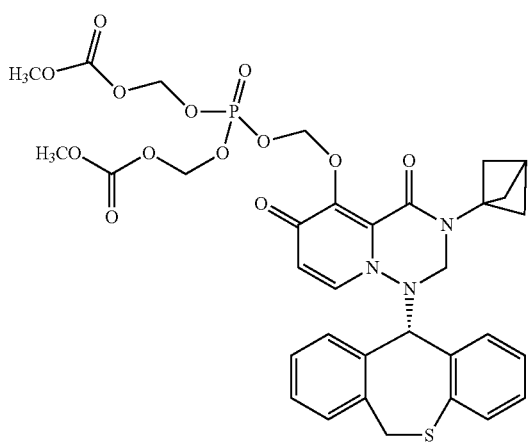
IV-8
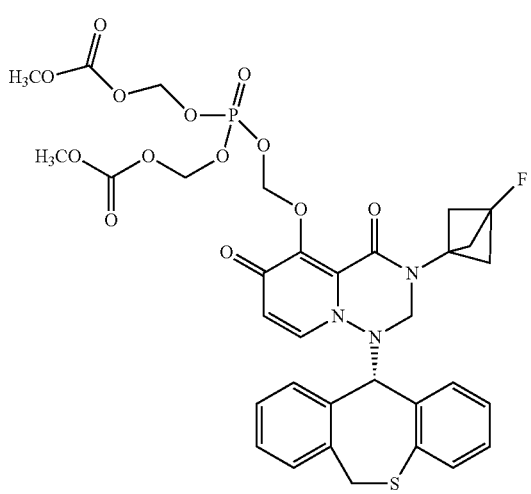

85
-continued
IV-9
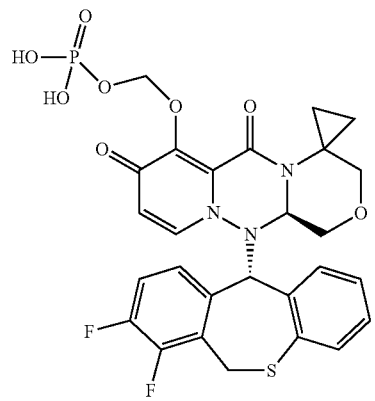
IV-10
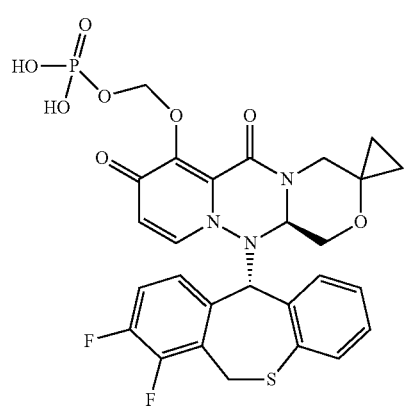
IV-11
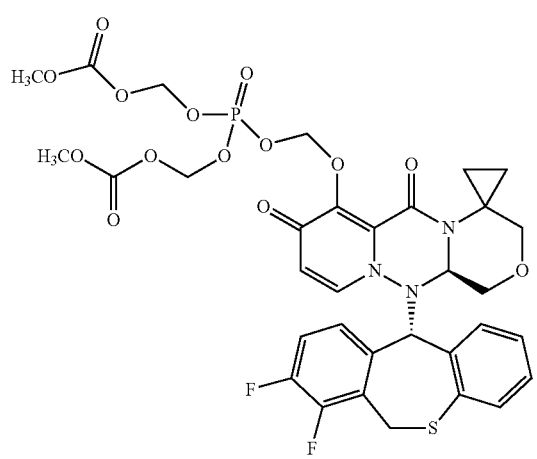
86
-continued
IV-12
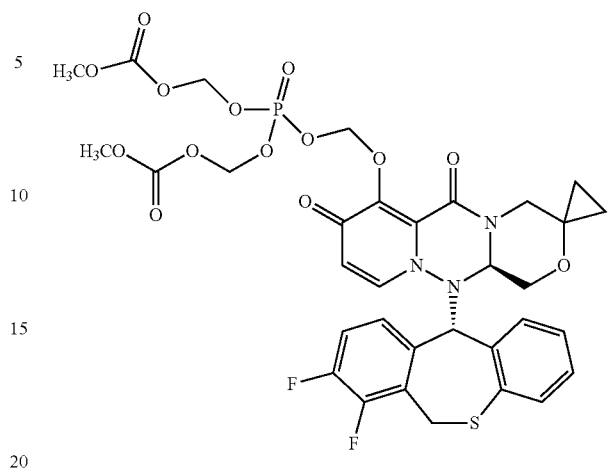
IV-13
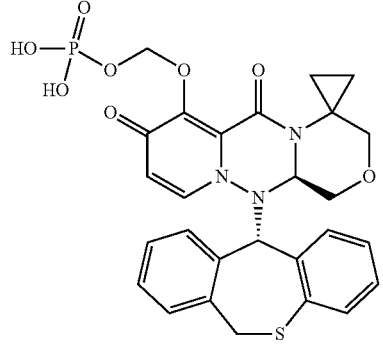
IV-14
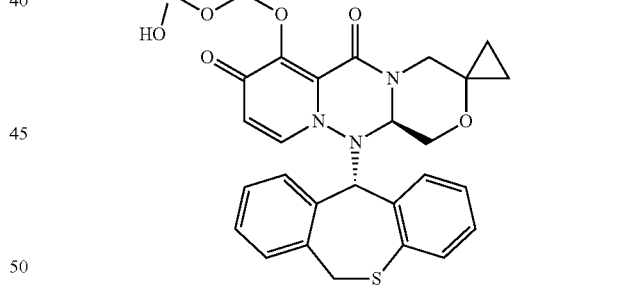
IV-15
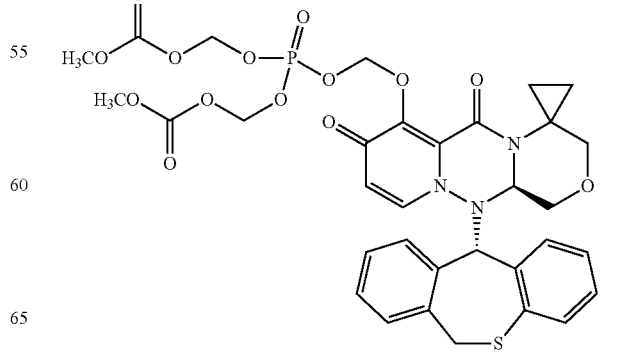

IV-16
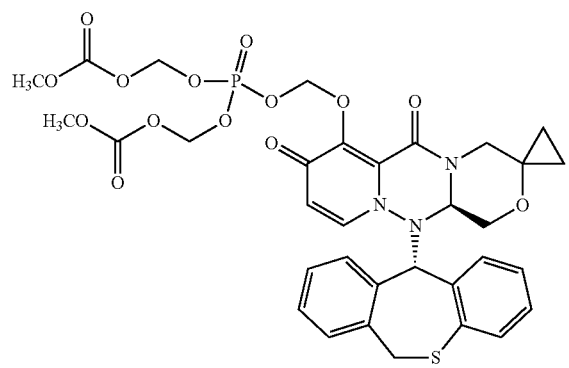
IV-17
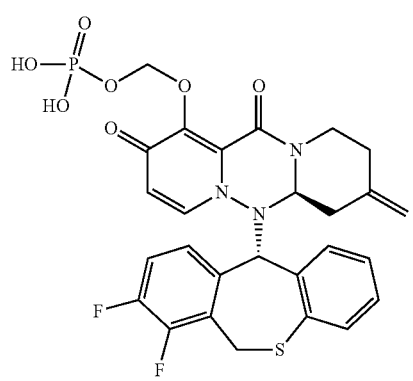
IV-18
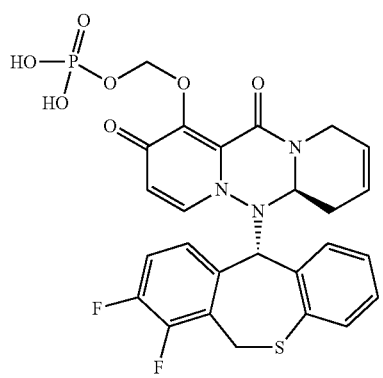
IV-19
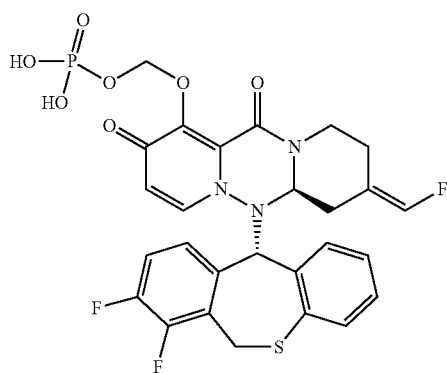
IV-20
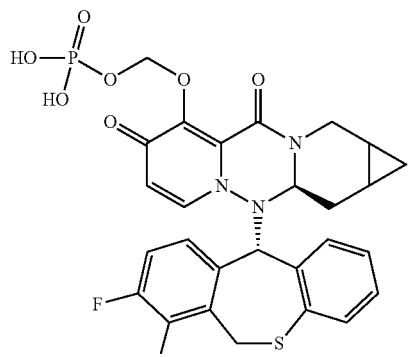
IV-21
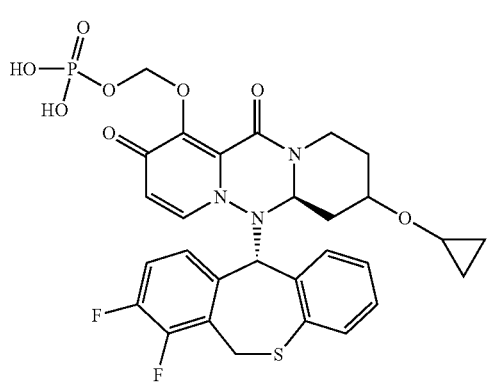
IV-22
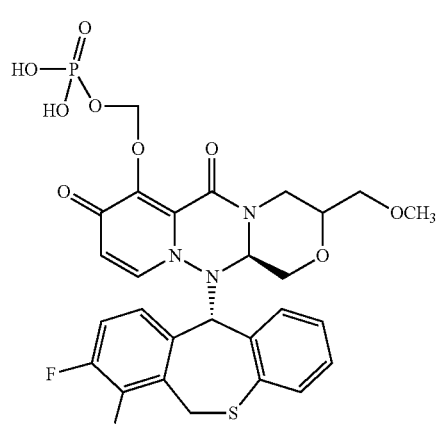
IV-23
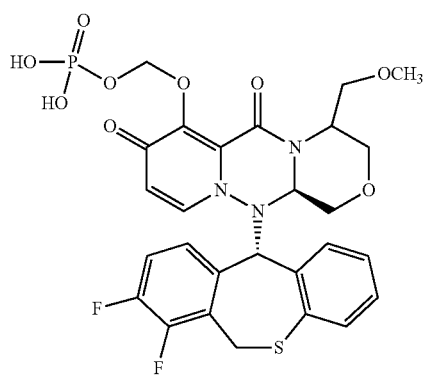

IV-24
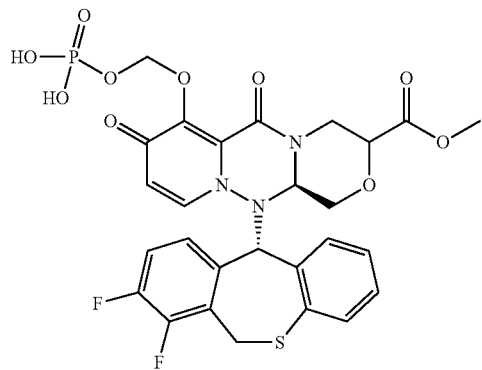
IV-28
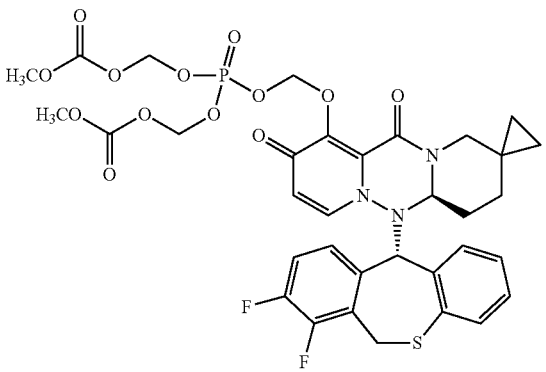
IV-25
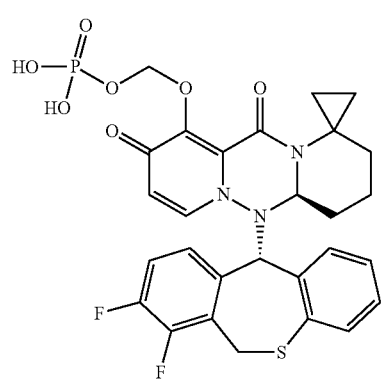
IV-29
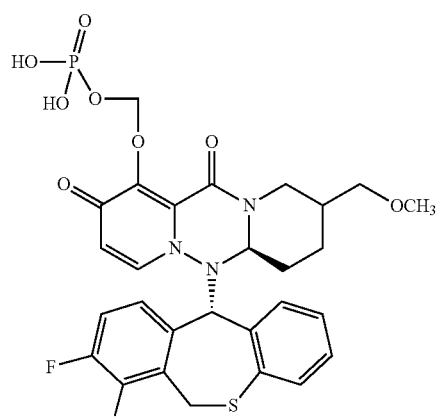
IV-26
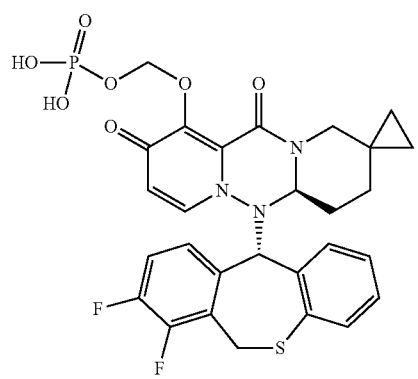
IV-30
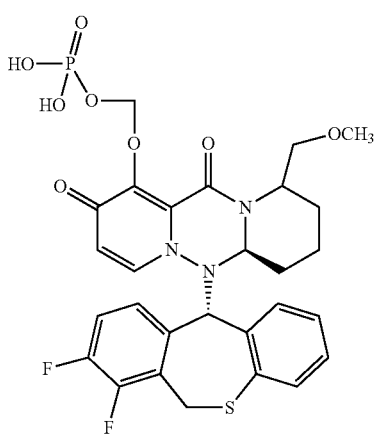
IV-27
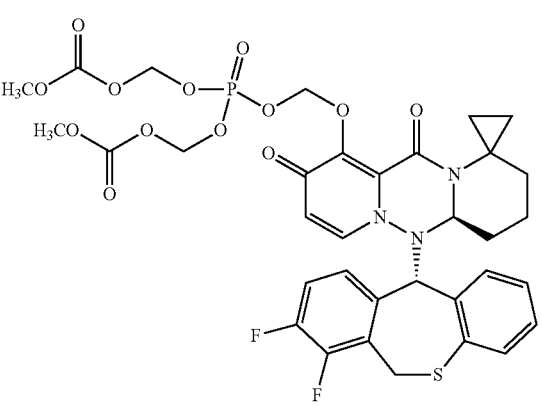
IV-31
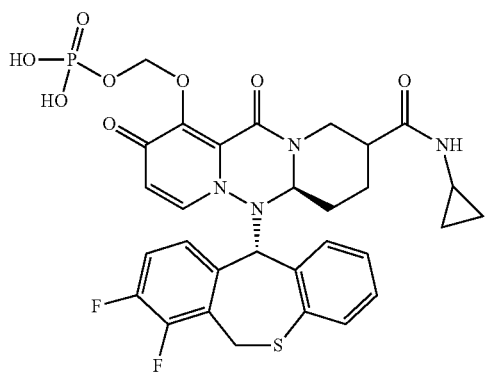

IV-32

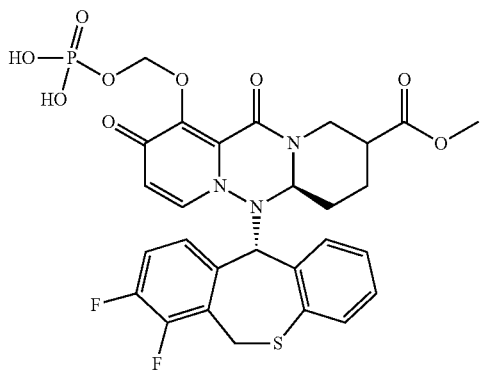

IV-36

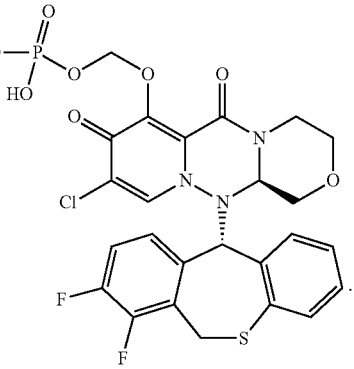

IV-33

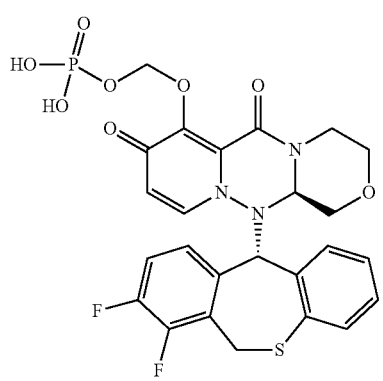

IV-34

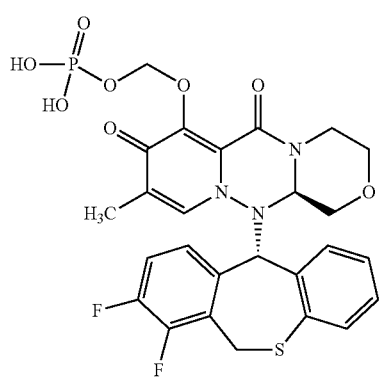

IV-35

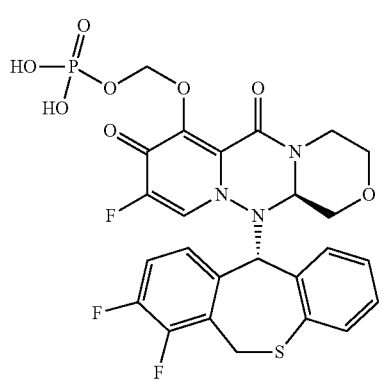

The present disclosure further provides a pharmaceutical composition comprising the pyridone derivative represented by Formula (I) or a stereoisomer, a pharmaceutically acceptable salt, a solvate or a crystal thereof.

Further, the pharmaceutical composition is an antiviral pharmaceutical composition further optionally comprising one or more therapeutic agents selected from the group consisting of a neuraminidase inhibitor, a nucleoside drug, a PB2 inhibitor, a PB1 inhibitor, an M2 inhibitor or other anti-influenza drugs.

Preferably, the antiviral pharmaceutical composition comprises at least one therapeutic agent.

The present disclosure further relates to use of the pyridone derivative represented by Formula (I) or the stereoisomer, the pharmaceutically acceptable salt, the solvate, the crystal or a combination thereof in the preparation of a drug for preventing and/or treating a viral infection disease, the viral infection disease is preferably infectious diseases caused by influenza type A viruses and/or influenza type B viruses.

The present disclosure further relates to use of the pyridone derivative represented by Formula (I) or the stereoisomer, the pharmaceutically acceptable salt, the solvate, the crystal or a combination thereof in the preparation of an antiviral drug, the antiviral drug is preferably a drug or an agent inhibiting influenza cap-dependent endonuclease activities.

In the present disclosure, for convenience of description, in some places, the pyridone derivative represented by Formula (I) or the stereoisomer, the pharmaceutically acceptable salt, the solvate, the crystal or any combination thereof is collectively referred to as the compound of the present disclosure.

In the pharmaceutical composition according to the present disclosure, the compound of the present disclosure is preferably present in a therapeutically effective amount.

The above pharmaceutical composition usually comprises a pharmaceutically acceptable carrier such as a pharmaceutically acceptable diluent, an excipient, a filler, a binder, a disintegrant, an absorption enhancer, a surfactant, a lubricant, a fragrance, a sweetener, etc.

Further, the pharmaceutical composition may employ any kind of dosage form, which may specifically be a tablet, a powder, a capsule, a granule, an oral liquid, an injection, a powder, a suppository, a pill, a cream, a paste, a gel, a pulvis, an inhalant, a suspension, a dry suspension, a patch, a lotion, a nano preparation, etc. The dosage form of the pharmaceutical composition is preferably a tablet, a capsule or an injection.

The above mentioned dosage forms of the drug can be prepared by conventional methods in the pharmaceutical field.

In a specific embodiment, the pharmaceutical composition according to the present disclosure may be constituted by, for example, the following ratio (mass ratio):

| | | |
|---|---|---|
| compound of the present disclosure | 5-95% | |
| lactose | 1-60% | |
| starch | 0-20% | |
| microcrystalline cellulose | 1-40% | |
| carboxymethyl starch sodium | 1-5% | |
| polyethylene glycol (PEG6000) | 0-10% | |
| magnesium stearate | 1-5% | |

The present disclosure further provides a process for the pyridone derivative, i.e., a compound of Formula (I) according to the present disclosure, which employs the following route:

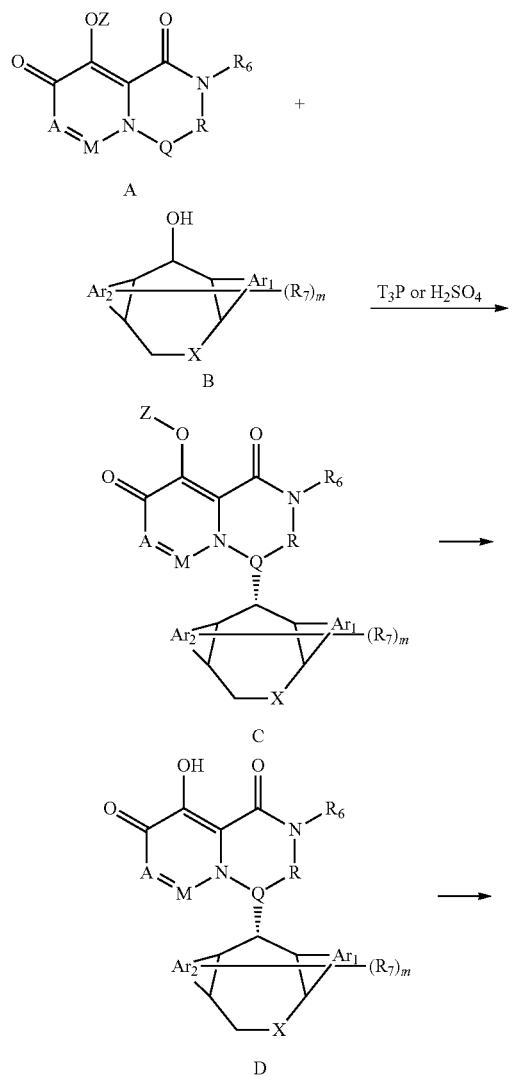

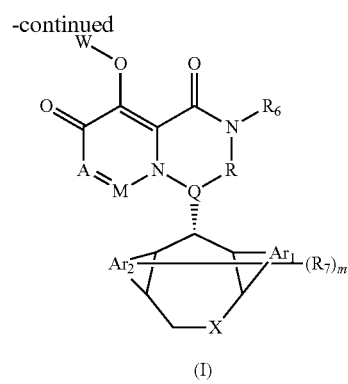

According to a specific embodiment of the present disclosure, the above reaction can be implemented according to the following steps:

Step-1: A and B are dissolved in ethyl acetate solution of 50% $T_3P$ and react at 60-100° C. for 1-10 hours to give Intermediate C.

Step-2: intermediate C and lithium chloride are reacted in DMA solution at 100° C. for 12 hours, and the mixture is purified to give Compound D.

Step-3: the obtained Compound D and acyl chloride or halide are reacted in the presence of an alkali to give a hydroxy-protected Prodrug (I), wherein the alkali comprises an organic alkali and an inorganic alkali, and the organic alkali is selected from triethylamine, DIPEA, DBU, and pyridine, etc.; and the inorganic alkali is selected from sodium carbonate, potassium carbonate, cesium carbonate, sodium hydroxide, potassium hydroxide, sodium hydride, potassium hydride, sodium bicarbonate, etc.

Due to the implementations of the above technical solutions, the present disclosure has the following advantages over the prior art:

the present disclosure provides a novel pyridone derivative, which has strong inhibitory activity against influenza virus A and influenza virus B, and can be used alone for clinical treatment or in combination with other anti-influenza drugs such as neuraminidase inhibitors, nucleoside drugs and PB2 inhibitors, and may rapidly cure influenza patients in the clinic. These compounds are superior to the exsiting pyridone derivatives in at least one aspect of activity, pharmacokinetic properties (such as bioavailability) and cytotoxicity.

Definition of Terms

Unless otherwise defined, all technical and scientific terms used herein have the same meaning as commonly understood by one of ordinary skill in the art to which this disclosure belongs.

The term "unsubstituted", when used to define a group, means that the defined group is not replaced by a group other than a hydrogen atom, in which case the group has the same meaning generally understood by one of ordinary skill in the art to which the present disclosure belongs. For example, an unsubstituted $C_{1-6}$ alkyl is a group generally understood by those skilled in the art such as methyl, ethyl or the like.

The term "substituted", when used to define a group, means that 1, 2, 3 or more hydrogen atoms on the defined group are replaced by a substituent, and the meaning of this group should be understood in conjunction with the substituent. In the present disclosure, unless otherwise specified, when referring to "substituted", it is meant that hydrogen atoms in a group defined thereby are replaced by 1, 2, 3 or more substituents selected from the group consisting of:

cyano, halogen, hydroxy, carboxyl, ester, sulfonyl, sulphonyl amide, amide, carbonyl (—C(═O)—), $C_{1-6}$ hydrocarbyl S(═O)(═NH)—, amino, carbonyl hydrazide, $C_{1-6}$ hydrocarbyl, halogenated $C_{1-6}$ hydrocarbyl, hydroxyl-substituted $C_{1-6}$ hydrocarbyl, acylamino-substituted $C_{1-6}$ hydrocarbyl, $C_{1-6}$ hydrocarbyloxy, halogenated $C_{1-6}$ hydrocarbyloxy, $C_{1-6}$ hydrocarbyloxy $C_{1-6}$ hydrocarbyl, $C_{1-6}$ hydrocarbyloxy $C_{1-6}$ hydrocarbyloxy, $C_{1-6}$ hydrocarbylamino, $C_{1-6}$ hydrocarbylsulfydryl, $C_{1-6}$ hydrocarbyl carbonyl, $C_{1-6}$ hydrocarbylamino carbonyl, $C_{1-6}$ hydrocarbyl amide, halogenated $C_{1-6}$ hydrocarbyl amide, $C_{1-6}$ hydrocarbyloxy acyl, $C_{1-6}$ hydrocarbylamino acylamino, $C_{1-6}$ hydrocarbyl sulfonyl, $C_{1-6}$ hydrocarbyl sulphonyl amide, $C_{3-6}$ cycloalkyl, halogenated $C_{3-6}$ cycloalkyl, $C_{3-6}$ cycloalkoxy, halogenated $C_{3-6}$ cycloalkoxy, $C_{3-6}$ cycloalkyl $C_{1-6}$ hydrocarbyl, $C_{3-6}$ cycloalkoxy $C_{1-6}$ hydrocarbyl, $C_{3-6}$ cycloalkyl $C_{1-6}$ hydrocarbyloxy, $C_{3-6}$ cycloalkyl $C_{1-6}$ hydrocarbyloxy $C_{1-6}$ hydrocarbyloxy, $C_{3-6}$ cycloalkylamino, $C_{3-6}$ cycloalkyl $C_{1-6}$ hydrocarbylamino, $C_{3-6}$ cycloalkylsulfydryl, halogenated $C_{3-6}$ cycloalkylsulfydryl, $C_{3-6}$ cycloalkyl $C_{1-6}$ hydrocarbylsulfydryl, $C_{3-6}$ cycloalkyl sulfonyl, $C_{3-6}$ cycloalkyl $C_{1-6}$ hydrocarbylsulfonyl, $C_{3-6}$ cycloalkyl sulphonyl amide, $C_{3-6}$ cycloalkyl $C_{1-6}$ hydrocarbyl sulphonyl amide, $C_{3-6}$ cycloalkylcarbonyl, $C_{3-6}$ cycloalkyl $C_{1-6}$ hydrocarbylcarbonyl, $C_{3-6}$ cycloalkylamino carbonyl, $C_{3-6}$ cycloalkyl $C_{1-6}$ hydrocarbylamino carbonyl, $C_{3-6}$ cycloalkyl amide, $C_{3-6}$ cycloalkyl $C_{1-6}$ hydrocarbyl amide, $C_{3-6}$ cycloalkylamino amide, $C_{4-8}$ heterocycloalkyl, $C_{4-8}$ heterocycloalkoxy, halogenated $C_{4-8}$ heterocycloalkoxy, $C_{4-8}$ heterocycloalkoxy $C_{1-6}$ hydrocarbyl, halogenated $C_{4-8}$ heterocycloalkoxy $C_{1-6}$ hydrocarbyl, $C_{4-8}$ heterocycloalkyl $C_{1-6}$ hydrocarbyloxy, halogenated $C_{4-8}$ heterocycloalkyl $C_{1-6}$ hydrocarbyloxy, $C_{4-8}$ heterocycloalkyl $C_{1-6}$ hydrocarbyl, $C_{4-8}$ heterocycloalkyl $C_{1-6}$ hydrocarbyloxy $C_{1-6}$ hydrocarbyl, $C_{4-8}$ heterocycloalkylamino, $C_{4-8}$ heterocycloalkyl sulfydryl, $C_{4-8}$ heterocycloalkyl $C_{1-6}$ hydrocarbyl sulfydryl, $C_{4-8}$ heterocycloalkyl sulfonyl, $C_{4-8}$ heterocycloalkyl $C_{1-6}$ hydrocarbylsulfonyl, $C_{4-8}$ heterocycloalkyl sulfonyl amide, $C_{4-8}$ heterocycloalkyl $C_{1-6}$ hydrocarbyl sulfonyl amide, $C_{4-8}$ heterocycloalkyl carbonyl, $C_{4-8}$ heterocycloalkyl $C_{1-6}$ hydrocarbyl carbonyl, carbonyl-substituted $C_{4-8}$ heterocycloalkyl, $C_{4-8}$ heterocycloalkylamino carbonyl, $C_{4-8}$ heterocycloalkyl amide, $C_{4-8}$ heterocycloalkyl $C_{1-6}$ hydrocarbyl amide, $C_{5-10}$ aryl, $C_{5-10}$ aryloxy, $C_{5-10}$ aryloxy $C_{1-6}$ hydrocarbyl, $C_{5-10}$ aryl $C_{1-6}$ hydrocarbyl, $C_{5-10}$ aryl $C_{1-6}$ hydrocarbyloxy, $C_{5-10}$ arylamino, $C_{5-10}$ aryl sulfydryl, $C_{5-10}$ aryl $C_{1-6}$ hydrocarbyl sulfydryl, $C_{5-10}$ aryl sulfonyl, $C_{5-10}$ aryl $C_{1-6}$ hydrocarbyl sulfonyl, $C_{5-10}$ aryl sulfonyl amide, $C_{5-10}$ aryl $C_{1-6}$ hydrocarbyl sulfonyl amide, $C_{5-10}$ aryl carbonyl, $C_{5-10}$ aryl $C_{1-6}$ hydrocarbyl carbonyl, $C_{5-10}$ arylamino carbonyl, $C_{5-10}$ aryl amide or $C_{5-10}$ arylamino amide.

Preferably, the above substituent is selected from cyano, halogen (preferably F, Cl, Br), hydroxy, carboxyl, ester, sulfonyl, sulphonylamino, carbonylamino, carbonyl, $C_{1-6}$ hydrocarbyl sulfinylamino, amino, carbonyl hydrazide, $C_{1-6}$ hydrocarbyl, halogenated $C_{1-6}$ hydrocarbyl, hydroxyl-substituted $C_{1-6}$ hydrocarbyl, amide-substituted $C_{1-6}$ hydrocarbyl, $C_{1-6}$ hydrocarbyloxy, halogenated $C_{1-6}$ hydrocarbyloxy, $C_{1-6}$ hydrocarbyloxy $C_{1-6}$ hydrocarbyl or $C_{1-6}$ hydrocarbyloxy $C_{1-6}$ hydrocarbyloxy.

Further preferably, the above substituent is selected from cyano, F, Cl, Br, hydroxy, carboxyl, ester, sulfonyl, sulphonylamino, amide, carbonyl, methylsulfinylamino, ethylsulfinylamino, isopropylsulfinylamino, tert-butylsulfinylamino, amino, acylhydrazino, methyl, ethyl, n-propyl, isopropyl, cyclopropyl, n-butyl, isobutyl, tert-butyl, cyclobutyl, n-pentyl, isopentyl, neopentyl, cyclohexyl, halomethyl (specifically, for example, trifluoromethyl), haloethyl, halo-n-propyl, halo-isopropyl, halocyclopropyl, halo-n-butyl, halo-isobutyl, halo-tert-butyl, halocyclobutyl, hydroxymethyl, hydroxyethyl, hydroxy-n-propyl, hydroxyisopropyl, hydroxycyclopropyl, hydroxy-n-butyl, hydroxyisobutyl, hydroxy-tert-butyl, hydroxycyclobutyl, hydroxy-n-pentyl, hydroxyisopentyl, hydroxy neopentyl, hydroxycyclohexyl, methoxy, ethoxy, propoxy.

The substituent is usually placed before the group be substituted when come to specific naming, for example, "$C_{1-3}$ alkoxy $C_{3-8}$ cycloalkyl $C_{1-6}$ alkyl" means $C_{1-6}$ alkyl is substituted by $C_{3-8}$ cycloalkyl, and $C_{3-8}$ cycloalkyl is further substituted by $C_{1-3}$ alkoxy, for example: the structural formula of methoxycyclobutylmethyl is:

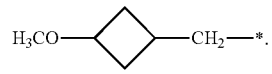

The term "uninterrupted", when used to define a group, means that a covalent bond of the defined group is not interrupted by another group, in which case the group has the same meaning generally understood by one of ordinary skill in the art to which the present disclosure belongs. For example, an unsubstituted cycloalkyl is a group generally understood by those skilled in the art such as cyclobutyl, cyclopentyl or the like.

The term "interrupt" or "interrupted", when used to define a group, means that one or more covalent bonds of the defined group are interrupted by interrupting atoms or groups, and the meaning of this group should be understood in conjunction with the interrupting atoms or groups. In the present disclosure, unless otherwise specified, when referring to "interrupted", it is meant that the covalent bonds in the group defined thereby are replaced by 1, 2, 3 or more selected from heteroatoms (O, N, S), C═O, S═O or $SO_2$. The position of the interruption may be any chemically achievable position, and when there are multiple interrupting atoms or groups, the relative positions between the multiple interrupting atoms or groups are not limited as long as they are chemically achievable.

The term "stereoisomer" refers to an isomer produced by the different arrangement of atoms in a molecule in space, and includes cis-trans isomers, enantiomers and conformers. All stereoisomers are within the scope of the present disclosure. The compounds of the present disclosure may be a single stereoisomer or a mixture of other isomers such as a racemate, or a mixture of all other stereoisomers.

The term "salt" refers to a pharmaceutically acceptable salt formed by a compound of the present disclosure with an acid, which may be an organic or inorganic acid, specifically selected from, for example, phosphoric acid, sulfuric acid, hydrochloric acid, hydrobromic acid, citric acid, maleic acid, malonic acid, mandelic acid, succinic acid, fumaric acid, acetic acid, lactic acid, nitric acid, sulfonic acid, p-toluenesulfonic acid, malic acid, methanesulfonic acid or analogues thereof.

The term "solvate" refers to a form of a compound of the present disclosure that forms a solid or liquid complex by coordination with a solvent molecule. Hydrates are a special form of solvates in which coordination occurs with water. Within the scope of the present disclosure, the solvate is preferably a hydrate.

The term "crystal" refers to the various solid forms formed by the compounds described herein, including crystalline forms and amorphous forms.

The term "hydrocarbyl" refers to alkyl or alkenyl.

The term "alkyl" refers to a linear, branched or cyclic saturated substituent consisting of carbon and hydrogen. It has preferably 1 to 20 carbon atoms, more preferably 1 to 12 carbon atoms. The term "alkyl" refers to a linear, branched or cyclic saturated hydrocarbyl group. The alkyl group specifically includes, for example, methyl, ethyl, n-propyl, isopropyl, cyclopropyl, n-butyl, isobutyl, tert-butyl, cyclobutyl, n-pentyl, isopentyl, neopentyl, cyclohexyl, n-hexyl, isohexyl, 2,2,-methylbutyl and 2,3-dimethylbutyl, 16-alkyl, 18-alkyl. The term "$C_{1-20}$ alkyl" refers to a linear, branched or cyclic saturated hydrocarbyl group containing 1 to 20 carbon atoms. When an alkyl group is substituted, the substituent may substitute at any available attachment point, and the substitution may be mono-substitution or poly-substitution. For example, the substituent can be selected from alkyl, alkenyl, alkoxy, alkylthio, alkylamino, deuterum, halogen, thiol, hydroxy, nitro, carboxy, ester, cyano, cycloalkyl, aryl, heteroaryl, cycloalkoxy, heterocycloalkoxy, cycloalkylthio or oxo.

The term "alkenyl" refers to a linear, branched or cyclic unsaturated hydrocarbyl group containing a double bond, preferably containing 2 to 20 carbon atoms, more preferably 2 to 12 carbon atoms. When it is substituted, the substituent may substitute at any available attachment point, and the substitution may be mono-substitution or poly-substitution. For example, the substituent can be selected from alkyl, alkenyl, alkoxy, alkylthio, alkylamino, deuterum, halogen, thiol, hydroxy, nitro, carboxy, ester, cyano, cycloalkyl, aryl, heteroaryl, cycloalkoxy, heterocycloalkoxy, cycloalkylthio or oxo.

The term "cycloalkyl" refers to a saturated monocyclic cyclohydrocarbyl group. A single ring generally includes 3 to 10 carbon atoms. Non-limiting examples of cycloalkyl groups include cyclopropyl, cyclobutyl, cyclopentyl, cyclopentenyl, cyclohexyl, cyclohexenyl, cyclohexadienyl, cycloheptyl and the like. In the present disclosure, spiro cycloalkyl groups, fused cycloalkyl groups, and bridged cycloalkyl groups are collectively referred to as polycyclic cycloalkyl groups.

The term "ring", unless otherwise specified, means any cyclic structure, and is not limited to any form and composition, and may be any form of a monocyclic ring, a bridged ring, a spiro ring, a fused ring, and a polycyclic ring, and may be a carbocyclic or heterocyclic ring or other forms of rings, such as a carbocyclic ring interrupted by carbonyl, and may be unsubstituted or substituted. When referring to "a ring containing a particular atom or group" means that the particular atom or group is part of the ring itself. For example, "the sixth ring contains C=O" means that the constituent group of the ring itself constituting the sixth ring contains C=O, and if only the substituent on the ring contains C=O, it is not among them.

The term "carbocyclyl" or "carbocyclic ring" refers to a carbocyclic group having 3 to 20 carbon atoms, preferably 3 to 16 carbon atoms, more preferably 4 to 12 carbon atoms, and includes cycloalkyl, cycloalkenyl, aryl, bicyclic carbocyclyl, polycyclic carbocyclyl, and the like. The term "heterocyclyl" or "heterocyclic ring" means that the ring structurally contains at least one heteroatom, and may specifically be, for example, heteroaryl, non-aromatic heterocyclyl, bicyclic heterocyclyl and polycyclic heterocyclyl containing one or more identical or different heteroatoms selected from O, S and N, etc.

The term "aryl" is to be understood broadly and includes not only carbocyclic aryl but also heteroaryl.

The term "carbocyclic aryl" refers to a 6- to 10-membered all-carbon monocyclic or polycyclic aromatic group, including phenyl, naphthyl, biphenyl, and the like. The carbocyclic aryl group can be substituted or unsubstituted. The substituent is independently selected from alkyl, cycloalkyl (such as cyclopropyl, cyclobutyl, cyclopentyl, etc.), alkenyl, azide, amino, deuterium, alkoxy, alkylthio, alkylamino, halogen, thiol, hydroxy, nitro, heterocycloalkyl, aryl, heteroaryl, cycloalkoxy, heterocycloalkoxy, cycloalkylthio, heterocycloalkylthio, alkylsilyl and so on.

The term "heteroaryl" refers to a group of a heteroaromatic system containing 1 to 10 heteroatoms, including monocyclic aryl and fused-ring aryl. Heteroatoms include oxygen, sulfur, nitrogen, phosphorus, and the like. Wherein monoheterocyclic groups include, but not limited to, furan, thiophene, pyrrole, thiazole, imidazole, 1,2,3-triazole, 1,2,4-triazole, 1,2,3-thiadiazole, oxazole, 1,2,4-oxadiazole, 1,3,4-oxadiazole, pyridine, pyrimidine, pyridazine, pyrazine, tetrahydrofuran, tetrahydropyrrole, piperidine, piperazine, morpholine, isoxazolin, and the like. Fused heterocyclic groups include, but not limited to, quinoline, isoquinoline, indole, benzofuran, benzothiophene, purine, acridine, carbazole, fluorene, chromenone, fluorenone, quinoxaline, 3,4-dihydronaphthalenone, dibenzofuran, hydrogenated dibenzofuran, benzoxazolyl, and the like. Heteroaryl groups can be substituted or unsubstituted. The substituent is, for example, selected from alkyl, cycloalkyl (such as cyclopropyl, cyclobutyl, cyclopentyl, etc.), alkenyl, azide, amino, deuterium, alkoxy, alkylthio, alkylamino, halogen, thiol, hydroxy, nitro, heterocycloalkyl, aryl, heteroaryl, cycloalkoxy, heterocycloalkoxy, cycloalkylthio, heterocycloalkylthio, alkylsilyl and so on.

The term "hydrogen", when not specifically stated, includes all isotopes of hydrogen, specifically can be protium (H), deuterium (D) or tritium (T), and preferably, hydrogen at different positions is independently selected from protium or deuterium. Wherein, the "hydrogen" in the active hydrogen position is protium. The term "deuterium" is an isotope of protium, the atomic mass is twice of that of the latter, and the binding to carbon is stronger. "Deuterated" and "deuterium" means that protium is replaced with deuterium at the specified position.

The term "haloalkyl" refers to an alkyl group substituted by at least one halogen atom.

The term "heterocyclic group" means a cyclic group containing at least one hetero atom, wherein the hetero atom is nitrogen, oxygen, sulfur, and the like. The heterocyclic groups include monoheterocyclic groups and polyheterocyclic groups.

The term "heteroatom", when not specifically indicated, generally includes nitrogen, oxygen and sulfur.

The term "halogen", when not specifically indicated, generally includes fluorine, chlorine, bromine and iodine, preferably fluorine, chlorine and bromine, and further preferably fluorine.

The term "plurality", "multiple" or "more", when used to define the number of substituents or interrupting atoms/groups, generally does not exceed the number of chemically replaceable groups or the number of bonds that can be interrupted, more specifically, "plurality", "multiple" or "more" preferably refers to a number less than or equal to 6, more preferably less than or equal to 5, and further preferably less than or equal to 4.

The term "optional" or "optionally" comprises two parallel schemes, "selected" and "not selected". For example, "the sixth ring optionally contains C=O" means that the sixth ring contains C=O or does not contain C=O.

DETAILED DESCRIPTION OF EXEMPLARY EMBODIMENTS

The following embodiments are intended to provide a more complete understanding of the present disclosure, and are not intended to limit the present disclosure in any way. The structures of all compounds were determined by [1]+1 NMR or MS.

The compound names used in the embodiments are abbreviated as follows:

DCM: dichloromethane; EA: ethyl acetate; DMF: dimethylformamide; THF: tetrahydrofuran; TEA: triethylamine T3P: 1-propylphosphoric anhydride; Boc-hydrazine: tert-butoxycarbonyl hydrazine;

HATU: 2-(7-oxobenzotriazole)-N,N,N',N'-tetramethyluron hexafluorophosphate

TFA: trifluoroacetic acid

DMA: N,N-dimethylacetamide

DPPP: 1,3-bis(diphenylphosphino)propane

DPPA: diphenylphosphoryl azide

DBU: 1,8-diazabicyclo-bicyclo(5,4,0)-7-undecene

DIPEA: N,N-diisopropylethylamine

The present disclosure will be further described below in conjunction with specific embodiments:

Embodiment 1: Preparation of Compound I-1

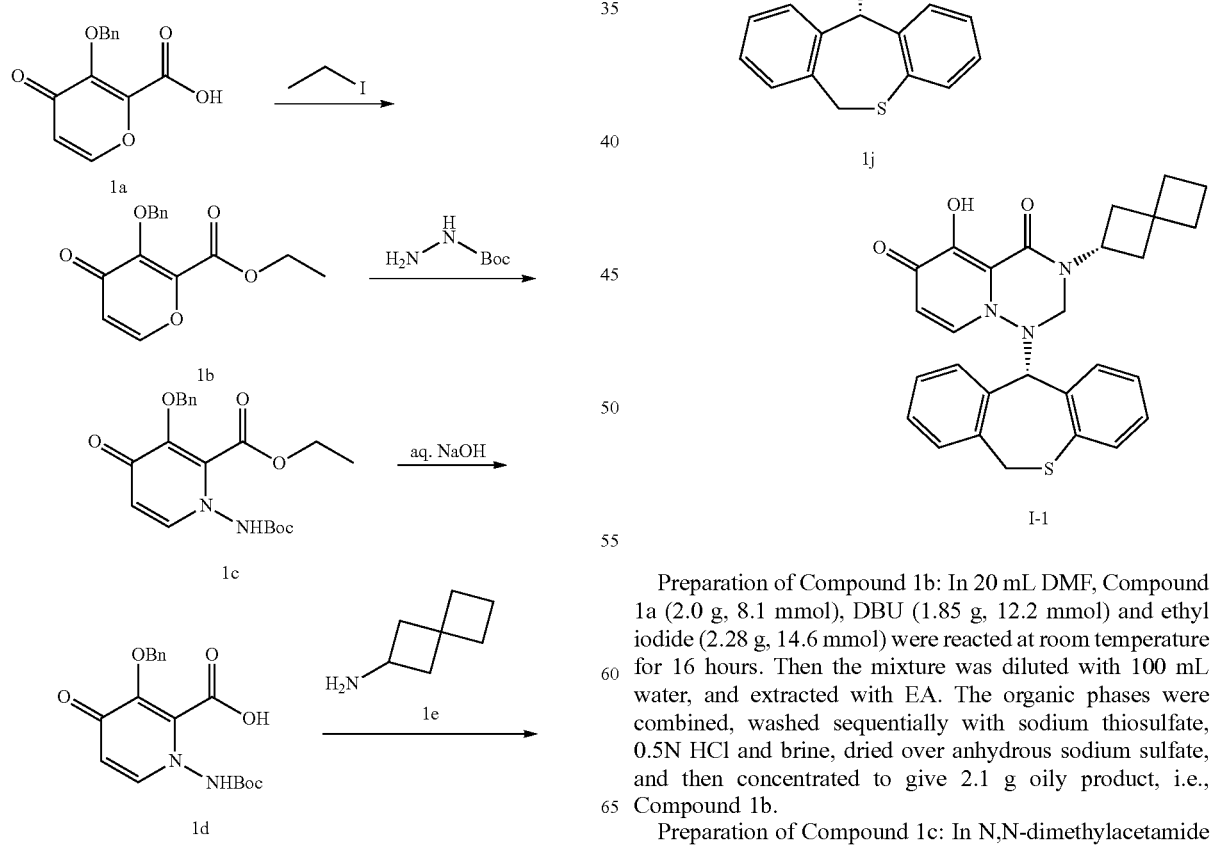

Preparation of Compound 1b: In 20 mL DMF, Compound 1a (2.0 g, 8.1 mmol), DBU (1.85 g, 12.2 mmol) and ethyl iodide (2.28 g, 14.6 mmol) were reacted at room temperature for 16 hours. Then the mixture was diluted with 100 mL water, and extracted with EA. The organic phases were combined, washed sequentially with sodium thiosulfate, 0.5N HCl and brine, dried over anhydrous sodium sulfate, and then concentrated to give 2.1 g oily product, i.e., Compound 1b.

Preparation of Compound 1c: In N,N-dimethylacetamide (20 mL), Compound 1b (2.1 g, 7.7 mmol), Boc-hydrazine (1.53 g, 11.6 mmol) and pyridinium p-toluenesulfonate (5.78 g, 23.1 mmol) were reacted at 60° C. for 16 hours. After the reaction finished, the mixture was added with 100 mL water, and then extracted with ethyl acetate (50 mL×3). The organic phases were combined, washed with brine, dried over anhydrous sodium sulfate and concentrated to give a crude product, which was purified by column chromatography to give 1.9 g yellow oily product, i.e., Compound 1c. ESI-MS m/z 389.2 (M+H)+

Preparation of Compound 1d: Compound 1c (1.9 g, 4.9 mmol) was dissolved in 10 mL ethanol, and 1N aq. NaOH solution (14.7 mL, 14.7 mmol) was added, and then the mixture was reacted at 60° C. for 24 hours. The mixture was acidified with 3N HCl and extracted with DCM. The organic phases were combined, washed with brine, dried and concentrated. The crude product was triturated in dichloromethane/petroleum ether (5 mL/50 mL) to give 1.1 g white solid, i.e., Compound 1d. ESI-MS m/z 361.2 (M+H)+

Preparation of Compound 1f: In DCM, Compound 1d (360 mg, 1 mmol), Compound 1e (133 mg, 1.2 mmol), TEA (303 mg, 3.0 mmol) and HATU (570 mg, 1.5 mmol) were stirred at room temperature overnight, then diluted with water, and extracted with DCM. The organic phases were combined, washed with brine, dried and concentrated, and purified by column chromatography to give 350 mg white solid, i.e., Compound 1f. ESI-MS m/z 454.2 (M+H)+

Preparation of Compound 1g: Compound 1f (350 mg, 0.77 mmol) was dissolved in 4 mL DCM, added with 1 mL TFA, and reacted at 0° C. for 6 hours. The mixture was concentrated, and 1N NaOH was added till basic, and the mixture was extracted with DCM/iPrOH. The organic phases were combined, washed with brine, dried and concentrated to give 210 mg oily product, which was directly used in the next step.

Preparation of Compound 1h: Compound 1g (210 mg, 0.59 mmol) was dissolved in 5 mL toluene. 30 mg paraformaldehyde and 100 mg acetic acid was added, and the mixture was reacted at 100° C. for 3 hours. The mixture was concentrated and separated by thin layer chromatography to give 145 mg product. ESI-MS m/z 366.2 (M+H)+

Preparation of Compound 1j: Compound 1h (140 mg, 0.38 mmol) and Compound 1i (114 mg, 0.5 mmol) were reacted in a solution of T3P in ethyl acetate at 100° C. for 3 hours in a pressured reactor. The mixture was cooled, diluted with saturated NaHCO₃, and then extracted with ethyl acetate. The organic phases were combined, dried and concentrated, and separated by silica gel plate to give 170 mg product. ESI-MS m/z 576.2 (M+H)+.

Preparation of Compound I-1: In 5 mL DMA, Compound 1j (170 mg, 0.29 mmol) and lithium chloride (50 mg, 1.18 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 120 mg product. $^1$HNMR (400 MHz, CDCl$_3$) δ: 7.46-7.53 (m, 2H), 7.36 (s, 2H), 7.13-7.17 (m, 3H), 6.89 (s, 1H), 6.76 (s, 1H), 5.76-5.88 (m, 2H), 5.14 (s, 1H), 4.88-4.91 (m, 1H), 4.77-4.80 (m, 1H), 4.48-4.51 (m, 1H), 3.66-3.69 (m, 1H), 2.30 (s, 2H), 2.16 (s, 2H), 1.78-1.90 (m, 6H); ESI-MS m/z 486.2 (M+H)+.

Embodiment 2: Preparation of Compound I-5

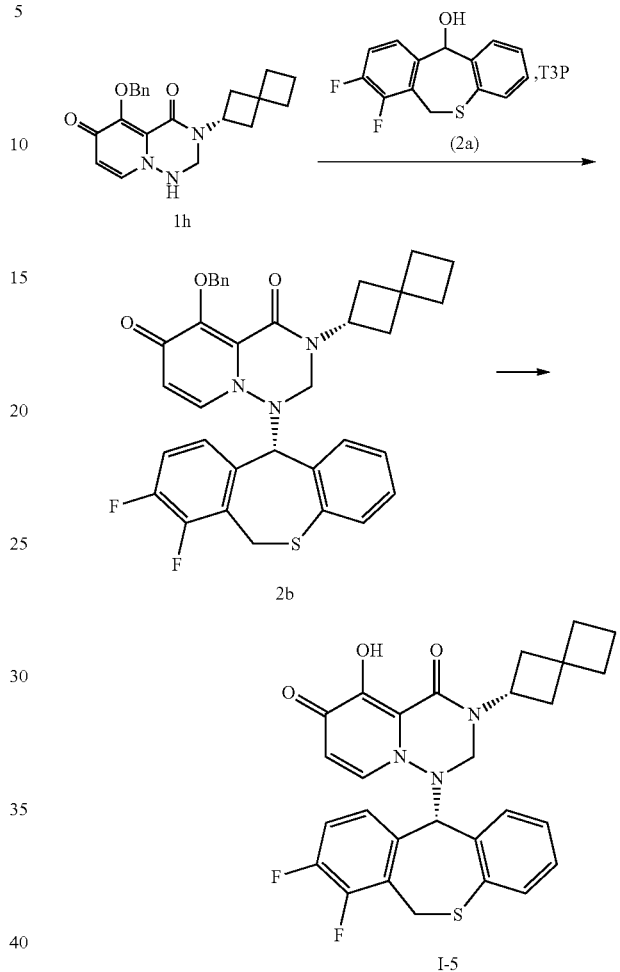

Preparation of Compound 2b: Compound 1h (180 mg, 0.49 mmol) and Compound 2a (264 mg, 1.0 mmol) were reacted in a solution of T3P in ethyl acetate at 100° C. for 3 hours in a pressured reactor. The mixture was cooled, diluted with saturated NaHCO₃ aqueous solution, and then extracted with ethyl acetate. The organic phases were combined, dried and concentrated, and separated by silica gel plate to give 190 mg product. ESI-MS m/z 612.2 (M+H)+.

Preparation of Compound I-5: In 5 mL DMA, Compound 2b (190 mg, 0.31 mmol) and lithium chloride (50 mg, 1.18 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 136 mg product. $^1$HNMR (400 MHz, CDCl$_3$) δ: 7.04-7.12 (m, 3H), 7.00-7.02 (d, 1H, J=7.6 Hz), 6.90-6.93 (m, 1H), 6.79-6.83 (m, 1H), 6.63-6.64 (d, 1H, J=7.2 Hz), 5.74-5.76 (d, 1H, J=7.6 Hz), 5.42-5.46 (m, 1H), 5.06 (s, 1H), 4.82-4.86 (m, 1H), 4.69-4.77 (m, 1H), 4.37-4.40 (m, 1H), 4.04-4.07 (m, 1H), 2.18-2.28 (m, 2H), 2.06-2.09 (m, 2H), 1.74-1.85 (m, 6H); ESI-MS m/z (M+H)+522.2.

Embodiment 3: Preparation of Compound I-7

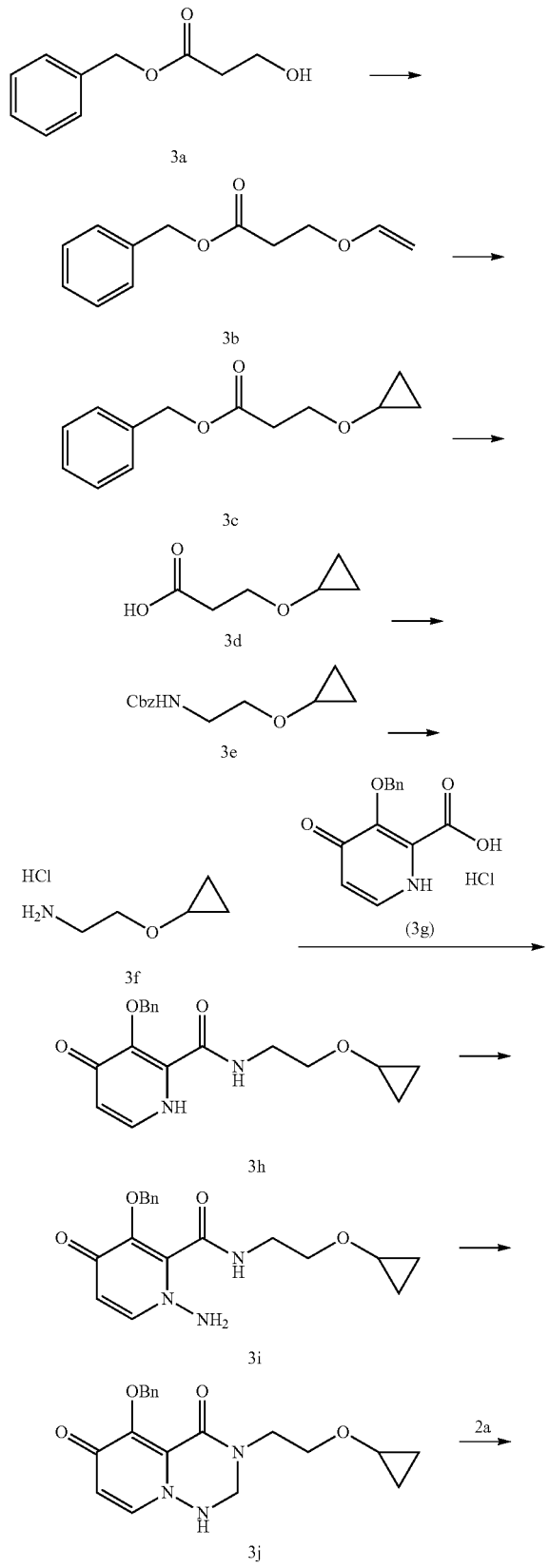

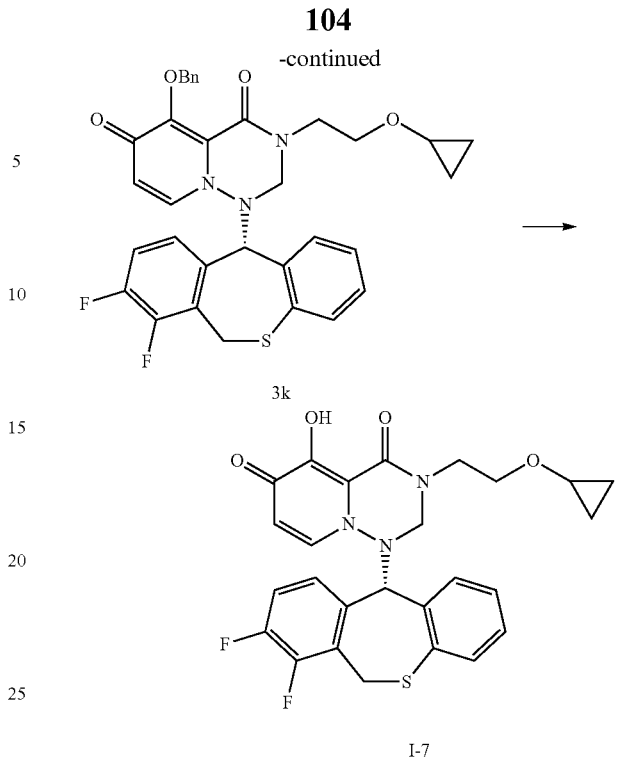

Preparation of Compound 3b: Compound 3a (5.0 g, 27.8 mmol) was added to n-butyl vinyl ether (10 mL), then added with palladium trifluoroacetate (100 mg, 0.3 mmol), triethylamine (3.03 g, 30 mmol) and DPPP (124 mg, 0.3 mmol), and stirred at 75° C. overnight in a pressured reactor. TLC showed the reaction was complete. The mixture was added with 50 mL water and extracted with ethyl acetate twice, and the organic phase was washed with brine, dried over anhydrous sodium sulfate, concentrated and separated by column chromatography to give 4.8 g product, which was directly used in the next step.

Preparation of Compound 3c: Compound 3b (4.8 g, 23.3 mmol) was dissolved in 50 mL anhydrous toluene, and added with 1N diethylzinc solution (70 mL, 70 mmol) at −40° C. under nitrogen protection. After addition, the mixture was stirred for 1 hour, and then added with chloroiodomethane (8.22 g, 46.6 mmol). After addition, the mixture was stirred for 2 hours, slowly heated to room temperature and stirred overnight. TLC showed the reaction was complete, and then the reaction mixture was poured into ammonium chloride solution, and then extracted with ethyl acetate (100 mL×3). The organic phases were combined, dried over anhydrous sodium sulfate and concentrated to give 4.9 g crude product.

Preparation of Compound 3d: Intermediate 3c (4.9 g, 22.2 mmol) was dissolved in 50 mL methanol, added with aqueous sodium hydroxide, and stirred at room temperature for 5 hours. TLC showed starting material consumed. HCl was added to adjust pH=2-3 and the mixture was extracted with ethyl acetate (100 mL×3). The organic phases were concentrated to give 2.3 g crude product.

Preparation of Compound 3e: Compound 3d (2.3 g, 17.7 mmol) was dissolved in 15 mL toluene, added with DPPA (5.84 g, 21.2 mmol) and TEA (3.58 g, 35.4 mmol), stirred at room temperature for 2 hours, then added with benzyl alcohol (5.73 g, 53.1 mmol), and reacted at 90° C. for 2 hours. TLC showed the reaction was complete, and the mixture was cooled to room temperature, and added with 100 mL water to quench the reaction, extracted with ethyl acetate (80 mL×3), and the organic phases were combined, dried and concentrated to give a crude product, which ran through column chromatography to give 1.5 g mixture of product and benzyl alcohol that directly used in the next step.

Preparation of Compound 3f: 1.5 g crude of Compound 3e was dissolved in 10 mL methanol, and added with 150 mg Pd/C and 0.2 mL concentrated hydrochloric acid. The mixture was replaced with hydrogen for three times and was reacted for 5 hours. TLC showed the reaction was complete, and the mixture was filtered through diatomite, and the filtrate was added with HCl to adjust pH=1-2, and concentrated to dry to give 0.6 g product, which was directly used in the next step.

Preparation of Compound 3h: In 15 mL dichloromethane, Compound 3f (0.6 g, 4.36 mmol), Compound 3g (1.12 g, 4.0 mmol), HATU (1.82 g, 4.8 mmol) and TEA (1.21 g, 12.0 mmol) were stirred at room temperature over night. TLC showed the reaction was complete, and the mixture was added with 20 mL water and extracted with dichloromethane (30 mL×2), and the organic phases were combined, dried and concentrated to give a crude product, which was separated by column chromatography to give 0.85 g product.

Preparation of Compound 3i: In 5 mL DMF, Compound 3h (0.85 g, 2.6 mmol), potassium carbonate (718 mg, 5.2 mmol) and 2,4-dinitrophenylhydroxylamine (0.78 g, 3.9 mmol) were stirred at room temperature for 5 hours. TLC showed the reaction was complete, and the mixture was added with 20 mL water and extracted with dichloromethane (20 mL×3), and the organic phases were combined, dried and concentrated to give a crude product, which was separated by column chromatography to give 0.73g product.

Preparation of Compound 3j: Compound 3i (0.73 g, 2.1 mmol), acetic acid (120 mg, 2.1 mmol) and paraformaldehyde (0.23g, 2.52 mmol) were refluxed in toluene for 2 hours. TLC showed the reaction was complete. The mixture was concentrated, and the residue was added with 10 mL water and extracted with dichloromethane (20 mL×3), and the organic phases were combined, dried and concentrated to give a crude product, which was separated by column chromatography to give 0.45g product.

Preparation of Compound 3k: In 3 mL solution of T3P in ethyl acetate, Compound 3j (450 mg, 1.27 mmol) and Compound 2a (660 mg, 2.54 mmol) were reacted at 100° C. for 3 hours in a pressured reactor. The mixture was cooled, diluted with saturated NaHCO$_3$, and then extracted with ethyl acetate. The organic phases were combined, dried and concentrated, and separated by column chromatography to give 290 mg product. ESI-MS m/z 602.2 (M+H)$^+$.

Preparation of Compound 1-7: In 5 mL DMA, Compound 3k (290 mg, 0.48 mmol) and lithium chloride (50 mg, 1.18 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 187 mg product. $^1$HNMR (400 MHz, CDCl$_3$) δ: 7.05-7.15 (m, 3H), 7.00-7.02 (d, 1H, J=8.0 Hz), 6.94-6.98 (m, 1H), 6.81-6.85 (m, 1H), 6.65-6.67 (d, 1H, J=8.0 Hz), 5.80-5.82 (d, 1H, J=8.0 Hz), 5.38-5.42 (m, 1H), 5.13 (s, 1H), 4.96-5.00 (m, 1H), 4.21-4.27 (m, 2H), 4.02-4.06 (m, 1H), 3.61-3.67 (m, 2H), 3.22-3.25 (m, 1H), 2.84-2.91 (m, 1H), 0.44-0.47 (m, 4H); ESI-MS m/z (M+H)$^+$ 512.2.

Embodiment 4: Preparation of Compound I-8

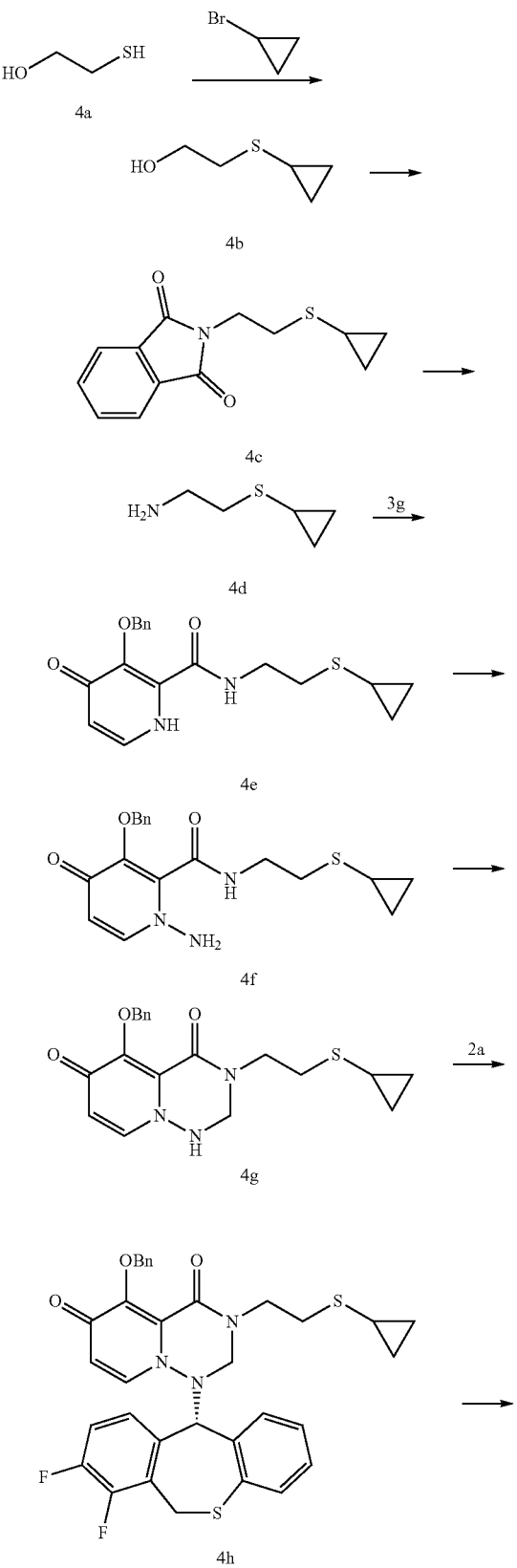

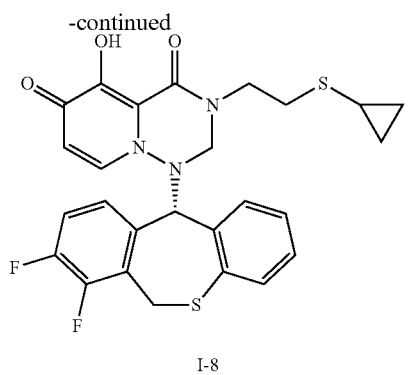

I-8

Preparation of Compound 4b: In 30 mL dimethyl sulfoxide, Compound 4a (2.24g, 28.7 mmol), bromocyclopropane (3.47g, 28.7 mmol) and potassium t-butoxide (3.22g, 28.7 mmol) were reacted at 80° C. overnight. The mixture was cooled to room temperature, and added with saturated NaHCO₃ solution to quench the reaction, and extracted with ethyl acetate (50 mL×3). The organic phases were combined, washed with brine, dried and concentrated to give 2.8 g yellow liquid. It was directly used in the next step.

Preparation of Compound 4c: In 20 mL tetrahydrofuran, Compound 4b (1.60g, 13.6 mmol), phthalimide (2.39 g, 16.2 mmol), triphenylphosphine (5.34 g, 20.4 mmol) and isopropyl azodicarboxylate (4.12 g, 20.4 mmol) were reacted at room temperature overnight. The mixture was added with water to quench the reaction, and extracted with ethyl acetate (20 mL×3). The organic phases were combined, washed with brine, dried and concentrated to give a crude product, which was separated by column chromatography to give 2.4 g oily product. It was directly used in the next step.

Preparation of Compound 4d: Compound 4c (2.40 g, 10 mmol) was dissolved in 30 mL methanol, 2 g hydrazine hydrate was added, and then the mixture was reacted at 75° C. for 2 hours. TLC showed the reaction was complete. The mixture was cooled and filtered. The filtrate was concentrated and triturated with ethyl ether. The mixture was filtered, and the filtrate was dried to give 1.04 g crude product. It was directly used in the next step.

Preparation of Compound 4e: In 10 mL dichloromethane, Compound 4d (420 mg, 3.6 mmol), Compound 3g (864 mg, 2.4 mmol), HATU (1.37 g, 3.6 mmol) and TEA (720 mg, 7.2 mmol) were stirred at room temperature over night. TLC showed the reaction was complete, and the mixture was added with 30 mL water and extracted with dichloromethane (30 mL×2), and the organic phases were combined, dried and concentrated to give a crude product, which was separated by silica gel plate to give 900 mg product. ESI-MS m/z (M+H)⁺ 344.1.

Preparation of Compound 4f: In 5 mL DMF, Compound 4e (900 mg, 2.4 mmol), potassium carbonate (1.08 g, 7.8 mmol) and 2,4-dinitrophenylhydroxylamine (780 mg, 3.9 mmol) were stirred at 60° C. for 5 hours. The mixture was added with 20 mL water and extracted with dichloromethane (20 mL×3), and the organic phases were combined, dried and concentrated to give a crude product, which was separated by silica gel plate to give 120 mg product.

Preparation of Compound 4g: Compound 4f (120 mg, 0.33 mmol), acetic acid (36 mg, 0.06 mmol) and paraformaldehyde (100 mg, 1.1 mmol) were refluxed in toluene for 6 hours. The mixture was concentrated, and the residue was added with 10 mL water and extracted with dichloromethane (20 mL×3), and the organic phases were combined, dried and concentrated to give a crude product, which was separated by silica gel plate to give 85 mg product.

Preparation of Compound 4h: In 2 mL solution of T3P in ethyl acetate, Compound 4g (85 mg, 0.23 mmol) and Compound 2a (90 mg, 0.34 mmol) were reacted at 100° C. for 3 hours in a pressured reactor. The mixture was cooled, diluted with saturated sodium bicarbonate, and then extracted with ethyl acetate. The organic phases were combined, dried and concentrated, and separated by column chromatography to give 20 mg product.

Preparation of Compound 1-8: In 1 mL DMA, Compound 4h (20 mg, 0.03 mmol) and lithium chloride (50 mg, 1.18 mmol) were reacted at 100° C. for 3 hours. After the reaction finished, the mixture was diluted with 10 mL water, and added with 2N hydrochloric acid to adjust pH to 3-4. The mixture was filtered, and the solid was dried under vacuum to give 5 mg product. ¹HNMR (400 MHz, CDCl₃) δ: 7.02-7.12 (m, 5H), 6.85 (m, 1H), 6.77 (m, 1H), 5.81 (d, 1H, J=7.6 Hz), 5.43 (m, 1H), 5.20 (s, 1H), 5.10 (d, 1H, J=12.8 Hz), 4.25 (d, 1H, J=12.8 Hz), 4.06 (d, 2H, J=14 Hz), 3.31 (m, 1H), 2.73 (t, 2H, J=6.8 Hz), 1.95 (m, 1H), 0.89 (m, 2H), 0.56 (m, 2H); ESI-MS m/z (M+H)⁺ 528.1.

Embodiment 5: Preparation of Compound I-14

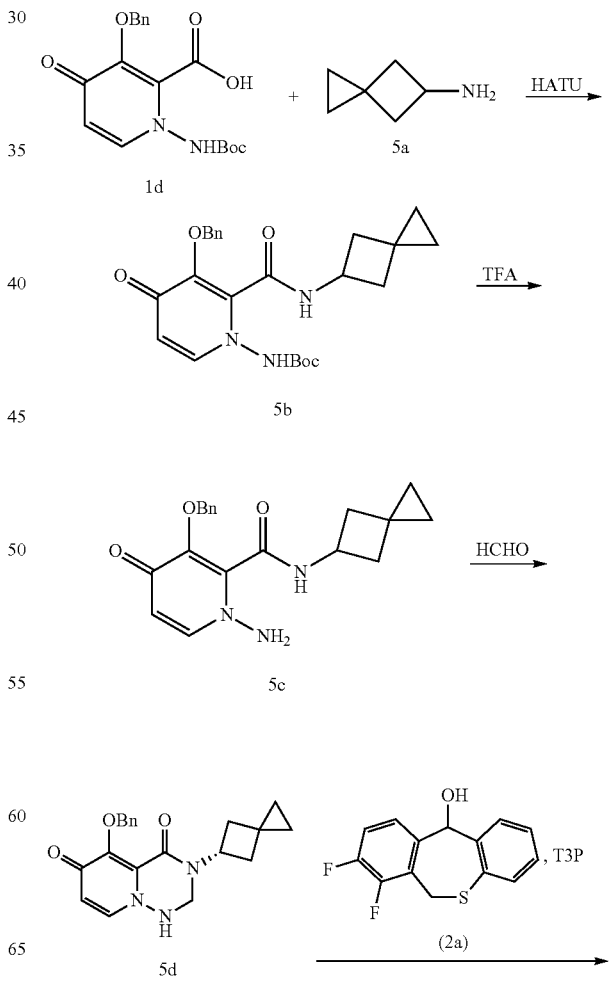

1H), 5.78 (d, 1H, J=7.6 Hz), 5.43 (d, 1H, J=12.8 Hz), 5.19 (t, 1H, J=7.6 Hz), 5.12 (s, 1H), 4.93 (d, 1H, J=13.2 Hz), 4.56 (d, 1H, J=13.6 Hz), 4.08 (d, 1H, J=14 Hz), 2.24 (m, 1H), 2.13 (m, 3H), 0.54 (t, 2H, J=8.0 Hz), 0.34 (m, 2H); ESI-MS m/z (M+H)⁺508.2.

With the same way, the following compounds were synthesized:

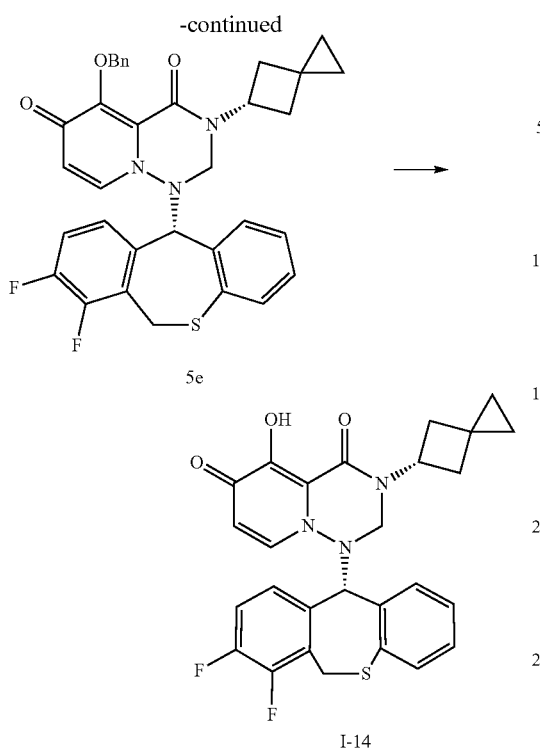

| Compound | Structure | LCMS ([M + H]⁺) | Purity |
|---|---|---|---|
| I-9 | 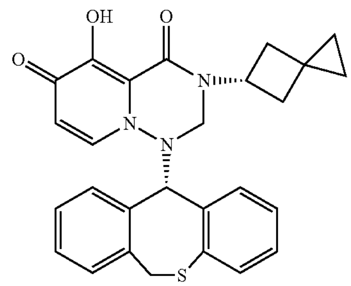 | 472.2 | 96% |
| I-10 | 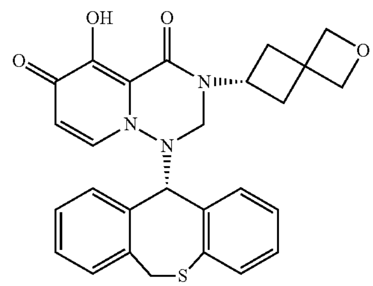 | 488.2 | 93% |
| I-21 | 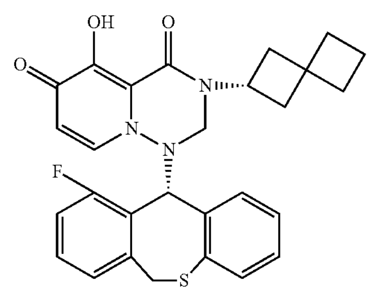 | 504.2 | 95% |

Preparation of Compound 5b: In DCM, Compound 1d (360 mg, 1 mmol), Compound 5a (116 mg, 1.2 mmol), TEA (303 mg, 3.0 mmol) and HATU (570 mg, 1.5 mmol) were stirred at room temperature overnight, then diluted with water, and extracted with DCM. The organic phases were combined, washed with brine, dried and concentrated, and separated by column chromatography to give 320 mg white solid.

Preparation of Compound 5c: Compound 5b (320 mg, 0.73 mmol) was dissolved in 4 mL DCM, added with 1 mL TFA, and reacted at 0° C. for 6 hours. The mixture was dried, added with 1N NaOH to adjust to be alkaline, and extracted with DCM/iPrOH. The organic phases were combined, washed with brine, dried and concentrated to give 195 mg oily product, which was directly used in the next step.

Preparation of Compound 5d: Compound 5c (195 mg, 0.57 mmol) was dissolved in 5 mL toluene, added with 30 mg paraformaldehyde and 100 mg acetic acid, and reacted at 100° C. for 3 hours. The mixture was concentrated and separated by thin layer chromatography to give 130 mg product.

Preparation of Compound 5e: In a solution of T3P in ethyl acetate, Compound 5d (130 mg, 0.37 mmol) and Compound 2a (114 mg, 0.5 mmol) were reacted at 100° C. for 3 hours in a pressured reactor. The mixture was cooled, diluted with saturated sodium bicarbonate, and then extracted with ethyl acetate. The organic phases were combined, dried and concentrated, and separated by silica gel plate to give 130 mg product.

Preparation of Compound 1-14: In 1 mL DMA, Compound 5e (130 mg, 0.23 mmol) and lithium chloride (50 mg, 1.18 mmol) were reacted at 100° C. for 3 hours. After the reaction finished, the mixture was diluted with 10 mL water, and added with 2N hydrochloric acid to adjust pH to 3-4. The mixture was filtered, and the solid was dried under vacuum to give 35 mg product. ¹HNMR (400 MHz, CDCl₃) δ: 7.03-7.11 (m, 4H), 6.94 (m, 1H), 6.82 (m, 1H), 6.67 (m, Embodiment 6: Preparation of Compound I-65

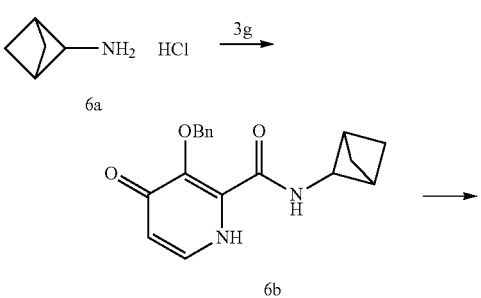

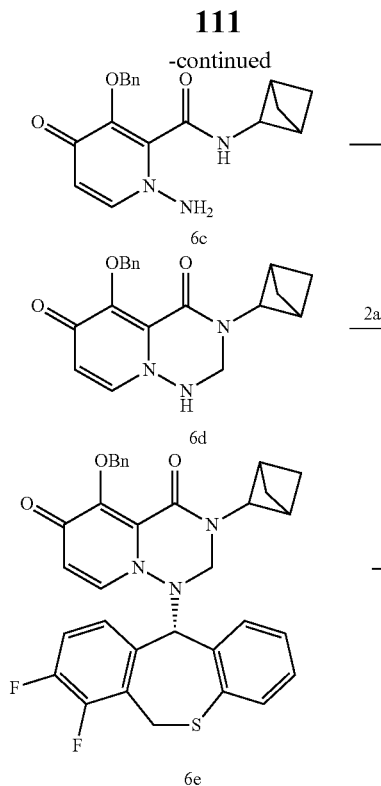

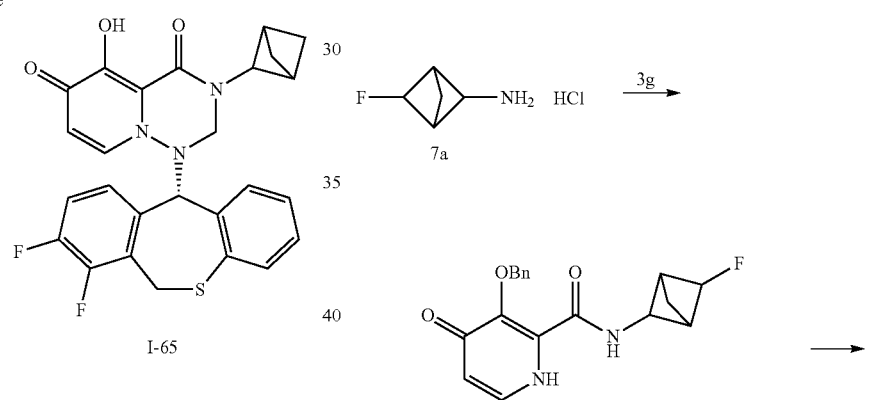

with 10 mL water and extracted with dichloromethane (20 mL×3), and the organic phases were combined, dried and concentrated to give a crude product, which was separated by column chromatography to give 190 mg product. ESI-MS m/z (M+H)$^+$ 338.1

Preparation of Compound 6e: In 3 mL solution of T3P in ethyl acetate, Compound 6d (190 mg, 0.56 mmol) and Compound 2a (223 mg, 0.84 mmol) were reacted at 100° C. for 1.5 hours in a pressured reactor. The mixture was cooled, diluted with water, and then extracted with ethyl acetate. The organic phases were combined, dried and concentrated, and separated by silica gel plate to give 227 mg product.

Preparation of Compound I-65: In 5 mL DMA, Compound 6e (227 mg, 0.4 mmol) and lithium chloride (86 mg, 2.0 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 100 mg product. $^1$HNMR (400 MHz, CDCl$_3$) δ: 7.10 (m, 3H), 6.99 (m, 2H), 6.84 (m, 1H), 6.70 (m, 1H), 5.75 (d, 1H, J=7.6 Hz), 5.40 (d, 1H, J=15.2), 5.14 (s, 1H), 4.82 (d, 1H, J=12.8 Hz), 4.25 (d, 1H, J=12.8 Hz), 4.04 (d, 1H, J=14.0 Hz), 3.76 (m, 3H), 2.98 (m, 2H), 2.54 (s, 1H), 2.05-2.15 (m, 6H); ESI-MS m/z (M+H)$^+$ 494.1.

Embodiment 7: Preparation of Compound I-66

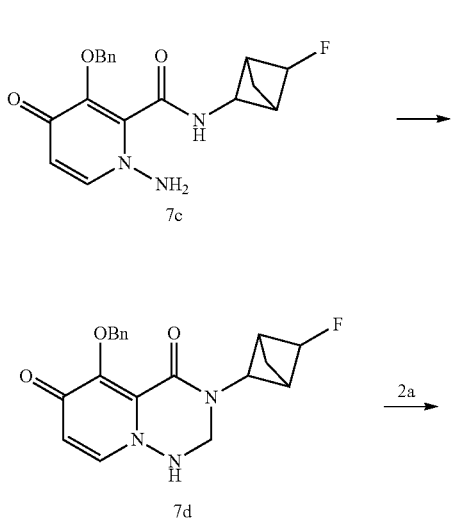

Preparation of Compound 6b: In 5 mL dichloromethane, Compound 6a (600 mg, 2.13 mmol), Compound 3g (280 mg, 2.34 mmol), HATU (1.21 g, 3.20 mmol) and TEA (850 mg, 8.5 mmol) were stirred at room temperature over night. TLC showed the reaction was complete, and the mixture was added with 20 mL water and extracted with dichloromethane (30 mL×3), and the organic phases were combined, dried and concentrated to give a crude product, which was separated by column chromatography to give 455 mg product.

Preparation of Compound 6c: In 15 mL DMF, Compound 6b (455 mg, 1.46 mmol), potassium carbonate (543 mg, 4.38 mmol) and 2,4-dinitrophenylhydroxylamine (392 mg, 2.19 mmol) were stirred at room temperature for 16 hours. TLC showed the reaction was complete, and the mixture was added with 20 mL water and extracted with dichloromethane (20 mL×3), and the organic phases were combined, dried and concentrated to give a crude product, which was separated by silica gel plate to give 200 mg product. ESI-MS m/z (M+H)$^+$ 326.1

Preparation of Compound 6d: Compound 6c (200 mg, 0.62 mmol), acetic acid (200 mg, 3.3 mmol) and paraformaldehyde (18 mg, 0.62 mmol) were refluxed in 10 mL toluene for 2 hours. TLC showed the reaction was complete. The mixture was concentrated, and the residue was added

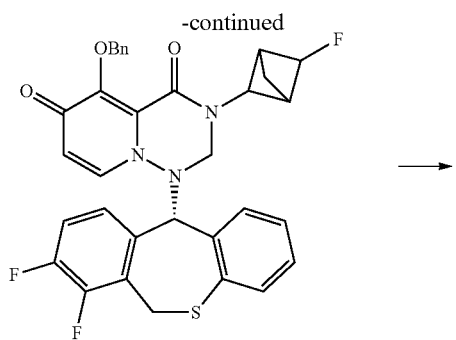

7e

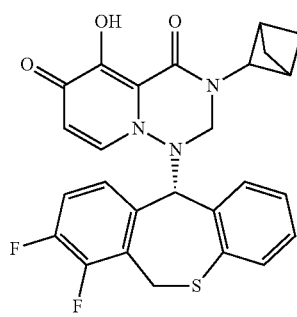

I-66

Preparation of Compound 7b: In 10 mL dichloromethane, Compound 7a (250 mg, 1.82 mmol), Compound 3g (465 mg, 1.65 mmol), HATU (941 mg, 2.48 mmol) and TEA (660 mg, 6.6 mmol) were stirred at room temperature over night. TLC showed the reaction was complete, and the mixture was added with 20 mL water and extracted with dichloromethane (30 mL×3), and the organic phases were combined, dried and concentrated to give a crude product, which was separated by column chromatography to give 430 mg product.

Preparation of Compound 7c: In 15 mL DMF, Compound 7b (430 mg, 1.30 mmol), potassium carbonate (538 mg, 3.9 mmol) and 2,4-dinitrophenylhydroxylamine (391 mg, 1.96 mmol) were stirred at room temperature for 16 hours. TLC showed the reaction was complete, and the mixture was added with 20 mL water and extracted with dichloromethane (20 mL×3), and the organic phases were combined, dried and concentrated to give a crude product, which was separated by silica gel plate to give 220 mg product. ESI-MS m/z (M+H)⁺ 344.1

Preparation of Compound 7d: Compound 7c (220 mg, 0.64 mmol), acetic acid (200 mg, 3.3 mmol) and paraformaldehyde (20 mg, 0.64 mmol) were refluxed in 10 mL toluene for 2 hours. TLC showed the reaction was complete. The mixture was concentrated, and the residue was added with 10 mL water and extracted with dichloromethane (20 mL×3), and the organic phases were combined, dried and concentrated to give a crude product, which was separated by silica gel plate to give 165 mg product. ESI-MS m/z (M+H)⁺ 356.1

Preparation of Compound 7e: In 3 mL solution of T3P in ethyl acetate, Compound 7d (165 mg, 0.46 mmol) and Compound 2a (184 mg, 0.70 mmol) were reacted at 100° C. for 1.5 hours in a pressured reactor. The mixture was cooled, diluted with water, and then extracted with ethyl acetate. The organic phases were combined, dried and concentrated, and separated by silica gel plate to give 100 mg product.

Preparation of Compound I-66: In 3 mL DMA, Compound 7e (100 mg, 0.17 mmol) and lithium chloride (35 mg, 0.83 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 45 mg product. ¹HNMR (400 MHz, CDCl₃) δ: 7.11 (m, 3H), 6.96 (m, 1H), 6.82 (m, 1H), 6.63 (m, 1H), 5.98 (d, 1H, J=9.2 Hz), 5.39 (m, 1H), 5.02-5.12 (m, 2H), 4.23 (d, 1H, J=12.8 Hz), 4.06 (d, 1H, J=14.0 Hz), 2.39-2.49 (m, 5H); ESI-MS m/z (M+H)⁺512.1

Embodiment 8: Preparation of Compound I-77

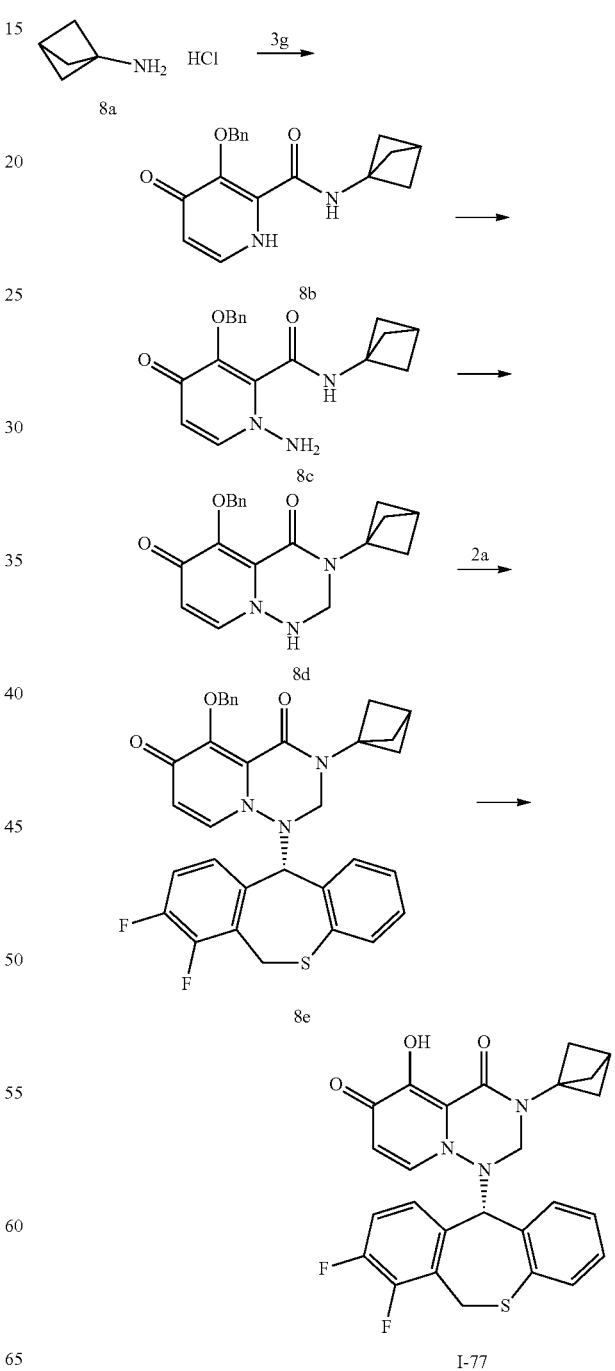

Preparation of Compound 8b: In 10 mL dichloromethane, Compound 8a (250 mg, 2.5 mmol), Compound 3g (705 mg, 2.5 mmol), HATU (1.19 g, 3.1 mmol) and TEA (1.01 g, 10.5 mmol) were stirred at room temperature over night. TLC showed the reaction was complete, and the mixture was added with 20 mL water and extracted with dichloromethane (30 mL×3), and the organic phases were combined, dried and concentrated to give a crude product, which was separated by column chromatography to give 780 mg product.

Preparation of Compound 8c: In 10 mL DMF, Compound 8b (780 mg, 2.5 mmol), potassium carbonate (1.04 g, 7.5 mmol) and 2,4-dinitrophenylhydroxylamine (752 mg, 3.8 mmol) were stirred at room temperature for 16 hours. TLC showed the reaction was complete, and the mixture was added with 20 mL water and extracted with dichloromethane (20 mL×3), and the organic phases were combined, dried and concentrated to give a crude product, which was separated by silica gel plate to give 390 mg product. ESI-MS m/z (M+H)$^+$ 326.1

Preparation of Compound 8d: Compound 8c (390 mg, 1.2 mmol), acetic acid (500 mg, 8.3 mmol) and paraformaldehyde (36 mg, 1.2 mmol) were refluxed in 10 mL toluene for 2 hours. TLC showed the reaction was complete. The mixture was concentrated, and the residue was added with 10 mL water and extracted with dichloromethane (20 mL×3), and the organic phases were combined, dried and concentrated to give a crude product, which was separated by silica gel plate to give 280 mg product. ESI-MS m/z (M+H)$^+$ 338.1

Preparation of Compound 8e: In 1.5 mL solution of T3P in ethyl acetate, Compound 8d (99 mg, 0.30 mmol) and Compound 2a (117 mg, 0.45 mmol) were reacted at 100° C. for 1.5 hours in a pressured reactor. The mixture was cooled, diluted with water, and then extracted with ethyl acetate. The organic phases were combined, dried and concentrated, and separated by silica gel plate to give 150 mg product.

Preparation of Compound I-77: In 3 mL DMA, Compound 8e (150 mg, 0.26 mmol) and lithium chloride (70 mg, 1.66 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 75 mg product. $^1$HNMR (400 MHz, CDCl$_3$) δ: 7.13-7.14 (m, 3H), 7.1-7.03 (d, 2H, J=8.0), 6.84-6.88 (m, 1H), 6.70-6.72 (d, 1H, J=8.0), 5.81-5.83 (d, 1H, J=8.0), 5.42-5.44 (m, 1H), 5.15 (s, 1H), 4.84-4.87 (m, 1H), 4.29-4.32 (m, 1H), 4.06-4.09 (m, 1H), 2.09-2.19 (m, 7H); ESI-MS m/z (M+H)$^+$ 494.1

With the same way, the following compounds were synthesized:

| Compound | Structure | LCMS ([M + H]$^+$) | Purity |
|---|---|---|---|
| I-69 | ![structure] | 458.2 | 95% |
| I-81 | ![structure] | 476.1 | 94% |
| I-83 | ![structure] | 476.2 | 97% |
| I-85 | ![structure] | 476.2 | 97% |
| I-89 | ![structure] | 492.1 | 96% |

Embodiment 9: Preparation of Compound II-5

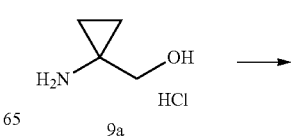

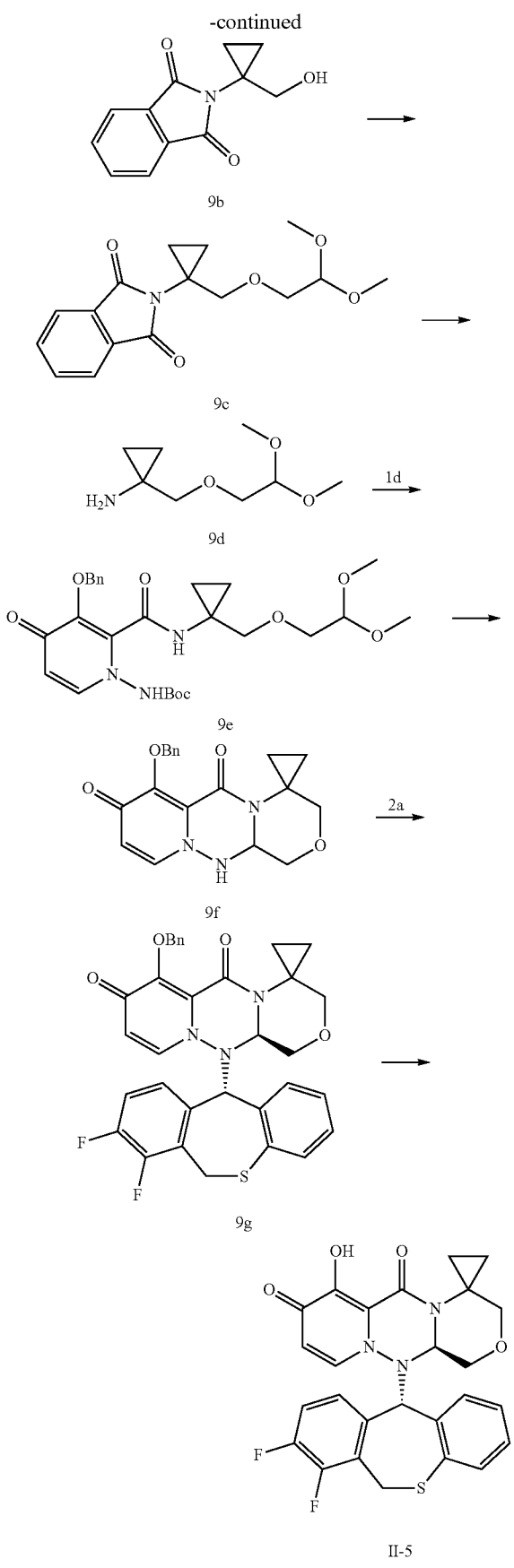

Preparation of Compound 9b: In a mixed solvent of DMF (7.5 ml) and toluene (7.5 ml), Compound 9a (250 mg, 2.02 mmol), phthalic anhydride (300 mg, 2.02 mmol), triethylamine (408 mg, 4.04 mmol) were reacted at 130° C. for 5 hours, and TLC showed the reaction was completed, and the mixture was added with water and stirred for 1 hour, and filtered to give 332 mg white solid, which was directly used in the next step.

Preparation of Compound 9c: Compound 9b (332 mg, 1.53 mmol) and bromoacetaldehyde dimethyl acetal (517 mg, 3.06 mmol) were dissolved in 15 ml DMA, heated to 40° C., and then added with sodium tert-butoxide (294 mg, 3.06 mmol), and the mixture was stirred at 40° C. for 5 hours. The mixture was cooled to room temperature, added with 10 mL water to quench the reaction, added with glacial acetic acid to adjust pH=3-4, extracted with ethyl acetate, dried, concentrated, and separated by column chromatography to give 265 mg product.

Preparation of Compound 9d: Compound 9c (265 mg, 0.87 mmol) was dissolved in 30 mL methanol, 2 g hydrazine hydrate was added, and then the mixture was reacted at 75° C. for 2 hours. TLC showed the reaction was complete. The mixture was cooled and filtered. The filtrate was concentrated and triturated with ethyl ether. The mixture was filtered, and the filtrate was dried to give 96 mg crude product. It was directly used in the next step.

Preparation of Compound 9e: In DCM, Compound 1d (137 mg, 0.38 mmol), Compound 9d (96 mg, 0.55 mmol), TEA (115 mg, 1.14 mmol) and HATU (289 mg, 0.76 mmol) were stirred at room temperature overnight, then diluted with water, and extracted with DCM. The organic phases were combined, washed with brine, dried and concentrated, and separated by column chromatography to give 155 mg product.

Preparation of Compound 9f: Compound 9e (155 mg, 0.3 mmol) was added with 18 mL acetonitrile and 3 mL water, and the mixture was heated to 60° C., dropwise added with methanesulfonic acid (8 mg, 0.9 mmol) and reacted for 6h. TLC showed the reaction was complete. The mixture was added with sodium bicarbonate aqueous solution to be weakly alkaline, concentrated and extracted with dichloromethane, and the organic phases were combined, dried, concentrated and separated by silica gel plate to give 60 mg white solid.

Preparation of Compound 9g: In a solution of T3P in ethyl acetate, Compound 9f (60 mg, 0.17 mmol) and Compound 2a (69 mg, 0.26 mmol) were reacted at 100° C. for 3 hours in a pressured reactor. The mixture was cooled, diluted with saturated NaHCO₃, and then extracted with ethyl acetate. The organic phases were combined, dried and concentrated, and separated by chiral column to give 15 mg product.

Preparation of Compound II-5: In 1 mL DMA, Compound 9g (15 mg, 0.025 mmol) and lithium chloride (10 mg, 0.24 mmol) were reacted at 100° C. for 3 hours. After the reaction finished, the mixture was diluted with 10 mL water, and added with 2N hydrochloric acid to adjust pH to 3-4. The mixture was filtered, and the solid was dried under vacuum to give 5 mg product. $^1$HNMR (400 MHz, CDCl$_3$) δ: 7.28-7.34 (m, 1H), 7.09-7.16 (m, 2H), 6.83-7.01 (m, 2H), 6.66-6.68 (d, 1H, J=8.0); 6.56-6.59 (m, 1H), 5.77-5.90 (m, 1H), 5.28-5.37 (m, 1H), 5.02-5.18 (m, 1H), 4.61-4.71 (m, 1H), 3.91-4.17 (m, 3H), 3.59-3.68 (m, 1H), 2.95-3.07 (m, 1H), 0.23-0.89 (m, 4H); ESI-MS m/z (M+H)$^+$ 510.1.

With the same way, the following compounds were synthesized:
| Compound | Structure | LCMS ([M + H]+) | Purity |
|---|---|---|---|
| II-1 | 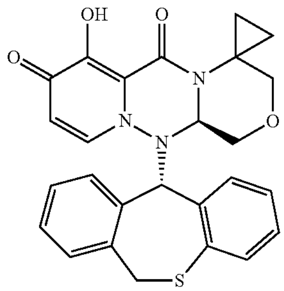 [SMILES: O=C1c2c(O)c(=O)ccn2N([C@H]2c3ccccc3CSc3ccccc32)[C@@H]2COCC3(CC3)N12] | 474.2 | 95% |
| II-8 | 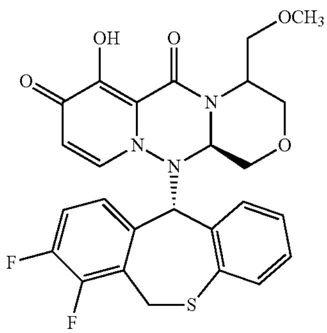 | 528.1 | 94% |
| II-9 | 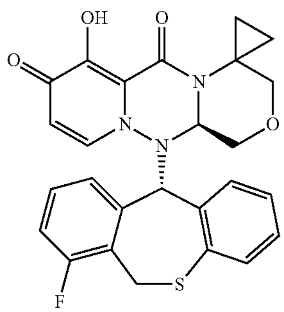 [SMILES: O=C1c2c(O)c(=O)ccn2N([C@@H]2c3ccccc3SCc3c(F)cccc32)[C@@H]2COCC3(CC3)N12] | 492.1 | 94% |
| II-13 | 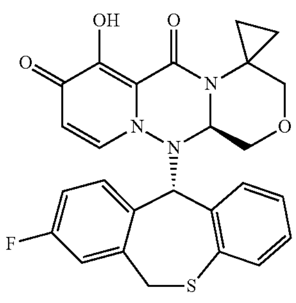 [SMILES: O=C1c2c(O)c(=O)ccn2N([C@H]2c3ccc(F)cc3CSc3ccccc32)[C@@H]2COCC3(CC3)N12] | 492.1 | 95% |
| II-17 | 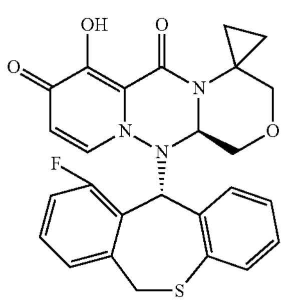 [SMILES: O=C1c2c(O)c(=O)ccn2N([C@@H]2c3ccccc3SCc3cccc(F)c32)[C@@H]2COCC3(CC3)N12] | 492.1 | 96% |
Embodiment 10: Preparation of Compound II-6
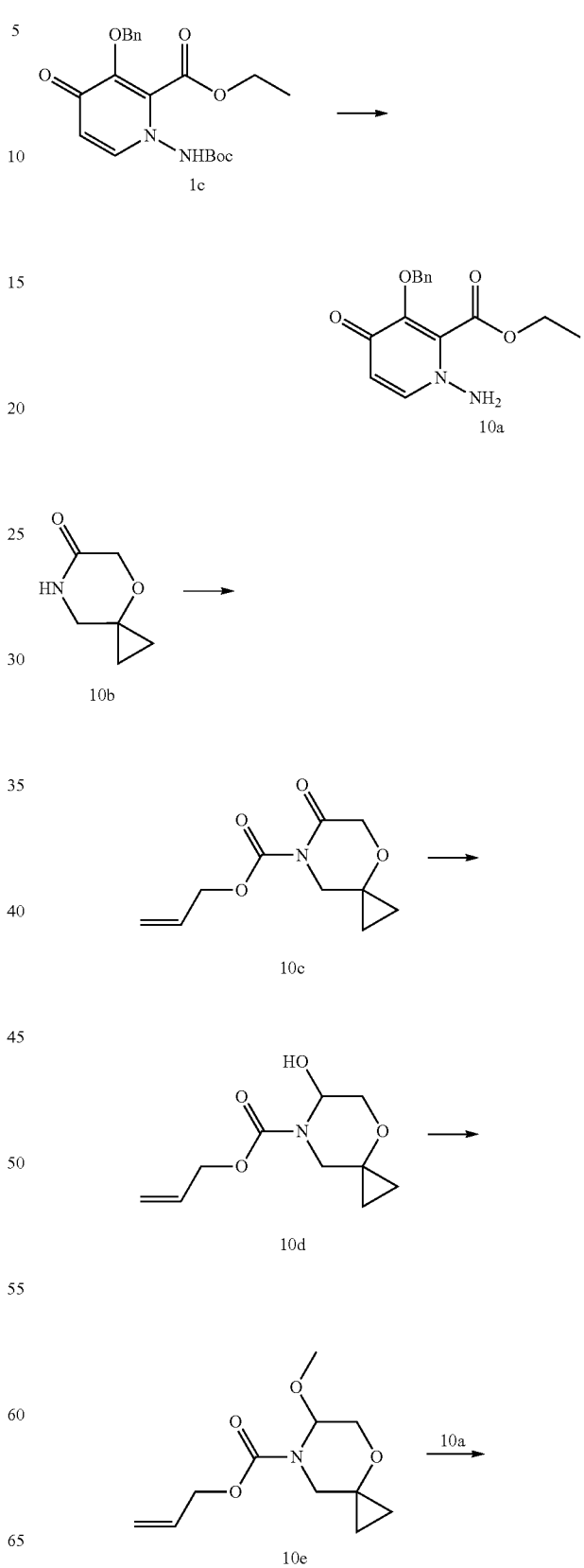

-continued

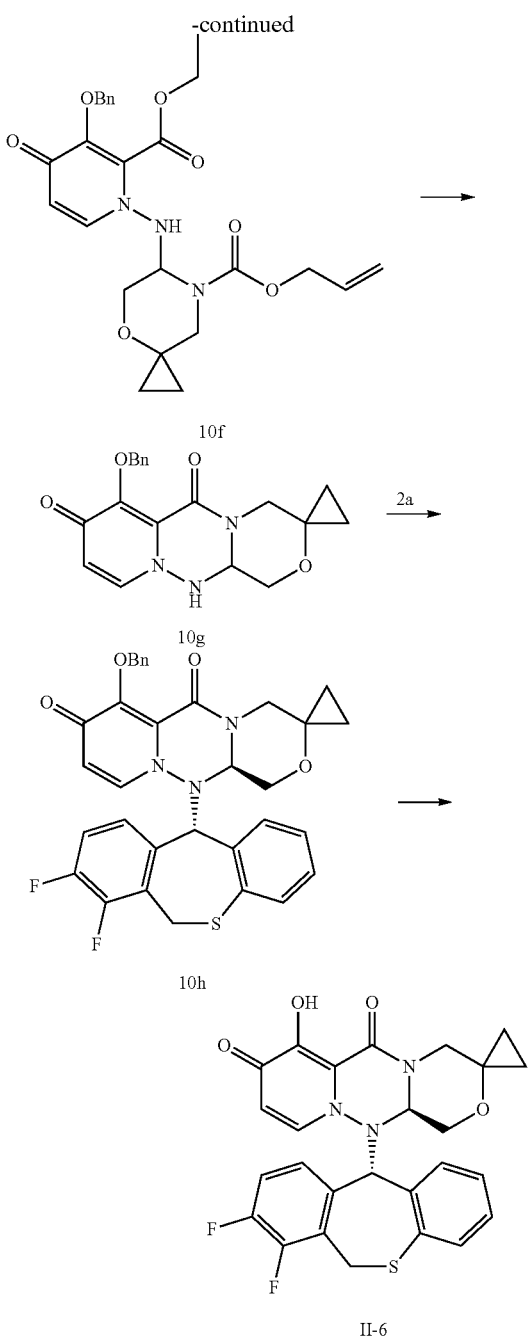

Preparation of Compound 10a: Compound 1c (388 mg, 1 mmol) was dissolved in 3 mL dichloromethane and added with 1 mL trifluoroacetic acid, and the mixture was stirred at room temperature for 3 hours. TLC showed the reaction was complete, and the mixture was added with 3N sodium hydroxide solution to adjust pH=9-10. The mixture was extracted with dichloromethane, and organic phases were combined, washed with brine, dried and concentrated to give 270 mg solid, which was directly used in the next step.

Preparation of Compound 10c: Compound 10b (1.0 g, 7.8 mmol) was dissolved in 10 mL anhydrous tetrahydrofuran and replaced with nitrogen for three times. The mixture was cooled to −78° C. and 2.5M n-butyllithium solution (3.1 mL, 7.8 mmol) was added slowly under nitrogen protection. After addition, the mixture was stirred at this temperature for 2 hours. Then allyl chloroformate (0.94 g, 7.8 mmol) was added by dropwise. After addition, the mixture was stirred at this temperature for 2 hours, and TLC showed the starting materials were completely reacted. The reaction mixture was poured into saturated ammonium chloride solution, and extracted with ethyl acetate (15 mL×3). The organic phases were combined, dried over anhydrous sodium sulfate and concentrated to give 1.65g oily product.

Preparation of Compound 10d: Compound 10c (1.65 g, 7.8 mmol) was dissolved in 15 mL anhydrous tetrahydrofuran, and 1M diisobutylaluminum hydride solution (11.7 mL, 11.7 mmol) was added slowly at −78° C. under nitrogen protection. After addition, the mixture was stirred at this temperature for 2 hours. TLC showed the starting materials were completely reacted. The reaction mixture was poured into saturated ammonium chloride solution, and extracted with ethyl acetate (20 mL×3). The organic phases were combined, dried over anhydrous sodium sulfate and concentrated to give 1.57g oily product.

Preparation of Compound 10e: Compound 10d (1.57 g, 7.4 mmol) was dissolved in 15 mL methanol, and p-toluenesulfonic acid monohydrate (140 mg, 0.74 mmol) was added. The mixture was stirred at room temperature overnight. TLC showed the starting materials were completely reacted. The mixture was added with saturated sodium bicarbonate solution till neutral, then concentrated. The residue was separated by column chromatography to give 0.86 g yellow oily product.

Preparation of Compound 10f: Compound 10a (270 mg, 0.94 mmol) and Compound 10e (255 mg, 1.13 mmol) were dissolved in 5 mL acetonitrile. Under nitrogen protection and at −20° C., 1M solution of tin tetrachloride in dichloromethane (1.4 mL, 1.41 mmol) was added dropwise. After addition, the mixture was stirred at this temperature for 3 hours. The mixture was added with saturated sodium bicarbonate solution, stirred for 30 min, and separated, The aqueous phase was extracted with dichloromethane. The organic phases were combined, washed with brine, dried and concentrated to give 428 mg crude product.

Preparation of Compound 10g: Compound 10f (428 mg, 0.89 mmol) was dissolved in 5 mL tetrahydrofuran, and tetrakis(triphenylphosphine)palladium (104 mg, 0.09 mmol) and morpholine (774 mg, 8.9 mmol) were added and reacted at room temperature for 2 hours. TLC showed the reaction was complete. The mixture was concentrated, and the residue was separated by column chromatography to give 216 mg product.

Preparation of Compound 10h: In 3 mL solution of T3P in ethyl acetate, Compound 10g (216 mg, 0.61 mmol) and Compound 2a (242 mg, 0.92 mmol) were reacted at 100° C. for 3 hours in a pressured reactor. The mixture was cooled, diluted with saturated NaHCO$_3$, and then extracted with ethyl acetate. The organic phases were combined, dried and concentrated, and separated by column chromatography to give 200 mg crude product, which was separated by chiral column to give 40 mg product.

Preparation of Compound II-6: In 1 mL DMA, Compound 10h (40 mg, 0.067 mmol) and lithium chloride (20 mg, 0.48 mmol) were reacted at 100° C. for 3 hours. After the reaction finished, the mixture was diluted with 10 mL water, and added with 2N hydrochloric acid to adjust pH to 3-4. The mixture was filtered, and the solid was dried under vacuum to give 25 mg product. $^1$HNMR (400 MHz, CDCl$_3$) δ: 7.05-7.15 (m, 5H), 6.85 (m, 1H), 6.70 (d, 1H, J=7.6 Hz), 5.78 (d, 1H, J=7.6 Hz), 5.3 (m, 2H), 4.69 (d, 1H, J=6.8 Hz), 4.17 (d, 1H, J=14 Hz), 4.09 (d, 1H, J=14 Hz), 3.90 (m, 1H), 3.69 (m, 1H), 3.44 (d, 1H, J=15.2 Hz), 0.95 (m, 1H), 0.74 (m, 3H); ESI-MS m/z (M+H)$^+$ 510.1.

With the same way, the following compounds were synthesized:

| Compound | Structure | LCMS ([M + H]+) | Purity |
|---|---|---|---|
| II-2 | 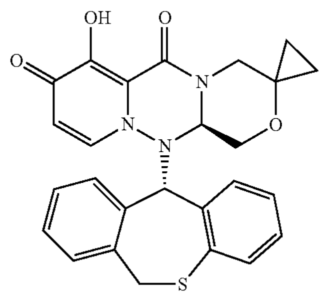 [SMILES: O=C1c2c(O)c(=O)ccn2N([C@H]2c3ccccc3CSc3ccccc32)[C@@H]2COC3(CC3)CN12] | 474.2 | 95% |
| II-7 | 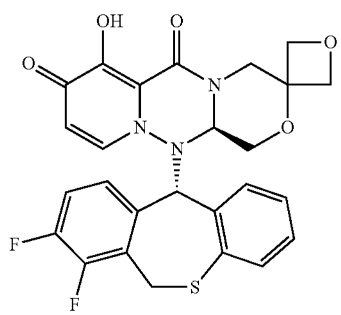 [SMILES: O=C1c2c(O)c(=O)ccn2N([C@@H]2c3ccccc3SCc3c2ccc(F)c3F)[C@@H]2COC3(COC3)CN12] | 526.2 | 94% |
| II-10 | 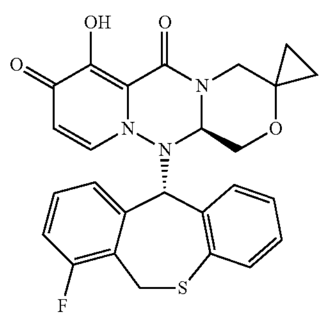 [SMILES: O=C1c2c(O)c(=O)ccn2N([C@@H]2c3ccccc3SCc3c(F)cccc32)[C@@H]2COC3(CC3)CN12] | 492.1 | 95% |
| II-14 | 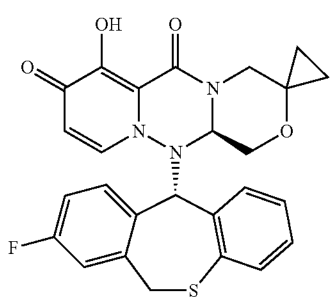 [SMILES: O=C1c2c(O)c(=O)ccn2N([C@H]2c3ccc(F)cc3CSc3ccccc32)[C@@H]2COC3(CC3)CN12] | 492.1 | 96% |
| II-18 | 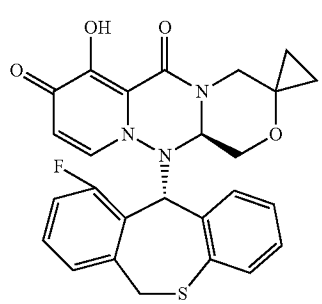 [SMILES: O=C1c2c(O)c(=O)ccn2N([C@@H]2c3ccccc3SCc3cccc(F)c32)[C@@H]2COC3(CC3)CN12] | 492.1 | 95% |

125
-continued
| Compound | Structure | LCMS ([M + H]+) | Purity |
|---|---|---|---|
| II-22 | 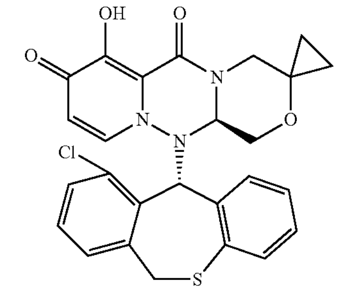 | 508.1 | 96% |
| II-29 | 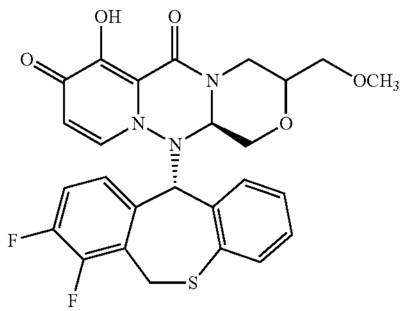 | 528.1 | 96% |
Embodiment 11: Preparation of Compound II-66
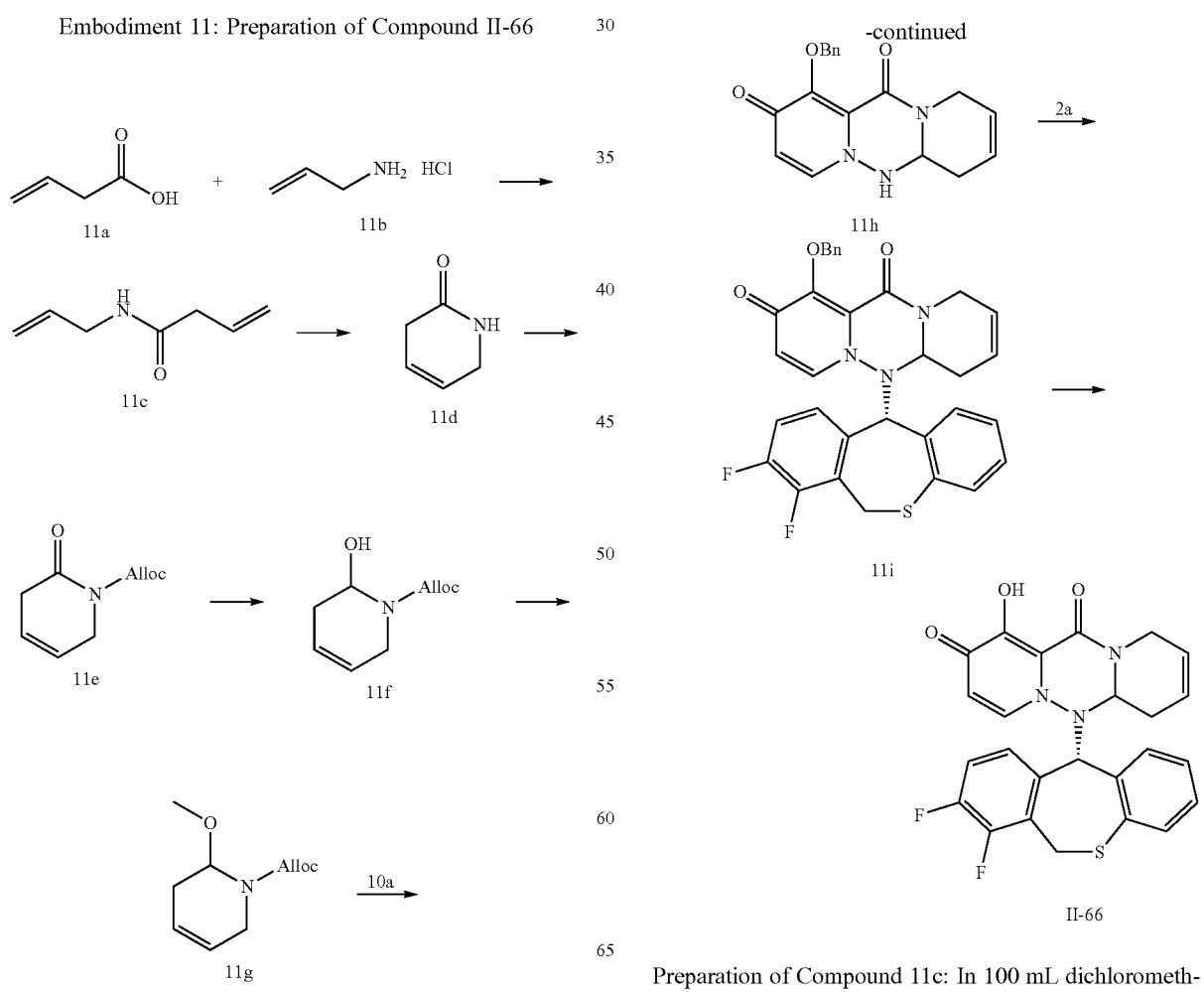
Preparation of Compound 11c: In 100 mL dichloromethane, Compound 11a (5.00 g, 58 mmol), Compound 11b (5.98 g, 64 mmol), HATU (33.0 g, 87 mmol) and DIPEA (30 mL, 174 mmol) were stirred at room temperature overnight. TLC showed the reaction was complete, and the mixture was added with 100 mL water and extracted with dichloromethane (30 mL×3), and the organic phases were combined, dried and concentrated to give a crude product, which was separated by column chromatography to give 6.0g product.

Preparation of compound IId: Compound 11c (1.00 g, 8.0 mmol) was dissolved in 240 mL dichloromethane, then added Grubbs II catalyst (260 mg, 0.32 mmol), and refluxed for 12 hours under nitrogen protection. TLC showed the reaction was complete, and the mixture was concentrated to give a crude product, which was separated by column chromatography to give 150 mg product.

Preparation of Compound 11e: Compound 11d (150 mg, 1.54 mmol) was dissolved in 4 mL anhydrous tetrahydrofuran, and replaced with nitrogen for three times. The mixture was cooled to −78° C. and 2.5M n-butyllithium solution (0.62 mL, 1.54 mmol) was added slowly under N2 atmosphere. After addition, the mixture was stirred at this temperature for 2 hours. Then allyl chloroformate (186 mg, 1.54 mmol) was added by dropwise. After addition, the mixture was stirred for 2 hours, and TLC showed reaction complete. The reaction mixture was poured into saturated ammonium chloride solution and then extracted with ethyl acetate (15 mL×3). The organic phases were combined, dried over anhydrous sodium sulfate and concentrated to give 235 mg oily product.

Preparation of Compound 11f: Compound 11e (235 mg, 1.3 mmol) was dissolved in 3 mL anhydrous tetrahydrofuran, and 1M diisobutylaluminum hydride solution (1.7 mL, 1.7 mmol) was added slowly at −78° C. under nitrogen protection. After addition, the mixture was stirred at this temperature for 2 hours. TLC showed reaction complete. The reaction mixture was poured into saturated potassium sodium tartrate solution, and extracted with ethyl acetate (20 mL×3). The organic phases were combined, dried over anhydrous sodium sulfate and concentrated to give 200 mg oily product.

Preparation of Compound 11g: Compound 11f (200 mg, 1.1 mmol) was dissolved in 3 mL methanol, and p-toluenesulfonic acid monohydrate (21 mg, 0.11 mmol) was added, and the mixture was stirred at room temperature for 5 hours. TLC showed reaction complete. The mixture was added with saturated sodium bicarbonate solution till neutral, and extracted with dichloromethane (20 mL×3). The organic phases were combined, dried over anhydrous sodium sulfate and concentrated to give a crude product, which was separated by column chromatography to give 180 mg oily product.

Preparation of Compound 11h: Compound 11g (180 mg, 0.65 mmol) and Compound 10a (150 mg, 0.75 mmol) were dissolved in 15 mL acetonitrile. Under nitrogen protection and at −20° C., 1M solution of tin tetrachloride in dichloromethane (0.95 mL, 0.95 mmol) was added dropwise. After addition, the mixture was stirred at this temperature for 3 hours. The mixture was added with saturated sodium bicarbonate solution, stirred for 30 min, and separated. The aqueous phase was extracted with dichloromethane. The organic phases were combined, washed with brine, dried and concentrated to give 300 mg solid. The solid was dissolved in 5 mL tetrahydrofuran, and tetrakis(triphenylphosphine)palladium (55 mg, 0.065 mmol) and morpholine (5 g, 55 mmol) were added and reacted at room temperature for 2 hours. TLC showed the reaction was complete. The mixture was concentrated, and the residue was separated by column chromatography to give 150 mg product.

Preparation of Compound 11i: In 3 mL solution of T3P in ethyl acetate, Compound 11h (70 mg, 0.22 mmol) and Compound 2a (86 mg, 0.32 mmol) were reacted at 100° C. for 1.5 hours in a pressured reactor. The mixture was cooled, diluted with saturated NaHCO$_3$, and extracted with ethyl acetate. The organic phases were combined, dried and concentrated, and separated by column chromatography to give 100 mg crude product.

Preparation of Compound II-66: In 3 mL DMA, Compound 11i (100 mg, 0.18 mmol) and lithium chloride (37 mg, 0.88 mmol) were reacted at 100° C. for 3 hours. After the reaction finished, the mixture was diluted with 10 mL water, and 2N hydrochloric acid was added to adjust pH to 3-4. The mixture was filtered, and the solid was dried under vacuum to give 30 mg product. $^1$HNMR (400 MHz, CDCl$_3$) δ: 7.28 (d, 2H, J=8.0 Hz), 7.21 (m, 1H), 7.05-7.15 (m, 5H), 6.98-7.01 (m, 1H), 6.91 (q, 1H, J=8.4 Hz), 6.85 (m, 1H), 6.69 (m, 1H), 6.63 (m, 1H), 5.88 (d, 1H, J=7.6 Hz), 5.78 (d, 1H, J=7.6 Hz), 5.69 (m, 4H), 5.46 (m, 1H), 5.32 (m, 1H), 5.28 (s, 1H), 5.15 (s, 1H), 5.03 (m, 2H), 4.62 (dd, 1H, J=3.6, 11.2 Hz), 4.49 (dd, 1H, J=4.0, 10.8 Hz), 4.07 (t, 2H, J=14.4 Hz), 3.44 (d, 1H, J=18.8 Hz), 3.27 (m, 1H), 2.57 (m, 2H), 2.30 (m, 2H); ESI-MS m/z (M+H)$^+$ 480.1.

With the same way, the following compounds were synthesized:

| Compound | Structure | LCMS ([M + H]$^+$) | Purity |
|---|---|---|---|
| II-34 | 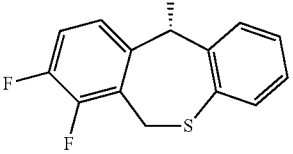 | 538.2 | 96% |

| Compound | Structure | LCMS ([M + H]+) | Purity |
|---|---|---|---|
| II-65 | 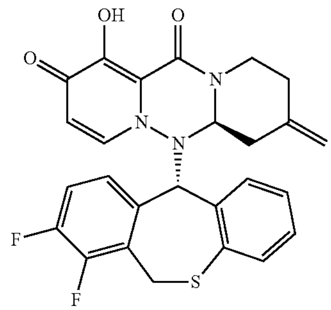 [SMILES: C=C1CCN2C(=O)c3c(O)c(=O)ccn3N([C@@H]3c4ccccc4SCc4c3ccc(F)c4F)[C@@H]2C1] | 494.1 | 94% |
| II-67 | 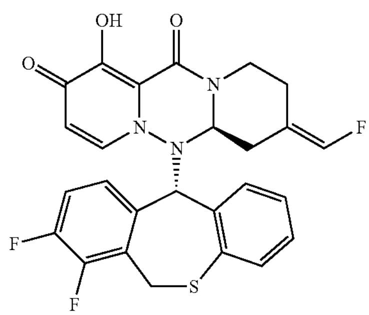 [SMILES: O=C1c2c(O)c(=O)ccn2N([C@@H]2c3ccccc3SCc3c2ccc(F)c3F)[C@@H]2C/C(=C/F)CCN12] | 512.2 | 93% |
Embodiment 12: Preparation of Compound II-101
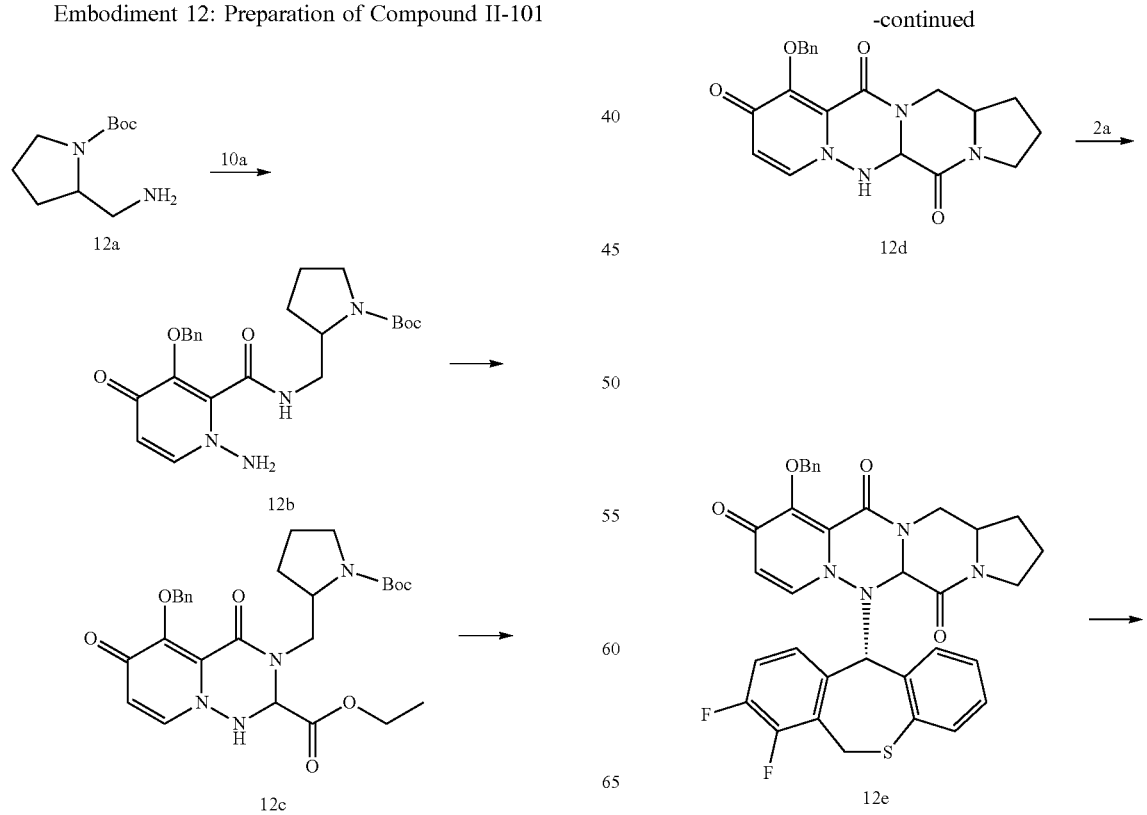

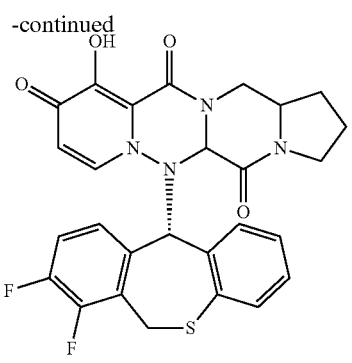

II-101

Preparation of Compound 12b: In 10 mL tetrahydrofuran, Compound 12a (520 mg, 2.6 mmol), Compound 10a (570 mg, 2.0 mmol) and DBU (490 mg, 3.3 mmol) were stirred at 55° C. overnight. The mixture was concentrated, added with 30 mL water and extracted with ethyl acetate (30 mL×3), and the organic phases were combined, dried and concentrated to give a crude product, which was separated by column chromatography to give 720 mg product.

Preparation of Compound 12c: Compound 12b (720 mg, 1.6 mmol), ethyl glyoxalate (50% toluene solution, 1.66 g, 8.3 mmol) and acetic acid (20 mg, 0.3 mmol) were refluxed in 10 mL toluene for 6 hours. After the reaction was complete, the mixture was diluted with 30 mL ethyl acetate, and washed with sodium bicarbonate solution and brine. The organic phases were dried and concentrated to give a crude product, which was separated by column chromatography to give 450 mg product.

Preparation of Compound 12d: Compound 12c (400 mg, 0.76 mmol) was dissolved in 15 mL dichloromethane and added with 5 mL trifluoroacetic acid, and the mixture was stirred at room temperature for 2 hours. The mixture was dried and added with 10 mL water, cooled in ice-water bath, added with saturated sodium bicarbonate solution to pH=9-10, and stirred at room temperature overnight. The reaction solution was extracted with dichloromethane and the organic phases were dried and separated by silica gel plate to give 150 mg product.

Preparation of Compound 12e: In 6 mL solution of T3P in ethyl acetate, Compound 12d (150 mg, 0.39 mmol) and Compound 2a (156 mg, 059 mmol) were reacted at 100° C. for 1.5 hours in a pressured reactor. The mixture was cooled, diluted with water, and then extracted with ethyl acetate. The organic phases were combined, dried and concentrated, and separated by silica gel plate to give 100 mg product.

Preparation of Compound I-101: In 1 mL DMA, Compound 12e (100 mg, 0.16 mmol) and lithium chloride (35 mg, 0.83 mmol) were reacted at 100° C. for 3 hours. After the reaction finished, the mixture was diluted with 10 mL water, and added with 2N hydrochloric acid to adjust pH to 5-6. The mixture was filtered, and the solid was dried under vacuum to give 27 mg product. $^1$HNMR (400 MHz, CDCl$_3$) δ: 7.72 (d, 1H, J=6.0 Hz), 7.30 (m, 1H), 7.10-7.17 (m, 2H), 6.85-7.02 (m, 2H), 6.66-6.78 (m, 1H), 6.38-6.51 (m, 1H), 6.19 (d, 1H, J=6.0 Hz), 5.09 (m, 1H), 4.74 (m, 1H), 4.55 (m, 1H), 4.42 (m, 1H), 3.84-4.00 (m, 2H), 3.73 (m, 2H), 3.60 (m, 2H), 3.40 (m, 2H), 2.88 (m, 1H), 1.84 (m, 1H), 1.52 (m, 2H); ESI-MS m/z (M+H)$^+$ 537.2.

Embodiment 13: Preparation of Compound III-1

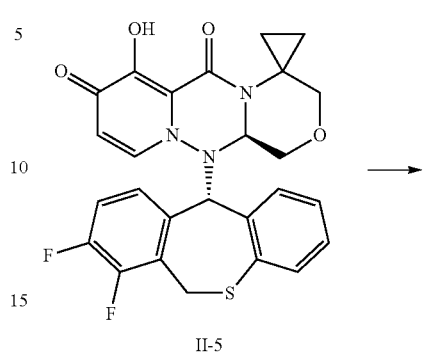

II-5

III-1

Preparation of Compound III-1: In 1 mL N,N-dimethylacetamide, Compound II-5 (50 mg, 0.1 mmol), chloromethyl methyl carbonate (25 mg, 0.2 mmol), potassium carbonate (28 mg, 0.2 mmol) and potassium iodide (3 mg, 0.02 mmol) were reacted at 60° C. for 5 hours. TLC showed the reaction was complete, and the mixture was added with water to quench. 1N hydrochloric acid was added to adjust pH to 3-4. The solid was filtered, dried, and separated by column chromatography to give 48 mg product. $^1$HNMR (400 MHz, DMSO-d6) δ: 7.37-7.44 (m, 2H), 7.13-7.18 (m, 2H), 7.10 (m, 1H), 6.93 (m, 1H), 6.85 (t, 1H, J=7.6 Hz), 5.75 (m, 1H), 5.70 (m, 1H), 5.66 (m, 2H), 5.43 (d, 1H, J=14.8 Hz), 4.43 (dd, 1H, J=2.4, 9.6 Hz), 4.10 (dd, 1H, J=2.8, 10.8 Hz), 4.07 (d, 1H, J=14.4 Hz), 3.75 (d, 1H, J=12.0 Hz), 3.72 (s, 3H), 3.44 (m, 1H), 3.02 (d, 1H, J=11.2 Hz), 1.76 (m, 1H), 1.13 (m, 1H), 0.48 (m, 1H), 0.24 (m, 1H); ESI-MS m/z (M+H)$^+$ 598.1.

133

Embodiment 14: Preparation of Compound III-2

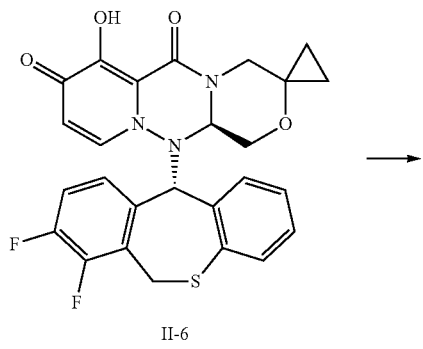

II-6

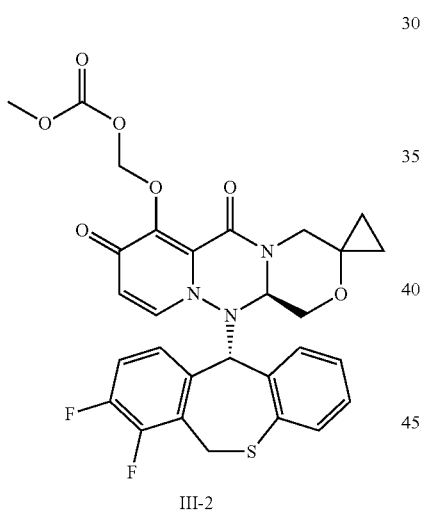

III-2

Preparation of Compound III-2: In 1 mL N,N-dimethylacetamide, Compound 11-6 (40 mg, 0.08 mmol), chloromethyl methyl carbonate (25 mg, 0.2 mmol), potassium carbonate (28 mg, 0.2 mmol) and potassium iodide (3 mg, 0.02 mmol) were reacted at 60° C. for 5 hours. TLC showed the reaction was complete, and the mixture was added with water to quench. 1N hydrochloric acid was added to adjust pH to 3-4. The solid was filtered, dried, and separated by column chromatography to give 35 mg product. $^1$HNMR (400 MHz, DMSO-d6) δ: 7.40-7.42 (m, 2H), 7.25 (d, 1H, J=7.6 Hz), 7.15 (m, 1H), 7.10 (m, 1H), 7.00 (d, 1H, J=7.2 Hz), 6.84 (t, 1H, J=7.6 Hz), 5.75 (m, 4H), 5.43 (d, 1H, J=16.4 Hz), 4.57 (dd, 1H, J=3.2, 9.6 Hz), 3.96-4.03 (m, 3H), 3.73 (s, 3H), 3.51 (t, 1H, J=10.0 Hz), 3.41 (s, 1H), 0.75 (t, 2H, J=8.4 Hz), 0.50 (m, 2H); ESI-MS m/z (M+H)$^+$ 598.1.

134

Embodiment 15: Preparation of Compound III-57

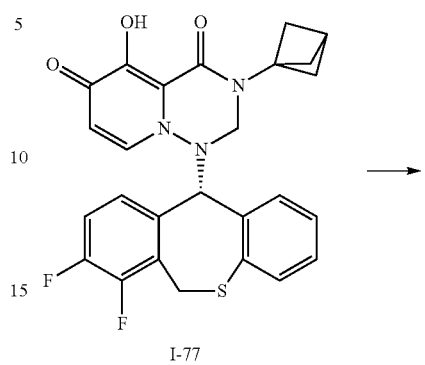

I-77

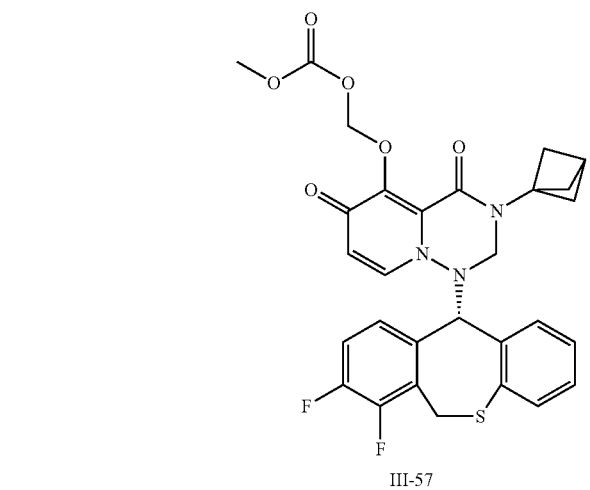

III-57

Preparation of Compound III-57: In 1 mL N,N-dimethylacetamide, Compound 1-77 (49 mg, 0.1 mmol), chloromethyl methyl carbonate (25 mg, 0.2 mmol), potassium carbonate (28 mg, 0.2 mmol) and potassium iodide (3 mg, 0.02 mmol) were reacted at 60° C. for 5 hours. TLC showed the reaction was complete, and the mixture was added with water to quench. 1N hydrochloric acid was added to adjust pH to 3-4. The solid was filtered, dried, and separated by column chromatography to give 43 mg product. $^1$HNMR (400 MHz, DMSO-d6) δ: 7.40 (m, 2H), 7.16 (m, 3H), 6.91 (m, 2H), 5.83 (d, 1H, J=7.2 Hz), 5.74 (m, 1H), 5.57 (m, 1H), 5.44 (m, 1H), 5.29 (s, 1H), 4.94 (d, 1H, J=13.6 Hz), 4.21 (d, 1H, J=14.4 Hz), 3.74 (s, 3H), 2.45 (s, 1H), 2.05 (m, 4H), 1.93 (m, 2H); ESI-MS m/z (M+H)$^+$582.1.

With the same way, the following compounds were synthesized:
| Compound | Structure | LCMS ([M + H]+) | Purity |
|---|---|---|---|
| III-3 | 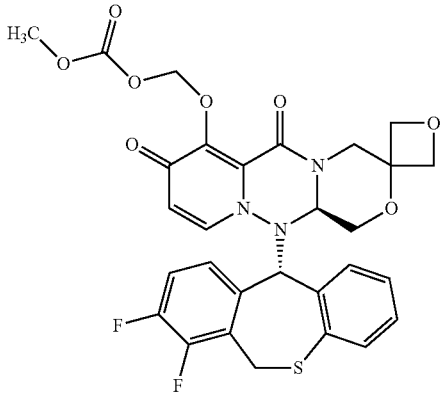 [SMILES: COC(=O)OCOc1c2n(ccc1=O)N([C@@H]1c3ccccc3SCc3c1ccc(F)c3F)[C@@H]1COC3(COC3)CN1C2=O] | 614.2 | 93% |
| III-4 | 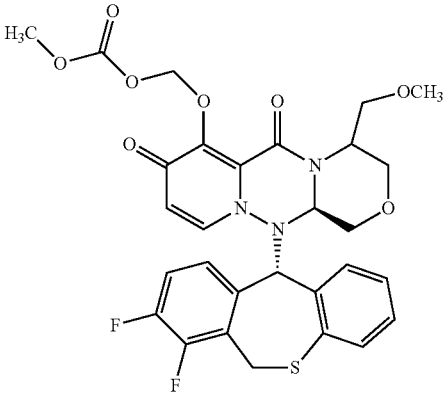 | 616.2 | 97% |
| III-5 | 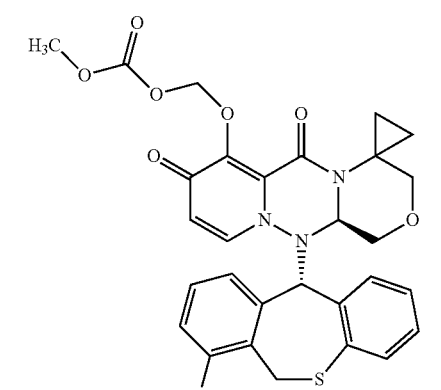 | 580.2 | 95% |

| Compound | Structure | LCMS ([M + H]+) | Purity |
|---|---|---|---|
| III-6 | 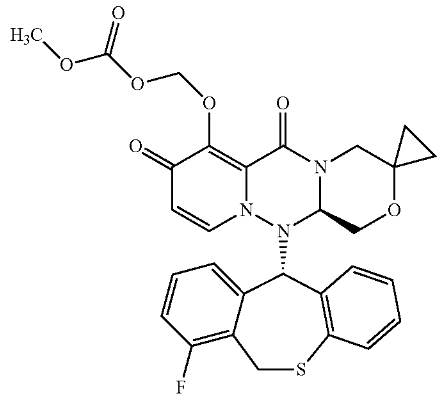 [SMILES: COC(=O)OCOc1c2n(ccc1=O)N([C@@H]1c3ccccc3SCc3c(F)cccc31)[C@@H]1COC3(CC3)CN1C2=O] | 580.2 | 95% |
| III-9 | 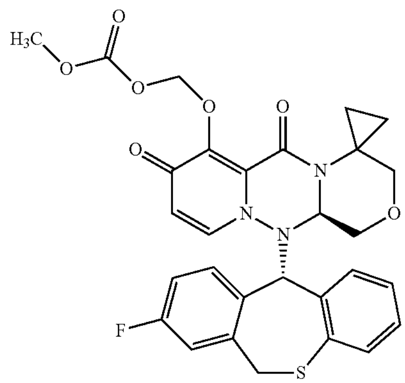 [SMILES: COC(=O)OCOc1c2n(ccc1=O)N([C@H]1c3ccc(F)cc3CSc3ccccc31)[C@@H]1COCC3(CC3)N1C2=O] | 580.2 | 94% |
| III-10 | 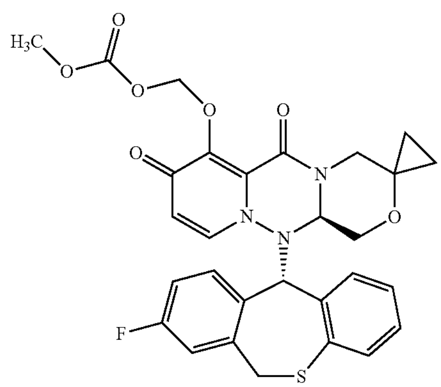 [SMILES: COC(=O)OCOc1c2n(ccc1=O)N([C@H]1c3ccc(F)cc3CSc3ccccc31)[C@@H]1COC3(CC3)CN1C2=O] | 580.2 | 95% |
| III-17 | 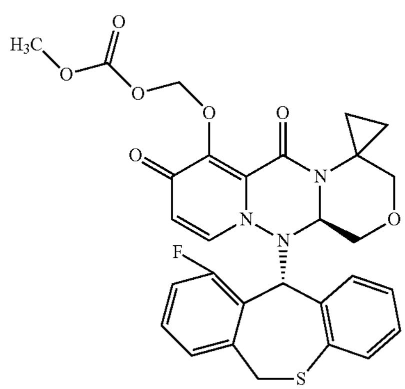 [SMILES: COC(=O)OCOc1c2n(ccc1=O)N([C@@H]1c3ccccc3SCc3cccc(Cl)c31)[C@@H]1COCC3(CC3)N1C2=O] | 580.2 | 95% |

-continued

| Compound | Structure | LCMS ([M + H]+) | Purity |
|---|---|---|---|
| III-18 | 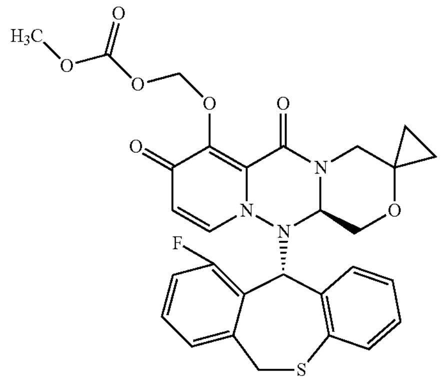 [SMILES: COC(=O)OCOc1c2n(ccc1=O)N([C@@H]1c3ccccc3SCc3cccc(Cl)c31)[C@@H]1COC3(CC3)CN1C2=O] | 580.2 | 97% |
| III-21 | 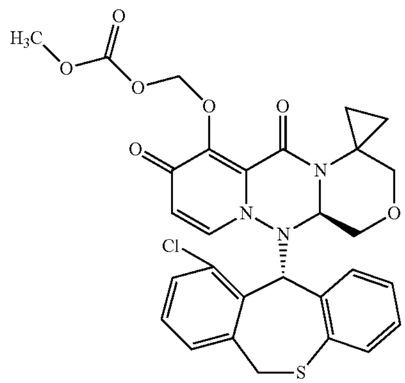 | 596.2 | 96% |
| III-22 | 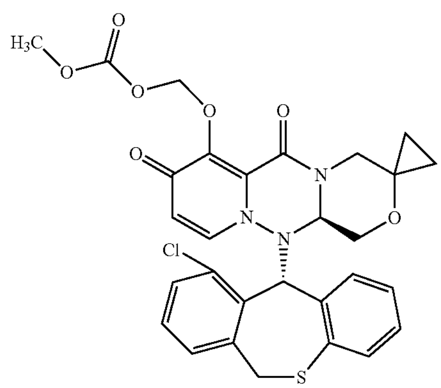 | 596.2 | 95% |
| III-33 | 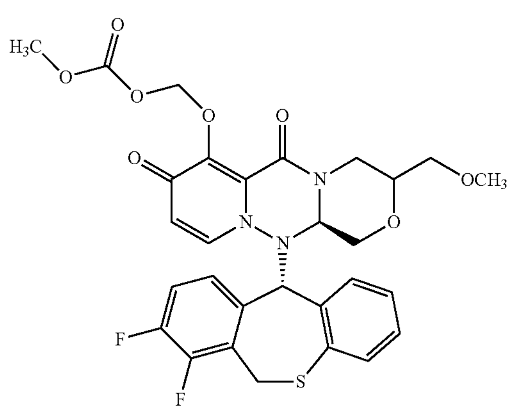 | 616.2 | 94% |

-continued
| Compound | Structure | LCMS ([M + H]+) | Purity |
|---|---|---|---|
| III-50 | 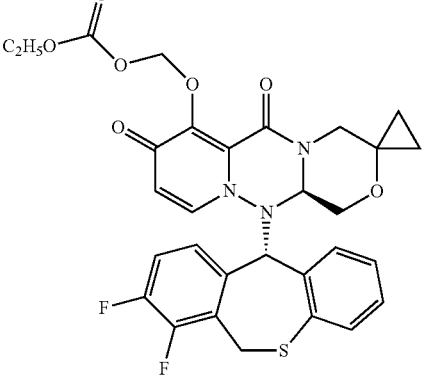 | 612.2 | 96% |
| III-51 | 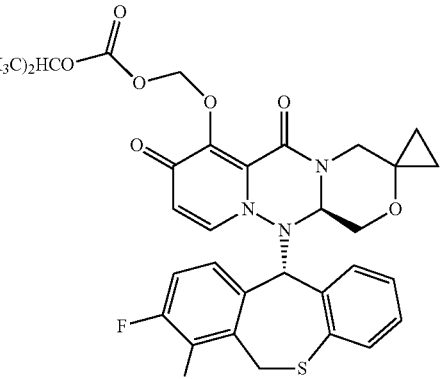 | 626.2 | 97% |
| III-52 | 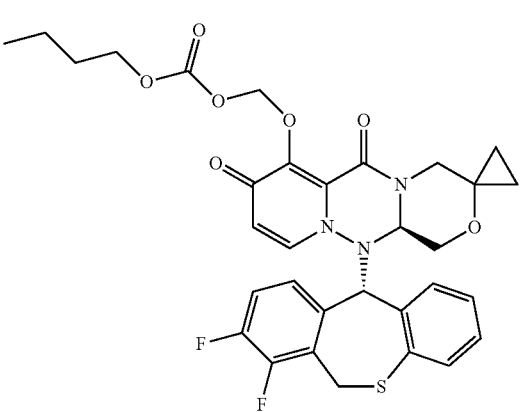 [SMILES: CCCCOC(=O)OCOc1c2n(ccc1=O)N([C@@H]1c3ccccc3SCc3c1ccc(F)c3F)[C@@H]1COC3(CC3)CN1C2=O] | 640.2 | 97% |
| III-54 | 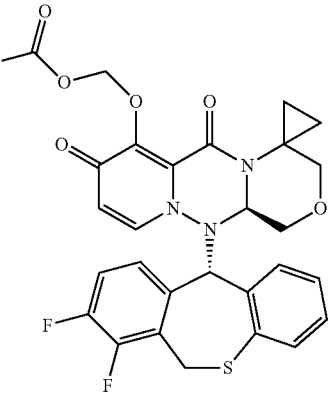 | 612.2 | 96% |

-continued
| Compound | Structure | LCMS ([M + H]+) | Purity |
|---|---|---|---|
| III-56 | 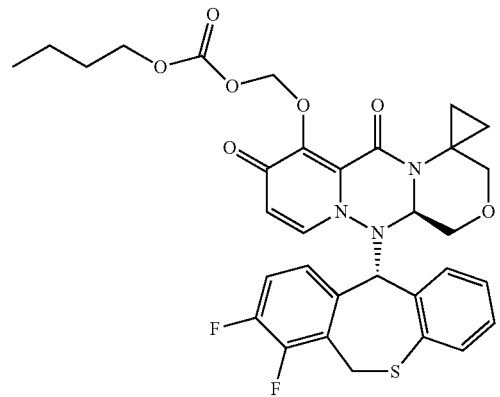 [SMILES: CCCCOC(=O)OCOc1c2n(ccc1=O)N([C@@H]1c3ccccc3SCc3c1ccc(F)c3F)[C@@H]1COCC3(CC3)N1C2=O] | 640.2 | 95% |
| III-59 | 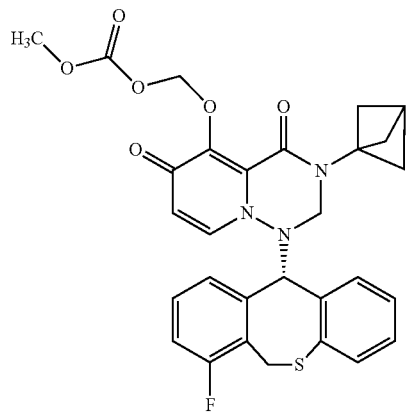 [SMILES: COC(=O)OCOc1c2n(ccc1=O)N([C@@H]1c3ccccc3SCc3c(F)cccc31)CN(C13CC(C1)C3)C2=O] | 564.2 | 95% |
| III-61 | 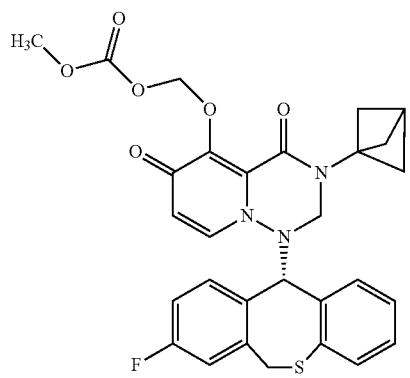 [SMILES: COC(=O)OCOc1c2n(ccc1=O)N([C@H]1c3ccc(F)cc3CSc3ccccc31)CN(C13CC(C1)C3)C2=O] | 564.2 | 96% |

-continued

| Compound | Structure | LCMS ([M + H]⁺) | Purity |
|---|---|---|---|
| III-66 | 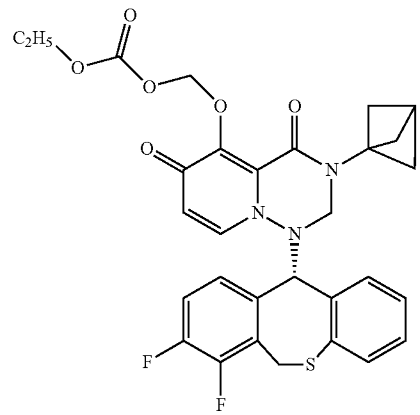 [SMILES: CCOC(=O)OCOc1c2n(ccc1=O)N([C@@H]1c3ccccc3SCc3c1ccc(F)c3F)CN(C13CC(C1)C3)C2=O] | 596.2 | 95% |
| III-67 | 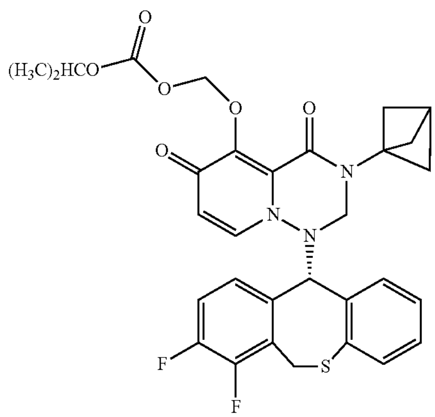 | 610.2 | 94% |
| IV-1 | 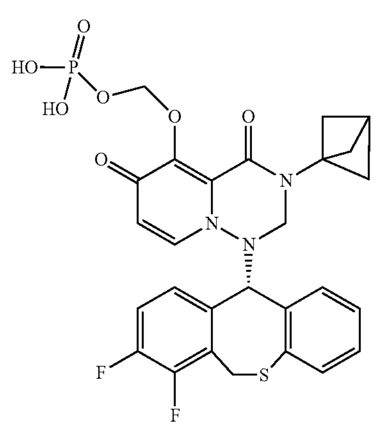 [SMILES: O=C1c2c(OCOP(=O)(O)O)c(=O)ccn2N([C@@H]2c3ccccc3SCc3c2ccc(F)c3F)CN1C12CC(C1)C2] | 604.2 | 93% |

-continued

| Compound | Structure | LCMS ([M + H]+) | Purity |
|---|---|---|---|
| IV-3 | 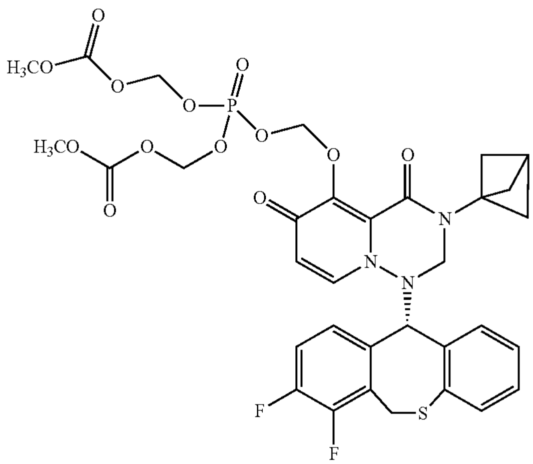 [SMILES: COC(=O)OCOP(=O)(OCOC(=O)OC)OCOc1c2n(ccc1=O)N([C@@H]1c3ccccc3SCc3c1ccc(F)c3F)CN(C13CC(C1)C3)C2=O] | 780.2 | 95% |
| IV-9 | 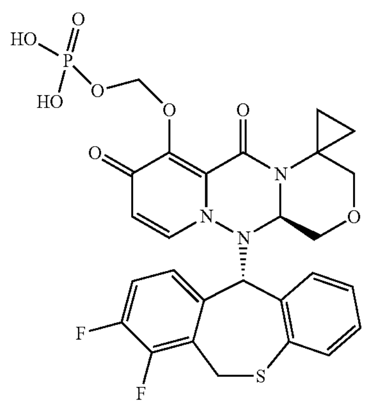 [SMILES: O=C1c2c(OCOP(=O)(O)O)c(=O)ccn2N([C@@H]2c3ccccc3SCc3c2ccc(F)c3F)[C@@H]2COCC3(CC3)N12] | 620.5 | 93% |
| IV-10 | 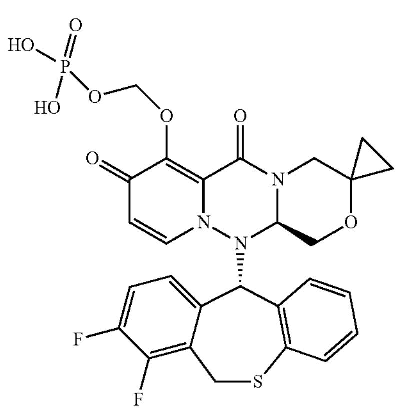 [SMILES: O=C1c2c(OCOP(=O)(O)O)c(=O)ccn2N([C@@H]2c3ccccc3SCc3c2ccc(F)c3F)[C@@H]2COC3(CC3)CN12] | 620.5 | 92% |

-continued

| Compound | Structure | LCMS ([M + H]⁺) | Purity |
|---|---|---|---|
| IV-11 | 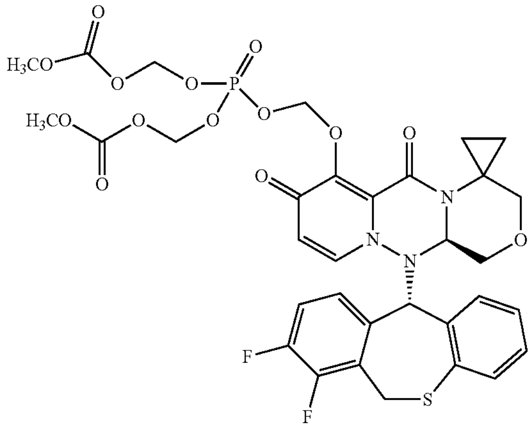 [SMILES: COC(=O)OCOP(=O)(OCOC(=O)OC)OCOc1c2n(ccc1=O)N([C@@H]1c3ccccc3SCc3c1ccc(F)c3F)[C@@H]1COCC3(CC3)N1C2=O] | 796.2 | 96% |
| IV-12 | 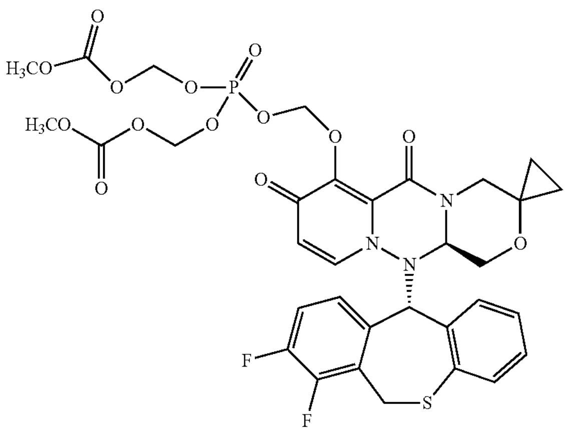 [SMILES: COC(=O)OCOP(=O)(OCOC(=O)OC)OCOc1c2n(ccc1=O)N([C@@H]1c3ccccc3SCc3c1ccc(F)c3F)[C@@H]1COC3(CC3)CN1C2=O] | 796.2 | 95% |

Embodiment 16: In Vitro Bioactivity and Cytotoxicity Study

Test compounds: the compounds of the present disclosure: Compound I-1, Compound I-5, Compound I-7, Compound I-8, Compound I-9, Compound I-10, Compound I-14, Compound I-21, Compound I-65, Compound I-66, Compound I-69, Compound I-77, Compound I-81, Compound I-83, Compound I-85, Compound I-89, Compound II-1, Compound II-2, Compound II-5, Compound II-6, Compound II-7, Compound II-8, Compound II-9, Compound II-10, Compound II-13, Compound II-14, Compound II-17, Compound II-18, Compound II-22, Compound II-29, Compound II-34, Compound II-65, Compound II-66, Compound II-67, Compound II-101; control compounds: VX-787, Baloxavir acid.

Test method for In vitro bioactivity study: MDCK cells were seeded into 384-well cell cultrue plate at a density of 2,000 cells/well, and then incubated at 37° C. overnight in a 5% $CO_2$ incubator. On the following day, the compounds were diluted and added into the wells (3-fold dilutions, 8 test concentrations), and the influenza virus A/PR/8/34 (H1N1) strain was then added to the cell culture wells at 2*TCID90 per well, and the final concentration of DMSO in the medium was 0.5%. The cell plate was incubated at 37° C. for 5 days in the 5% $CO_2$ incubator. After 5 days of culture, the cell viability was measured using the cell viability detection kit CCK8. The raw data were subjected to nonlinear fitting analysis of the inhibition rate and cytotoxicity of the compounds using GraphPad Prism software to obtain $EC_{50}$ values (see Table 1 for the results).

Method for cytotoxicity study: The cytotoxicity assay and antiviral activity assay of the compounds were performed in parallel, except for the absence of virus, other experimental conditions were consistent with the antiviral activity assay. After 5 days of culture, the cell viability was measured using the cell viability detection kit CCK8. Raw data were used for calculating compound cytotoxicity ($CC_{50}$) (see Table 1 for results).

TABLE 1

Cytotoxicity and inhibitory activity of compounds against influenza virus A/PR/8/34 (H1N1) Results (nM)

| CPD ID | $EC_{50}$ | $CC_{50}$ |
|---|---|---|
| I-1 | 0.50 | >1000 |
| I-5 | 0.44 | >1000 |
| I-7 | 0.83 | >1000 |
| I-8 | 0.75 | >1000 |
| I-9 | 0.40 | >1000 |
| I-10 | 0.70 | >1000 |
| I-14 | 0.32 | >1000 |
| I-21 | 0.60 | >1000 |
| I-65 | 0.37 | >1000 |
| I-66 | 0.58 | >1000 |
| I-69 | 0.35 | >1000 |

TABLE 1-continued

Cytotoxicity and inhibitory activity of compounds against influenza virus A/PR/8/34 (H1N1) Results (nM)

| CPD ID | $EC_{50}$ | $CC_{50}$ |
|---|---|---|
| I-77 | 0.16 | >1000 |
| I-81 | 0.19 | >1000 |
| I-83 | 0.21 | >1000 |
| I-85 | 0.18 | >1000 |
| I-89 | 0.17 | >1000 |
| II-1 | 0.45 | >1000 |
| II-2 | 0.51 | >1000 |
| II-5 | 0.22 | >1000 |
| II-6 | 0.26 | >1000 |
| II-7 | 0.93 | >1000 |
| II-8 | 0.47 | >1000 |
| II-9 | 0.28 | >1000 |
| II-10 | 0.24 | >1000 |
| II-13 | 0.38 | >1000 |
| II-14 | 0.31 | >1000 |
| II-17 | 0.26 | >1000 |
| II-18 | 0.28 | >1000 |
| II-22 | 0.36 | >1000 |
| II-29 | 0.57 | >1000 |
| II-34 | 0.39 | >1000 |
| II-65 | 0.45 | >1000 |
| II-66 | 0.18 | >1000 |
| II-67 | 0.48 | >1000 |
| II-101 | 0.94 | >1000 |
| VX-787 | 1.4 | >100 |
| Baloxavir acid | 1.4 | >1000 |

The results indicate that when compared with the control compounds, the compounds of the present disclosure had superior activity against H1N1 and had low cytotoxicity.

Embodiment 17: Rat PK Study

Intravenous injection: about 2 mg of Compound 11-5, Compound 11-6 and Compound 1-77 were accurately weighed out and added with appropriate amount of DMA, followed by vortex to a clean solution. An appropriate volume of 30% Solutol HS-15 aqueous solution and saline were added and vortexed, so that DMA: 30% Solutol HS-15: saline was 20:20:60 (v/v/v). The solution was filtered to give a 0.05 mg·mL$^{-1}$ pharmaceutical preparation. SD rats were given a single injection of 0.25 mg·kg$^{-1}$ of Compounds 11-5, 11-6 and 1-77 intravenously. 0.20 mL of blood was collected from the jugular vein before administration and 0.083 h, 0.25 h, 0.5 h, 1 h, 2 h, 4 h, 8 h, 12 h and 24 h after administration, and placed in an EDTA-K$_2$ anticoagulation tube. 150 μL of whole blood was accurately pipetted immediately, and added into a test tube to which 450 μL of acetonitrile has been added to precipitate proteins, and the tube was vortexed, and placed on wet ice. It was stored in a −90~−60° C. refrigerator for biological sample analysis. The concentration of the corresponding compound in the plasma of S-D rats was determined by LC-MS/MS analysis. The corresponding pharmacokinetic parameters were calculated using a non-compartmental model in Pharsight Phoenix 7.0. See Table 2a for the results.

Intragastric administration: about 4 mg of Compound III-2 was accurately weighed out and added with appropriate amount of PEG400, followed by vortex to a clean solution. An appropriate volume of 30% Solutol HS-15 aqueous solution and saline were added, and followed by vortex to give a pharmaceutical preparation of a concentration of 0.3 mg·mL$^{-1}$, with PEG400: 30% Solutol HS-15: saline=2:2:6 (v/v/v). SD rats were given a single oral administration of 3.0 mg·kg$^{-1}$ of Compounds III-2, and the concentration of Compound II-6 in the plasma of S-D rats was determined before administration and 0.25 h, 0.5 h, 1 h, 2 h, 4 h, 8 h, 12 h and 24 h after administration. See Table 2b for the results.

TABLE 2a

PK Parameters (Intravenous Injection) of Test Compounds

| PK (i.v.) | Compound | | |
|---|---|---|---|
| | II-5 | II-6 | I-77 |
| $T_{1/2}$ (h) | 2.49 | 2.97 | 2.96 |
| $AUC_{0-t}$ (ng · h · mL$^{-1}$) | 187 | 276 | 307 |
| CL (mL · kg$^{-1}$ · min$^{-1}$) | 20.9 | 13.6 | 13.0 |
| $Vd_{ss}$ (L · kg$^{-1}$) | 3.69 | 3.12 | 2.77 |

TABLE 2b

PK Parameters (intragastric administration) of Test Compounds

| PK (i.g.) | Compound III-2 |
|---|---|
| $T_{1/2}$ (h) | 3.32 |
| $T_{max}$ (h) | 1.67 |
| $C_{max}$ (ng · mL$^{-1}$) | 253 |
| $AUC_{0-t}$ (ng · h · mL$^{-1}$) | 1377 |
| F (%) | 47.2 |

The above results indicate that the compounds of the present disclosure have a low clearance rate and a long half life. The compounds of the present disclosure are effective for being prodrug and have a high absorption in vivo.

Embodiment 18: Efficacy on Mice

Female BALB/c mice were inoculated with influenza A virus (H1N1, A/WSN/33) by intranasal administration to establish an IAV mouse infection model. The vehicle, Compound III-2 (15 mpk) or oseltamivir phosphate (15 mpk) were orally administered twice a day. Animal weight and survival status were monitored daily during the test, and on the 5th day, some animals were killed to take lung tissue for virus titer detection, and the remaining mice were used for survival rate monitoring. The in vivo anti-influenza virus efficacy of the test compound was determined by virus titer in lung tissue, mouse body weight change and survival rate.

Virus titer in lung tissue: On the 5th day after virus infection, the average virus titer in the lung tissue of mice in the vehicle control group reached 7.20 Log 10 (number of plaques per gram of lung tissue), the average virus titer in the lung tissue of mice in the oseltamivir phosphate group was 3.74 Log 10 (number of plaques per gram of lung tissue). Compared with the vehicle group, oseltamivir phosphate significantly inhibited the replication of the virus in mice, and the average virus titer decreased by 3.46 Log 10 (number of plaques per gram of lung tissue), and the difference was very statistically significant ($p<0.01$) between the results, showing the expected efficacy; the average virus titer in the lung tissue of mice on the 5th day after treatment with test compound III-2 was 3.28 Log 10 (number of plaques per gram of lung tissue)), and compared with the vehicle group, the test compound significantly inhibited the replication of the virus in mice, and the average virus titer decreased by 3.92 Log 10 (number of plaques per gram of lung tissue), and the difference was extremely statistically significant (p<0.001) between the results, which is superior to the control compound oseltamivir phosphate (Table 3).

TABLE 3

Virus Titer in Lung Tissue

| Group | Influenza Virus Titer Log10 (plaques number/ gram of lung) | Statistical analysis (Compared with the solvent group) | |
|---|---|---|---|
| | | Mean difference | Statistic difference |
| Solvent | 7.20 ± 0.1024 | NA | NA |
| Oseltamivir phosphate | 3.74 ± 0.5205 | 3.46 | **(p < 0.01) |
| Compound III-2 | 3.28 ± 0.2813 | 3.92 | ***(p < 0.001) |

**P < 0.01 means very significant difference, P < 0.001 means extremely significant difference Body weight change and result analysis: The mice in the vehicle control group showed significant weight loss on the 3rd day after infection, and then continued to decline or even die; the weight of the mice in the oseltamivir phosphate group and the Compound III-2 group remained stable during the experiment, had no significant decline, and the mice were in good health.

Survival rate and result analysis: the mice in the vehicle control group were found dead on the 7th day after infection, and on the 10th day, all mice died or were euthanized due to weight loss to the humanity end point, and the survival rate was 0%; the mice in the oseltamivir phosphate group and in the Compound III-2 group maintained healthy during the experiment, and all animals survived to the predetermined experimental end point with a survival rate of 100%, indicating excellent anti-influenza efficacy in vivo.

The above description of the embodiments is merely to help understanding the method and the core concept of the present disclosure. It should be noted that, for those ordinary skilled in the art, various improvements and modifications can be made to the present disclosure without depart from the technical principle of the present disclosure, and these improvements and modifications also fall within the protective scope of the present disclosure.

What is claimed is:

1. A pyridone derivative represented by Formula (I) or a stereoisomer, a pharmaceutically acceptable salt, a solvate thereof,

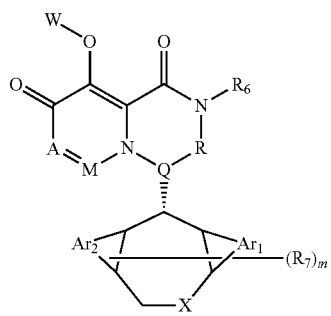

wherein:
(1) A is selected from N or $CR_1$, $R_1$ is selected from hydrogen, cyano, hydroxy, halogen, carboxyl, ester, amide, sulfonyl amide; or, $R_1$ is selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{6-10}$ aryl, $C_{6-10}$ aryloxy, $C_{6-10}$ aryloxy hydrocarbyl, $C_{6-10}$ arylamino, $C_{6-10}$ aryl sulfydryl, $C_{6-10}$ aryl carbonyl, $C_{1-6}$ hydrocarbyl sulfonyl, $C_{1-6}$ hydrocarbyl sulfonylamino, $C_{3-6}$ cycloalkyl sulfonyl, $C_{3-6}$ cycloalkyl sulfonylamino, $C_{6-10}$ aryl sulfonyl, $C_{6-10}$ aryl sulfonylamino, aminooxalyl amino, aminooxalyl, $C_{6-10}$ arylamino carbonyl or $C_{5-10}$ arylamino carbonylamino;

(2) M is selected from N or $CR_2$, $R_2$ is selected from hydrogen, cyano, hydroxy, halogen, carboxyl, ester, amide, sulfonyl amide; or, $R_2$ is selected from the following unsubstituted or substituted groups: $C_{1-6}$ hydrocarbyl, $C_{1-6}$ hydrocarbyloxy, $C_{1-6}$ hydrocarbylamino, $C_{1-6}$ hydrocarbylsulfydryl, carbonyl hydrazide, $C_{1-6}$ hydrocarbyl carbonyl, $C_{1-6}$ hydrocarbylamino carbonyl, $C_{1-6}$ hydrocarbylcarbonyl amino, $C_{1-6}$ hydrocarbyloxy carbonyl, $C_{1-6}$ hydrocarbylsulfinyl, $C_{1-6}$ hydrocarbylamino carbonylamino, $C_{3-6}$ cycloalkyl, $C_{3-6}$ cycloalkoxy, $C_{3-6}$ cycloalkylamino, $C_{3-6}$ cycloalkylsulfydryl, $C_{3-6}$ cycloalkylcarbonyl, $C_{3-6}$ cycloalkylamino carbonyl, $C_{3-6}$ cycloalkylcarbonyl amino, $C_{3-6}$ cycloalkylamino carbonylamino, $C_{4-8}$ heterocycloalkyl, $C_{4-8}$ heterocycloalkoxy, $C_{4-8}$ heterocycloalkylamino, $C_{4-8}$ heterocycloalkyl sulfydryl, $C_{4-8}$ heterocycloalkyl carbonyl, $C_{4-8}$ heterocycloalkylamino carbonyl, $C_{5-10}$ aryl, $C_{5-10}$ aryloxy, $C_{5-10}$ aryloxy hydrocarbyl, $C_{5-10}$ arylamino, $C_{5-10}$ aryl sulfydryl, $C_{5-10}$ aryl carbonyl, $C_{1-6}$ hydrocarbyl sulfonyl, $C_{1-6}$ hydrocarbyl sulfonylamino, $C_{3-6}$ cycloalkyl sulfonyl, $C_{3-6}$ cycloalkyl sulfonylamino, $C_{5-10}$ aryl sulfonyl, $C_{5-10}$ aryl sulfonylamino, aminooxalyl amino, aminooxalyl, $C_{5-10}$ arylamino carbonyl or $C_{5-10}$ arylamino carbonylamino;

(3) Q is selected from N or $CR_3$, $R_3$ is selected from hydrogen, cyano, carboxyl, ester, amide; or, $R_3$ is selected from the following unsubstituted or substituted groups: $C_{1-6}$ hydrocarbyl, $C_{3-6}$ cycloalkyl, $C_{4-8}$ heterocycloalkyl, $C_{5-10}$ aryl, $C_{3-6}$ cycloalkyl sulfydryl, spirocyclic ring, bridged cyclic ring, $C_{3-6}$ cycloalkyl sulfydryl $C_{1-6}$ hydrocarbyl, $C_{3-6}$ cycloalkyl $C_{1-6}$ hydrocarbyl sulfydryl $C_{1-6}$ hydrocarbyl, $C_{3-6}$ cycloalkyl $C_{1-6}$ hydrocarbyl sulfydryl cycloalkyl, $C_{3-6}$ cycloalkyloxy cycloalkyl, cycloamide $C_{1-6}$ hydrocarbyl, cycloamide cycloalkyl, cyclosulfonyl $C_{1-6}$ hydrocarbyl, cyclosulfonyl cycloalkyl;

(4) $R_6$ and R are connected and form a sixth ring together with a nitrogen atom both connected therewith, and the sixth ring is spiro and optionally contains 1, 2, 3 or more groups independently selected from heteroatom, C=O, S=O or SO$_2$, in addition to the nitrogen atom which R and R$_6$ are both connected with; a common carbon atom of the spiro ring and a nitrogen atom shared by the spiro ring and a parent ring are adjacent or spaced by one atom; a ring in the spiro ring that shares the nitrogen atom with a parent ring has an oxygen atom, or a nitrogen atom at a position opposite to the nitrogen atom;

(5) m is 0, 1, 2, 3, 4 or 5, and R$_7$ is selected from hydrogen, hydroxy, cyano, halogen, carboxyl, ester, sulfonyl amide, amide; or, R$_7$ is selected from the following unsubstituted or substituted groups: C$_{1-6}$ hydrocarbyl, C$_{1-6}$ hydrocarbyloxy, C$_{1-6}$ hydrocarbylamino, C$_{1-6}$ hydrocarbylsulfydryl, carbonyl hydrazide, C$_{1-6}$ hydrocarbyl carbonyl, C$_{1-6}$ hydrocarbylamino carbonyl, C$_{1-6}$ hydrocarbylcarbonyl amino, C$_{1-6}$ hydrocarbyloxy carbonyl, C$_{1-6}$ hydrocarbylsulfinyl, C$_{1-6}$ hydrocarbylamino carbonylamino, C$_{3-6}$ cycloalkyl, C$_{3-6}$ cycloalkoxy, C$_{3-6}$ cycloalkylamino, C$_{3-6}$ cycloalkylsulfydryl, C$_{3-6}$ cycloalkylcarbonyl, C$_{3-6}$ cycloalkylamino carbonyl, C$_{3-6}$ cycloalkylcarbonyl amino, C$_{3-6}$ cycloalkylamino carbonylamino, C$_{4-8}$ heterocycloalkyl, C$_{4-8}$ heterocycloalkoxy, C$_{4-8}$ heterocycloalkylamino, C$_{4-8}$ heterocycloalkyl sulfydryl, C$_{4-8}$ heterocycloalkyl carbonyl, C$_{4-8}$ heterocycloalkylamino carbonyl, C$_{5-10}$ aryl, C$_{5-10}$ aryloxy, C$_{5-10}$ aryloxy hydrocarbyl, C$_{5-10}$ arylamino, C$_{5-10}$ aryl sulfydryl, C$_{5-10}$ aryl carbonyl, C$_{1-6}$ hydrocarbyl sulfonyl, C$_{1-6}$ hydrocarbylsulfonyl amide, C$_{3-6}$ cycloalkyl sulfonyl, C$_{3-6}$ cycloalkylsulfonyl amide, C$_{5-10}$ aryl sulfonyl, C$_{5-10}$ arylsulfonyl amide, aminooxalyl amino, aminooxalyl, C$_{5-10}$ arylamino carbonyl or C$_{5-10}$ arylamino carbonylamino;

(6) X is selected from Y(CH$_2$)$_n$, —CH(OCH$_3$), —CH(SCH$_3$), N, O or S, Y is a single bond, NH, O or S, and n is 0, 1, 2 or 3;

(7) W is hydrogen or a group selected from the following groups: (a) —C(=O)—R$_8$; (b) —C(=O)—(CH$_2$)$_k$—R$_8$, k is selected from 0-3; (c) C(=O)—O—(CH$_2$)$_k$—R$_8$, k is selected from 0-3; (d) —CH$_2$—O—R$_8$; (e) —CH$_2$-O-C(=O)—R$_8$; (f) —CH$_2$—O—C(=O)—O—R$_8$; (g) —CH(—CH$_3$)—O—C(=O)—R$_8$; (h) CH(—CH$_3$)—O—C(=O)—O—(CH$_2$)$_k$—R$_8$, k is selected from 0-3; (i) —CH$_2$—O—P(=O)(OH)$_2$; (j) —CH$_2$—O—P(=O)(OPh)(NHR$_8$); (k) —CH$_2$—O—P(=O)(OCH$_2$OC(=O)OR$_8$)$_2$; R$_8$ is selected from the following unsubstituted or substituted groups: C$_{1-6}$ hydrocarbyl, C$_{1-6}$ hydrocarbyloxy, C$_{1-6}$ hydrocarbylamino, C$_{1-6}$ hydrocarbylsulfydryl, carbonyl hydrazide, C$_{1-6}$ hydrocarbyl carbonyl, C$_{1-6}$ hydrocarbylamino carbonyl, C$_{1-6}$ hydrocarbylcarbonyl amino, C$_{1-6}$ hydrocarbyloxy carbonyl, C$_{1-6}$ hydrocarbylsulfinyl, C$_{1-6}$ hydrocarbylamino carbonylamino, C$_{3-6}$ cycloalkyl, C$_{3-6}$ cycloalkoxy, C$_{3-6}$ cycloalkylamino, C$_{3-6}$ cycloalkylsulfydryl, C$_{3-6}$ cycloalkylcarbonyl, C$_{3-6}$ cycloalkylamino carbonyl, C$_{3-6}$ cycloalkylcarbonyl amino, C$_{3-6}$ cycloalkylamino carbonylamino, C$_{4-8}$ heterocycloalkyl, C$_{4-8}$ heterocycloalkoxy, C$_{4-8}$ heterocycloalkylamino, C$_{4-8}$ heterocycloalkyl sulfydryl, C$_{4-8}$ heterocycloalkyl carbonyl, C$_{4-8}$ heterocycloalkylamino carbonyl, C$_{5-10}$ aryl, C$_{5-10}$ aryloxy, C$_{5-10}$ aryloxy hydrocarbyl, C$_{5-10}$ arylamino, C$_{5-10}$ aryl sulfydryl, C$_{5-10}$ aryl carbonyl, C$_{1-6}$ hydrocarbyl sulfonyl, C$_{1-6}$ hydrocarbyl sulfonylamino, C$_{3-6}$ cycloalkyl sulfonyl, C$_{3-6}$ cycloalkyl sulfonylamino, C$_{5-10}$ aryl sulfonyl, C$_{5-10}$ aryl sulfonylamino, aminooxalyl amino, aminooxalyl, C$_{5-10}$ arylamino carbonyl or C$_{5-10}$ arylamino carbonylamino;

(8) Ar$_1$ and Ar$_2$ are independently selected from a phenyl ring, or a heteroaromatic ring containing 1, 2, 3 or more heteroatoms.

2. The pyridone derivative or the stereoisomer, the pharmaceutically acceptable salt, or the solvate thereof according to claim 1, wherein Ar$_1$ and Ar$_2$ are both a phenyl ring and the pyridone derivative is represented by Formula (II):

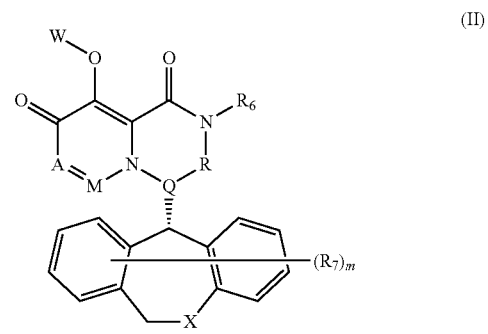

or, at least one of Ar$_1$ and Ar$_2$ is a heteroaromatic ring.

3. The pyridone derivative or the stereoisomer, the pharmaceutically acceptable salt, or the solvate thereof according to claim 1, wherein, in the heterocyclic ring or the heteroaromatic ring, a heteroatom is dependently selected from N, O or S.

4. The pyridone derivative or the stereoisomer, the pharmaceutically acceptable salt, or the solvate thereof according to claim 1, wherein the sixth ring is a spiro ring, a ring in the spiro ring that shares the nitrogen atom with a parent ring is a 5-membered, 6-membered, 7-membered or 8-membered ring, and another ring is a 3-membered, 4-membered, 5-membered or 6-membered carboatomic, oxygen-containing heterocyclic or sulfur-containing heterocyclic ring unsubstituted or substituted by a substituent selected from halogen, C$_{1-3}$ hydrocarbyl or C$_{1-3}$ halohydrocarbyl.

5. The pyridone derivative or the stereoisomer, the pharmaceutically acceptable salt, or the solvate thereof according to claim 4, wherein when the another ring has a substituent, the substituent is selected from methyl, fluoro, chloro, bromo, monofluoromethyl, difluoromethyl, trifluoromethyl, hydroxymethyl, methoxymethyl, methoxyethyl, chloromethyl.

6. The pyridone derivative or the stereoisomer, the pharmaceutically acceptable salt, or the solvate thereof according to claim 1, wherein in Formula (I), the sixth ring is selected from the following groups:

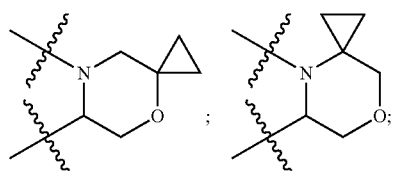

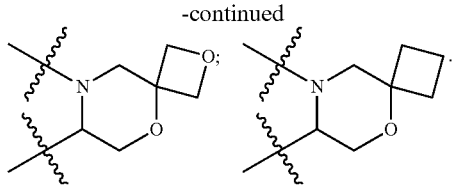

7. The pyridone derivative or the stereoisomer, the pharmaceutically acceptable salt, or the solvate thereof according to claim 1, wherein the pyridone derivative is represented by Formula IIa or Formula IIb:

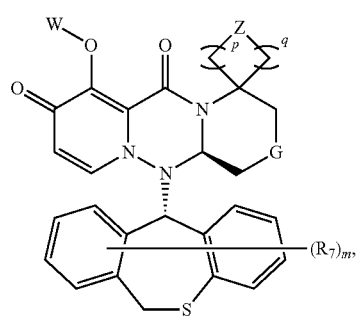

IIa

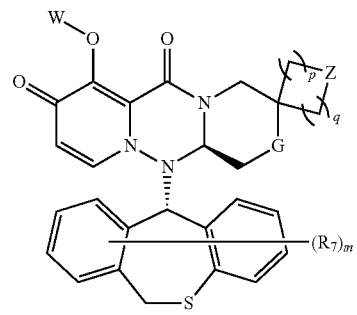

IIb in Formula IIa and Formula IIb,
G is O;
Z is selected from $CH_2$, O or S;
p and q are respectively 0, 1 or 2, and the two are not 0 at the same time, and when Z is O or S, p+q is greater than or equal to 2; and
the definitions of W, $R_7$ and m are respectively the same as in claim 1.

8. The pyridone derivative or the stereoisomer, the pharmaceutically acceptable salt, or the solvate thereof according to claim 7, wherein in Formula IIa and Formula IIb, p+q=1 or, 2 or 3, and Z is $CH_2$; or, p=1 or 2, q=1 or 2, and Z is O or S.

9. The pyridone derivative or the stereoisomer, the pharmaceutically acceptable salt, or the solvate thereof according to claim 7, wherein $R_7$ is selected from hydrogen, hydroxy, cyano, halogen, $C_{1-6}$ hydrocarbyl, $C_{1-6}$ halohydrocarbyl, $C_{3-6}$ cycloalkyl, $C_{1-6}$ alkoxy $C_{1-6}$ hydrocarbyl, hydroxy $C_{1-6}$ hydrocarbyl, $C_{1-6}$ hydrocarbyloxy.

10. The pyridone derivative or the stereoisomer, the pharmaceutically acceptable salt, or the solvate thereof according to claim 9, wherein $R_7$ is connected to a phenyl ring, R7 is selected from F, Cl, Br, methyl, or difluoromethyl; and m is 1, 2 or 3.

11. The pyridone derivative or the stereoisomer, the pharmaceutically acceptable salt, or the solvate thereof according to claim 7, wherein W is selected from the following groups: (a) —C(=O)—$R_8$; (b) —C(=O)—$(CH_2)_k$—$R_8$, k is selected from 0-3; (c) —C(=O)—O—$(CH_2)_k$—$R_8$, k is selected from 0-3; (e) —$CH_2$—O—C(=O)—$R_8$; (f) —$CH_2$—O—C(=O)—O—$R_8$; (g) —CH(—$CH_3$)—O—C(=O)$_k$—$R_8$; (h) —CH(—$CH_3$)—O—C(=O)—O—$(CH_2)_k$—$R_8$, k is selected from 0-3; (i) —$CH_2$—O—P(=O)(OH)$_2$; (j) —$CH_2$—O—P(=O)(OPh)(NHR$_8$); (k) —$CH_2$—O—P(=O)(OCH$_2$OC(=O)OR$_8$)$_2$; $R_8$ is selected from methyl, ethyl, isopropyl, or butyl.

12. The pyridone derivative or the stereoisomer, the pharmaceutically acceptable salt, or the solvate thereof according to claim 1, wherein the pyridone derivative is selected from the following compounds:

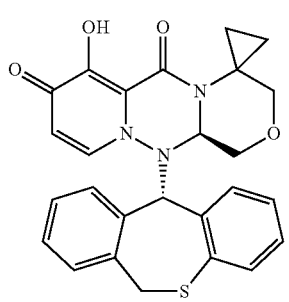

II-1

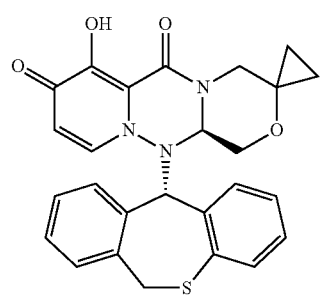

II-2

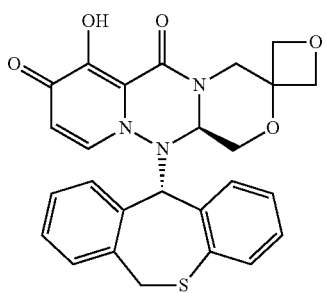

II-3

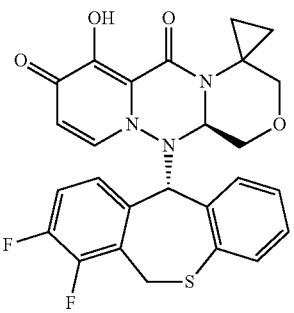

II-5

II-6
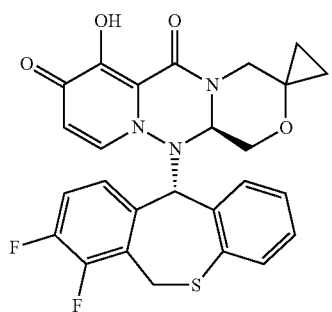
II-7
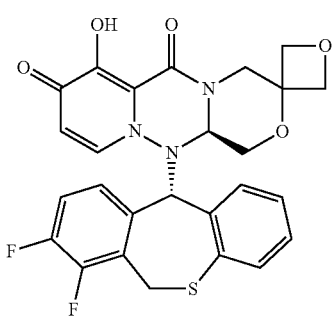
II-9
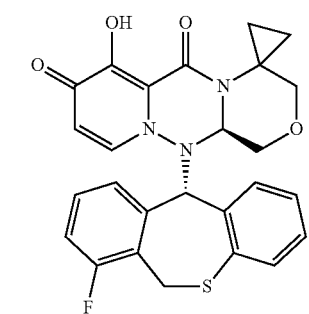
II-10
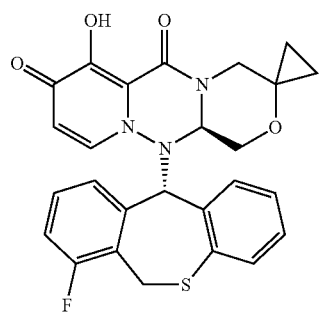
II-11
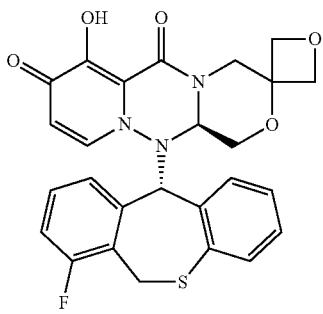
II-13
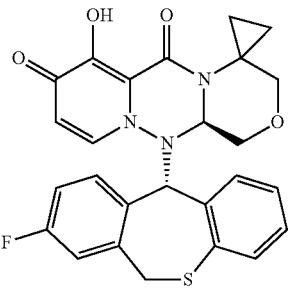
II-14
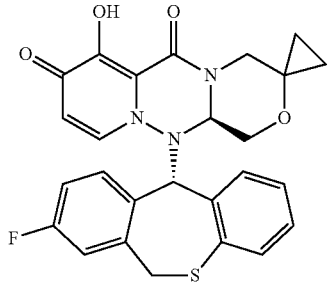
II-15
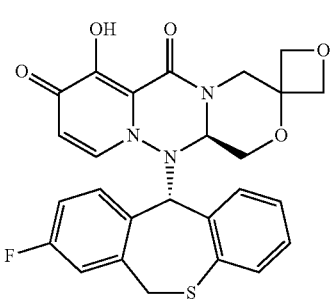
II-17
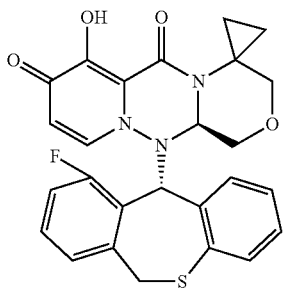
II-18
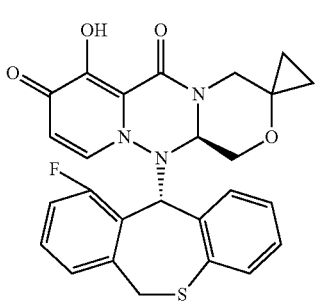

II-19
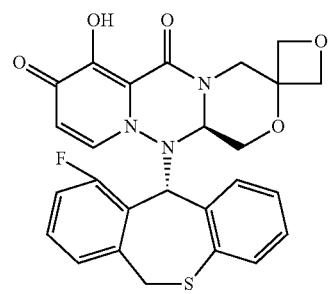
II-21
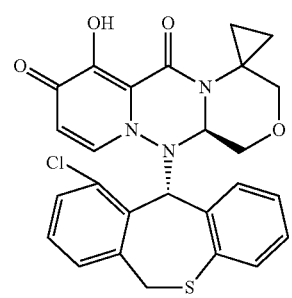
II-22
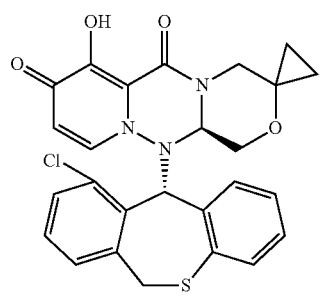
II-23
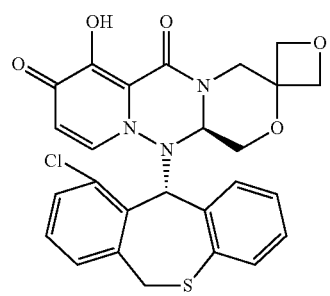
III-1
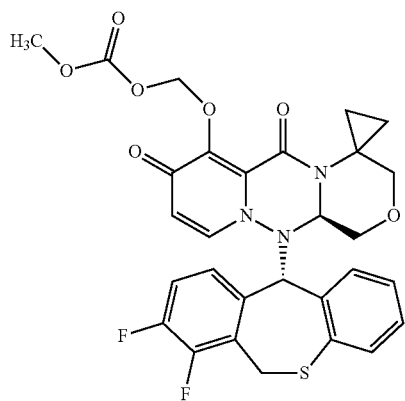
III-2
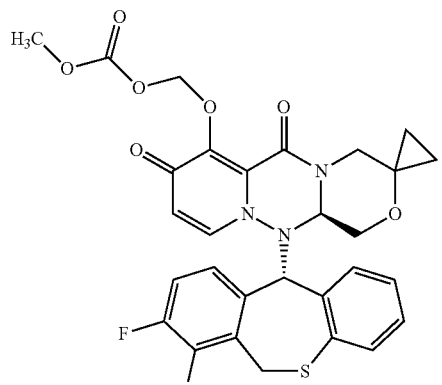
III-3
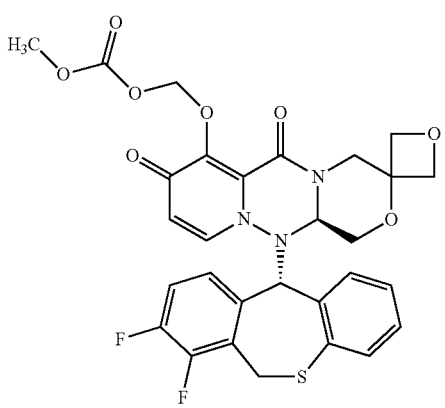
III-5
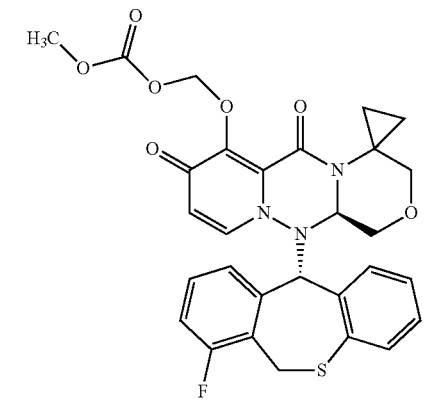
III-6
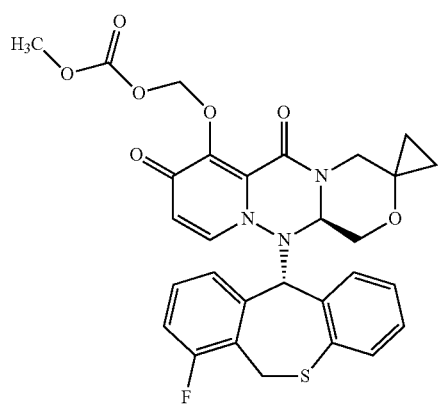

-continued
III-7
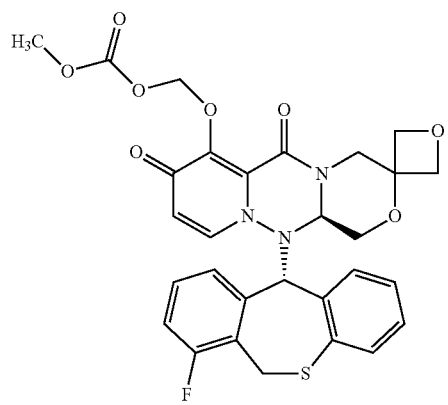
III-13
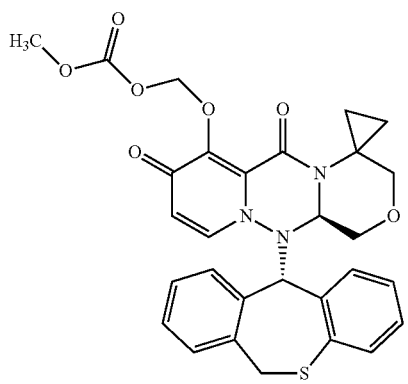
III-9
III-14
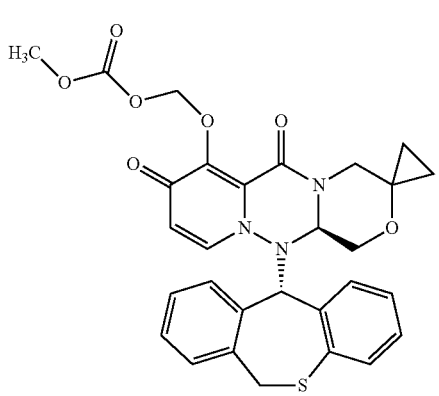
III-10
III-15
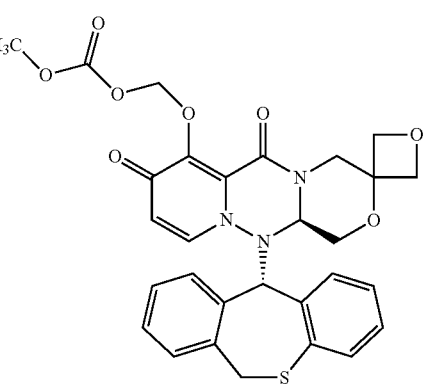
III-11
III-17
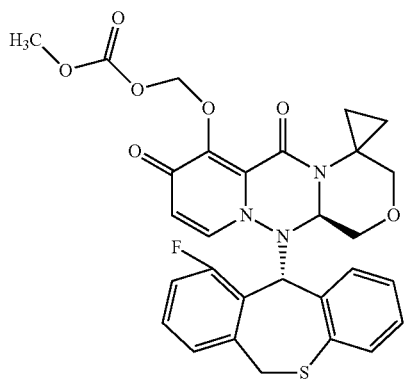

III-18
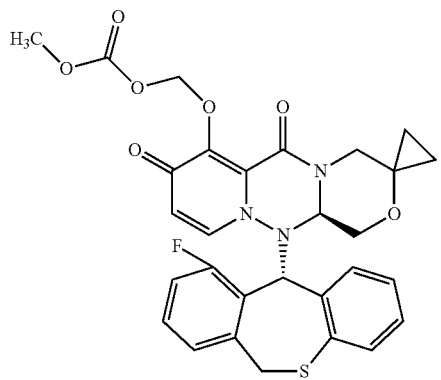
III-19
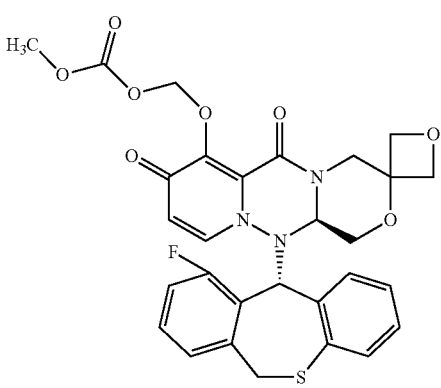
III-21
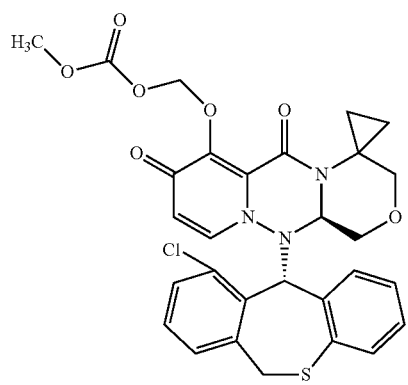
III-22
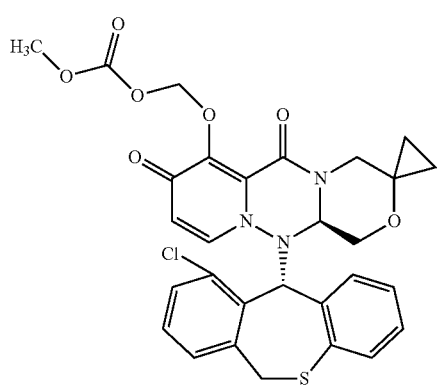
III-23
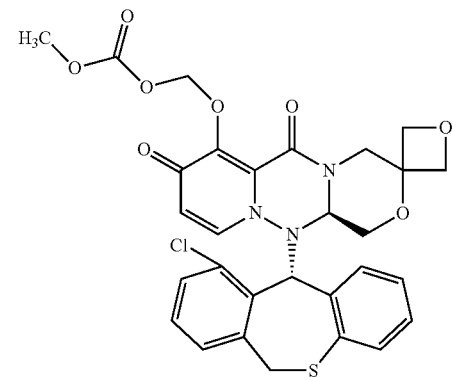
III-49
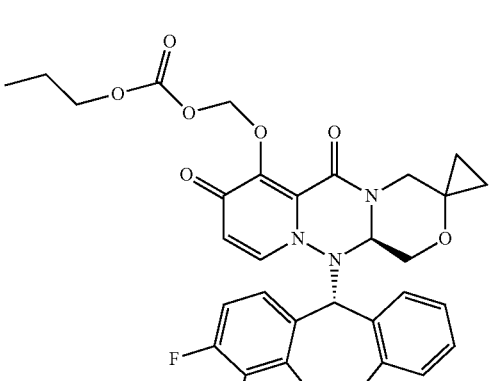
III-50
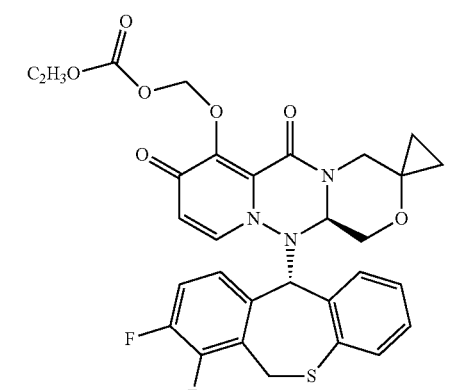
III-51
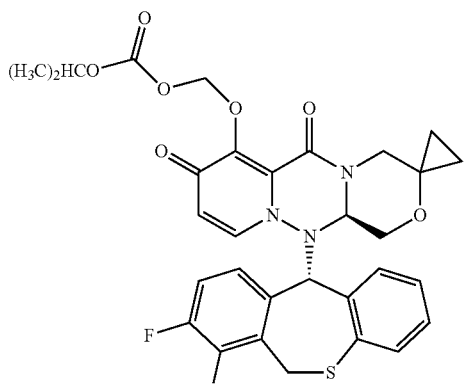

III-52
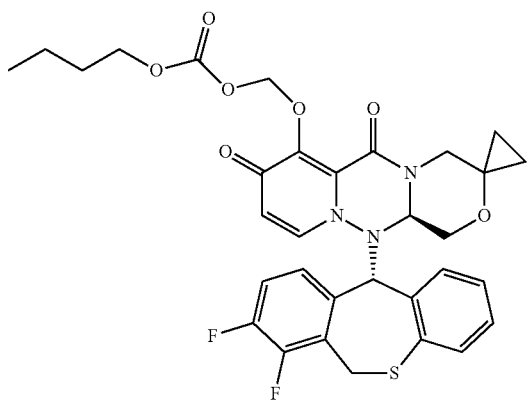
III-53
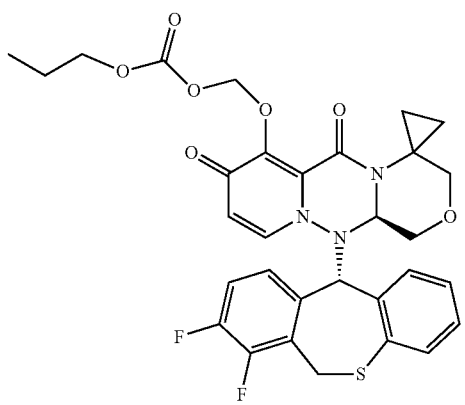
III-54
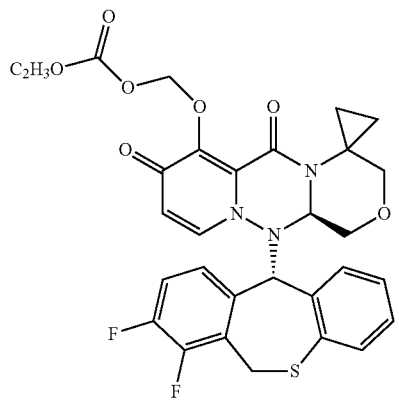
III-55
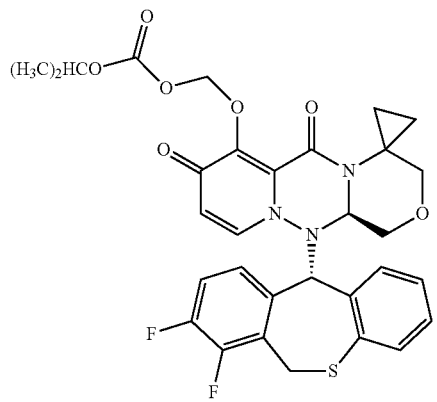
III-56
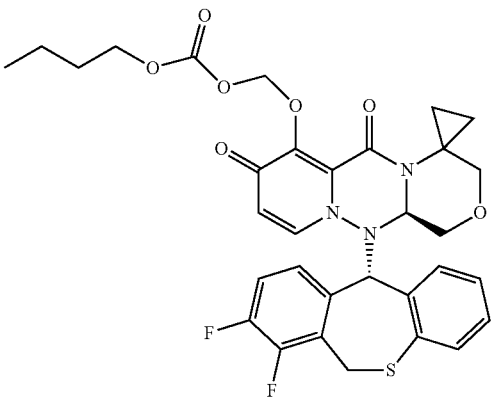
IV-9
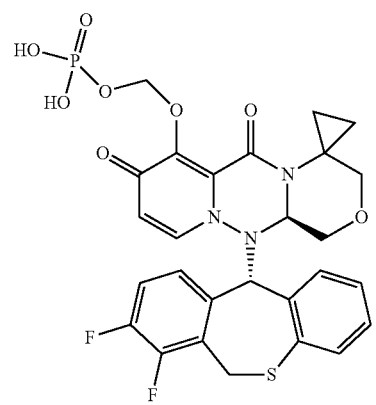
IV-10
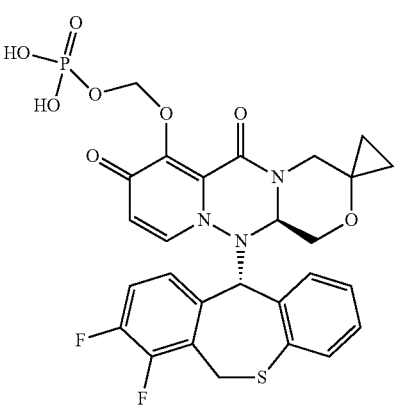

IV-11

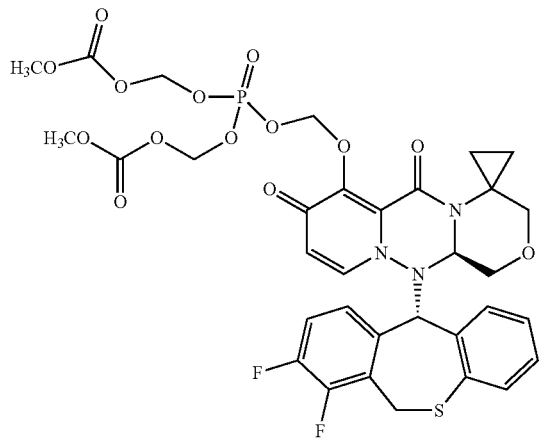

IV-12

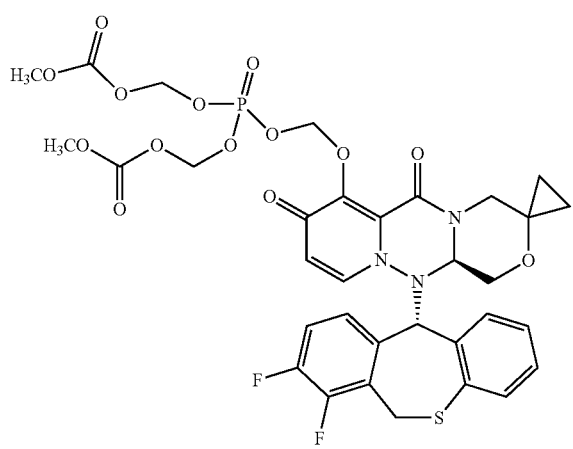

IV-13

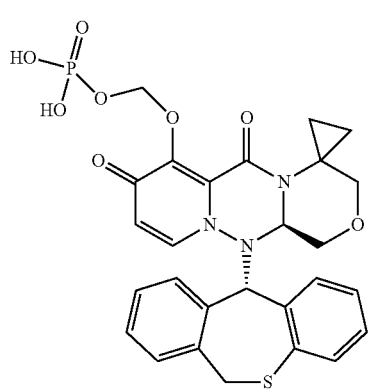

IV-14

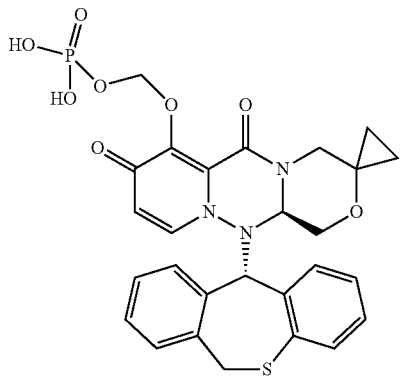

IV-15

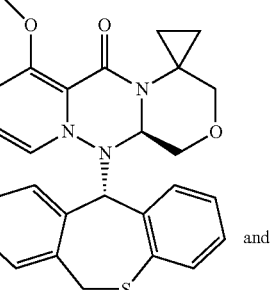

and

IV-16

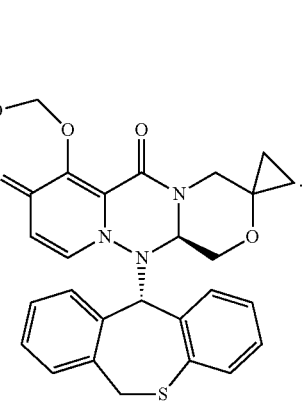

13. A pharmaceutical composition containing the pyridone derivative represented by Formula (I) or the stereoisomer, the pharmaceutically acceptable salt, or the solvate thereof according to claim 1, wherein the pharmaceutical composition is an antiviral pharmaceutical composition optionally comprising one or more therapeutic agents selected from the group consisting of a neuraminidase inhibitor, a nucleoside drug, a PB2 inhibitor, a PB1 inhibitor, an M2 inhibitor or other anti-influenza drugs.

14. The pharmaceutical composition according to claim 13, wherein the pharmaceutical composition is a pharmaceutical preparation selected from a tablet, a powder, a capsule, a granule, an oral liquid, an injection, a suppository, a pill, a cream, a paste, a gel, a pulvis, an inhalant, a suspension, a dry suspension, a patch, a lotion or a nano preparation.

15. A method for treating a viral infection disease, wherein the method comprises administering to an animal or human in need of the treatment an effective amount of the pyridone derivative represented by Formula (I) or the stereoisomer, the pharmaceutically acceptable salt, or the solvate thereof according to claim 1, wherein the viral infection disease is an infectious disease caused by influenza type A and/or influenza type B.

16. A method for treating a viral infection disease, wherein the method comprises administering to an animal or human in need of the treatment an effective amount of the pharmaceutical composition according to claim 13, wherein the viral infection disease is an infectious disease caused by influenza type A and/or influenza type B.

17. The pyridone derivative or the stereoisomer, the pharmaceutically acceptable salt, or the solvate thereof according to claim 9, wherein $R_7$ is connected to a phenyl ring and is selected from F, Cl, Br, methyl or trifluoromethyl; and m is 1 or 2.

* * * * *